(12) United States Patent
Bockovich et al.

(10) Patent No.: US 7,786,112 B2
(45) Date of Patent: Aug. 31, 2010

(54) INHIBITORS OF CYCLIN-DEPENDENT KINASES, COMPOSITIONS AND USES RELATED THERETO

(75) Inventors: Nicholas Bockovich, Malden, MA (US); Arthur F. Kluge, Lincoln, MA (US); Chris Oalmann, Watertown, MA (US); Krishna K. Murthi, Cambridge, MA (US); Siya Ram, Winchester, MA (US); Zhongguo Wang, Lexington, MA (US); Jianxing Huang, N. Billerica, MA (US)

(73) Assignee: Agennix USA Inc., Princeton, NJ (US)

( * ) Notice: Subject to any disclaimer, the term of this patent is extended or adjusted under 35 U.S.C. 154(b) by 654 days.

(21) Appl. No.: 10/819,899

(22) Filed: Apr. 6, 2004

(65) Prior Publication Data

US 2004/0266853 A1 Dec. 30, 2004

Related U.S. Application Data

(60) Provisional application No. 60/460,921, filed on Apr. 7, 2003, provisional application No. 60/531,872, filed on Dec. 23, 2003.

(51) Int. Cl.
*A61K 31/5377* (2006.01)
*C07D 413/14* (2006.01)

(52) U.S. Cl. .................................. 514/232.8; 514/121
(58) Field of Classification Search .................. 544/121; 514/232.8
See application file for complete search history.

(56) References Cited

U.S. PATENT DOCUMENTS

| 2,989,538 | A | 6/1961 | Flores et al. |
| 3,211,731 | A | 10/1965 | Schmidt et al |
| 3,211,732 | A | 10/1965 | Schmidt et al. |
| 5,593,356 | A | 1/1997 | Takeda |
| 5,593,997 | A | 1/1997 | Dow et al. |
| 6,291,504 | B1 | 9/2001 | Nugiel et al. |
| 6,407,103 | B2 | 6/2002 | Nugiel et al. |
| 6,413,957 | B1 | 7/2002 | Nugiel et al. |
| 6,753,329 | B2 * | 6/2004 | Bockovich et al. ....... 514/232.8 |
| 2001/0027195 | A1 | 10/2001 | Nugiel et al. |
| 2003/0165873 | A1 | 9/2003 | Come et al. |
| 2004/0043388 | A1 | 3/2004 | Come et al. |

FOREIGN PATENT DOCUMENTS

| EP | 0203679 | 12/1986 |
| JP | 60-130521 | 7/1985 |
| JP | 62-099361 | 5/1987 |
| WO | WO 94/13677 | 6/1994 |
| WO | WO 98/05335 | 2/1998 |
| WO | WO 99/54308 | 10/1999 |
| WO | WO 00/21926 | 4/2000 |
| WO | WO 02/34721 | 5/2002 |
| WO | WO 02/40182 | 5/2002 |
| WO | WO 02/44174 | 6/2002 |
| WO | WO 02/067654 | 9/2002 |
| WO | WO 02/070662 | 9/2002 |
| WO | WO 02/093269 | 11/2002 |
| WO | WO 03/004491 | 1/2003 |
| WO | WO 03/033499 | 4/2003 |
| WO | WO 03/063764 | 8/2003 |

OTHER PUBLICATIONS

Mosher, et al; "Benzene Ring Substituted Indeno[1,2-c]pyrazol-4(1H)-ones"; J. Org. Chem, vol. 35, No. 11, 1970 pp. 3685-3688.
Nugiel, et al; "Indenopyrazoles as Novel Cyclin Dependent Kinase (CDK) Inhibitors"; J Med Chem. 2001, 44, 1334-1336.
Nugiel, et al; "Synthesis and Evaluation of Indenopyrazoles as Cyclin-Dependent Kinase Inhibitors. 2. Probing the Indeno Ring Substituent Pattern"; J Med Chem, 2002, 45, 5524-5232.
Yue, et al; "Synthesis and Evaluation of Indenopyrazoles as Cyclin-Dependent Kinase Inhibitors. 3. Structure Activity Relationships at C3 (1,2)"; J Med Chem 2002, 45, 5233-5248.
Shaw, et al., "Purines, pyimidines and imidazoles . . . "; Chemical Abstracts, vol. 75 No. 1; Jul. 5, 1971, Columbus, Ohio, abstract No. 5837.
"Protein Kinase Targets: Strategies for Drug Development"; Conference presentation Jun. 10-11, 2003; Westin Copley Place Hotel, Boston, MA.
Search Report issued for PCT/US2004/010381 dated Feb. 3, 2005.

* cited by examiner

*Primary Examiner*—Rebecca L Anderson
(74) *Attorney, Agent, or Firm*—Yankwich & Associates, P.C.; Leon R. Yankwich; Michael R. Wesolowski

(57) ABSTRACT

The invention pertains to novel cyclin dependent kinase inhibitors (cdks) and specifically, but not exclusively, as inhibitors of cdk/cyclin complexes. As described herein, the inhibitors of this invention are capable of inhibiting the cell-cycle machinery and consequently may be useful in modulating cell-cycle progression, ultimately controlling cell growth and differentiation. Such compounds would be useful for treating subjects having disorders associated with excessive cell proliferation.

3 Claims, 14 Drawing Sheets

| TREATMENT | DOSE (mg/Kg) | MAX % BW LOSS (DAY) | PR | CR | CURES | MAX TGI (DAY) | LCK (Td:2.2) |
|---|---|---|---|---|---|---|---|
| VEHICLE | ----- | ------ | --- | --- | --- | ---------- | ---------- |
| CYTOXAN (QODx5) | 100 (ip) | -8.5 (16) | 9 | 1 | 0 | 98.5 (19) | 3.47 |
| A37 (QDx10) | 60 (iv) | -23.6 (12) | 9 | 1 | 3 | 98.5 (19) | 3.64 |
| A37 (QDx10) | 50 (iv) | -14 (16) | 5 | 1 | 0 | 94.5 (16) | 1.73 |
| A37 (QDx10) | 40 (iv) | -9.7 (16) | 1 | 0 | 0 | 82.5 (14) | 1.23 |

| TREATMENT | DOSE (mg/Kg) | MAX % BW LOSS (DAY) | PR | CR | CURES | MAX TGI (DAY) | LCK (Td:2.2) |
|---|---|---|---|---|---|---|---|
| VEHICLE | ----- | ------ | --- | --- | --- | ---------- | ---------- |
| CYTOXAN (QDx5) | 100 (ip) | ------ | 5 | 0 | 0 | 96 (25) | 3.47 |
| A37 (QDx5/2/5) | 50 (iv) | -5.7 (15) | 8 | 0 | 1 | 98 (18) | 1.69 |
| A37 (QDx5/2/5) | 40 (iv) | ------ | 4 | 1 | 0 | 89 (15) | 1.21 |
| A37 (QDx5/2/5) | 30 (iv) | ------ | 1 | 0 | 0 | 76 (15) | 0.29 |

| TREATMENT | DOSE (mg/Kg) | TOXIC DEATHS | PR | CR | CURES | MAX TGI (DAY) | LCK (Td:2.2) |
|---|---|---|---|---|---|---|---|
| VEHICLE | ----- | 0 | --- | --- | --- | ---------- | ---------- |
| CYTOXAN (QDx5) | 100 (ip) | 0 | 3 | 7 | 0 | 99 (15) | 4.4 |
| B16 (QDx10) | 70 (iv) | 2 | 0 | 8 | 5 | 99 (15) | >4.4 |
| B16 (QDx10) | 50 (iv) | 0 | 1 | 9 | 7 | 99 (15) | >4.4 |
| B16 (QDx10) | 30 (iv) | 0 | 2 | 1 | 1 | 79 (14) | 1.7 | ns of cyclin-dependent kinase2/A revealed how these proteins effectively inhibit
INHIBITORS OF CYCLIN-DEPENDENT KINASES, COMPOSITIONS AND USES RELATED THERETO

I. PRIORITY INFORMATION

This application claims the benefit of U.S. Application No. 60/460,921, filed Apr. 7, 2003, and U.S. Application No. 60/531,872, filed Dec. 23, 2003, the specifications of each of which are incorporated by reference herein.

II. FIELD OF THE INVENTION

This invention relates generally to compounds useful as cyclin-dependent kinase (cdk) inhibitors, pharmaceutical compositions comprising the same, methods for formulating or using the same for treating cancer, or proliferative or other diseases, and intermediates and processes for making the same.

III. BACKGROUND OF THE INVENTION

One of the most important and fundamental processes in biology is the division of cells mediated by the cell cycle. This process ensures the controlled production of subsequent generations of cells with defined biological function. It is a highly regulated phenomenon and responds to a diverse set of cellular signals both within the cell and from external sources. A complex network of tumor promoting and suppressing gene products are key components of this cellular signaling process. Over expression of the tumor-promoting components or the subsequent loss of the tumor-suppressing products will lead to unregulated cellular proliferation and the generation of tumors (Pardee, Science 246:603-608, 1989). Cyclin-dependent kinases play a key role in regulating the cell cycle machinery. These complexes consist of two components: a catalytic subunit (the kinase) and a regulatory subunit (the cyclin). To date, nine kinase subunits (cyclin-dependent kinase 1-9) have been identified along with several regulatory subunits (cyclins A-H, K, N, and T). Each kinase associates with a specific regulatory partner and together make up the active catalytic moiety. Each transition of the cell cycle is regulated by a particular cyclin-dependent kinase complex: G1/S by cyclin-dependent kinase2/cyclin E, cyclin-dependent kinase4/cyclin D1 and cyclin-dependent kinase6/cyclinD2; S/G2 by cyclin-dependent kinase2/cyclin A and cyclin-dependent kinase1/cyclin A; G2/M by cyclin-dependent kinase1/cyclinD. The coordinated activity of these kinases guides the individual cells through the replication process and ensures the vitality of each subsequent generation (Sherr, Cell 73:1059-1065, 1993; Draetta, Trends Biochem. Sci. 15:378-382, 1990).

An increasing body of evidence has shown a link between tumor development and cyclin-dependent kinase related malfunctions. Overexpression of the cyclin regulatory proteins and subsequent kinase hyperactivity have been linked to several types of cancers (Jiang, Proc. Natl. Acad. Sci. USA 90:9026-9030, 1993; Wang, Nature 343:555-557, 1990). More recently, endogenous, highly specific protein inhibitors of cyclin-dependent kinases were found to have a major affect on cellular proliferation (Kamb et al., Science 264:436-440, 1994; Beach, Nature 336:701-704, 1993). These inhibitors include p16INK4 (an inhibitor of cyclin-dependent kinase4/D1), p21CIP1 (a general cyclin-dependent kinase inhibitor), and p27KIP1 (a specific cyclin-dependent kinase2/E inhibitor). A recent crystal structure of p27 bound to cyclin-dependent kinase2/A revealed how these proteins effectively inhibit the kinase activity through multiple interactions with the cyclin-dependent kinase complex (Pavletich, Nature 382:325-331, 1996). These proteins help to regulate the cell cycle through specific interactions with their corresponding cyclin-dependent kinase complexes. Cells deficient in these inhibitors are prone to unregulated growth and tumor formation. This body of evidence has led to an intense search for small molecule inhibitors of the cdk family as therapeutic agents.

IV. SUMMARY OF THE INVENTION

The present invention describes compounds that are potent inhibitors of the class of enzymes known as cyclin-dependent kinases. The present invention provides methods of treating cancer, or other proliferative or other diseases by administering a therapeutically effective amount of at least one of the compounds of the present invention or an isomeric, prodrug, tautomeric, pharmaceutically acceptable salt, N-oxide or stereoisomeric form thereof. The present invention further provides methods of treating cancer, or other proliferative or other diseases by administering a therapeutically effective combination of at least one of the compounds of the invention and another anti-cancer or anti-proliferative agent.

In certain embodiments, the invention contemplates a compound, or an isomeric, prodrug, tautomeric, pharmaceutically acceptable salt, N-oxide, or stereoisomeric form thereof, having a structure of Formula II:

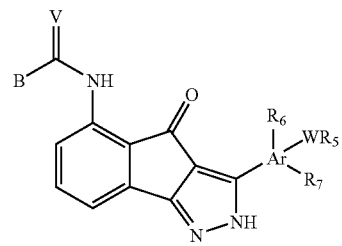

wherein
B represents $M_nR_8$;
Ar represents an aryl or heteroaryl ring;
V represents O, S, or N—CN;
W represents O, S, or NR";
R' represents, independently for each occurrence, H, lower alkyl, or a metal counterion;
R" represents, independently for each occurrence, H or lower alkyl;
$R_5$ represents H, $P(=O)(OR')_2$, or $M_nQ$;
$R_6$ represents H, OH, or $M_nQ$, provided that only one of $R_5$ and $R_6$ represents H;
$R_7$ represents H, halogen, hydroxyl, lower alkyl or lower alkoxyl;
$R_8$ represents substituted or unsubstituted alkyl, alkenyl, alkynyl, alkoxy, aryl, heteroaryl, cyclo-alkyl, heterocyclyl, or amine;
M, independently for each occurrence, represents a substituted or unsubstituted methylene group (including C(=O) and C(=S)), NR", O, S, S(O), or $S(O_2)$;
n represents an integer from 1-4 when present in B, from 0-6 when present in $R_5$ and from 1-3 when present in $R_6$; and
Q represents a substituted or unsubstituted: tertiary amino substituent, or nitrogen-containing heterocycle.

In certain embodiments $R_8$ represents substituted or unsubstituted morpholino, piperazinyl, or cyclohexyl.

In certain embodiments R" represents H.

In certain embodiments $R_5$ represents $M_nQ$.

In certain embodiments the occurrence of M attached to Q represents $CH_2$, $S(O_2)$, $C(=S)$, or $C(=O)$.

In certain embodiments the occurrence of M attached to Q represents $CH_2$.

In certain embodiments the occurrence of M attached to Q is $C(=O)$.

In certain embodiments the occurrence of M attached to Q represents substituted NR".

In certain embodiments Q represents a substituted or unsubstituted nitrogen-containing heterocycle.

In certain embodiments Q represents a substituted or unsubstituted tertiary amino group.

In certain embodiments $R_8$ represents substituted or unsubstituted morpholino, piperazinyl, or cyclohexyl. In certain embodiments R" represents H, while in certain embodiments at least one occurrence of M represents $CH_2$, substituted NR" or, when attached to Q, represents $CH_2$, $S(O_2)$, $C(=S)$, or $C(=O)$.

In certain embodiments Q represents a substituted or unsubstituted nitrogen-containing heteroaryl ring. In certain other embodiments Q represents a substituted or unsubstituted nitrogen-containing heterocycle. In certain embodiments Q represents a substituted or unsubstituted tertiary amino group. In certain embodiments Q represents a substituted or unsubstituted secondary amino group.

In certain embodiments the invention contemplates a compound, or an isomeric, prodrug, tautomeric, pharmaceutically acceptable salt, N-oxide, or stereoisomeric form thereof, having a structure of Formula II:

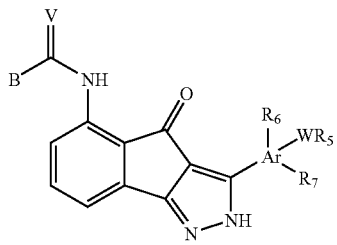

wherein

B represents $M_nR_8$;

Ar represents an aryl or heteroaryl ring;

V represents O, S, or N—CN;

W represents O, S, $S(O_2)$, $C(=O)$, $C(=S)$, $CH_2$, or NR";

R' represents, independently for each occurrence, H, lower alkyl, or a metal counterion;

R" represents, independently for each occurrence, H or lower alkyl;

R'" represents H, or optionally substituted lower alkyl;

$R_5$ represents $M_nJK$;

$R_6$ represents H, OH, or $M_nQ$;

$R_7$ represents H, halogen, hydroxyl, lower alkyl or lower alkoxyl;

$R_8$ represents substituted or unsubstituted alkyl, alkenyl, alkynyl, alkoxy, aryl, heteroaryl, cycloalkyl, heterocyclyl, or amine;

J represents $C(=O)$, $C(=S)$, or $SO_2$;

K represents OR', $N(R")_2$, or $N(R')SO_2R"$;

M, independently for each occurrence, represents a substituted or unsubstituted methylene group (including $C(=S)$ and $C(=O)$), NR", O, S, S(O), or $S(O_2)$;

n represents an integer from 1-7 when present in B, from 0-6 when present in $R_5$ and from 1-3 when present in $R_6$; and Q represents a substituted or unsubstituted: nitrogen-containing heteroaryl ring, secondary amino substituent, tertiary amino substituent, or nitrogen-containing heterocycle.

In certain embodiments $R_8$ represents substituted or unsubstituted morpholino, piperazinyl, or cyclohexyl. In certain embodiments R" represents H.

In certain embodiments, the occurrence of M attached to Q represents $CH_2$, substituted NR", $S(O_2)$, $C(=S)$, or $C(=O)$.

In certain embodiments $R_8$ represents substituted or unsubstituted morpholino, piperazinyl, or cyclohexyl.

In certain embodiments R" represents H.

In certain embodiments $R_5$ represents $M_nQ$.

In certain embodiments the occurrence of M attached to Q represents $CH_2$, $S(O_2)$, $C(=S)$, or $C(=O)$.

In certain embodiments the occurrence of M attached to Q is $C(=O)$.

In certain embodiments the occurrence of M attached to Q represents $CH_2$.

In certain embodiments the occurrence of M attached to Q represents substituted NR".

In certain embodiments Q represents a substituted or unsubstituted tertiary amino substituent.

In certain embodiments Q represents a substituted or unsubstituted nitrogen-containing heterocycle.

In certain embodiments substituents include, independently for each occurrence, alkyl, oxo, acyl amino, hydroxyl, carbonyl, sulfonyl, ester, amide, NR", hydroxy alkyl, alkoxy alkyl, aryl, heterocyclyl, cycloalkyl, or oligo(ethylene glycol).

Certain embodiments include a compound, or an isomeric, prodrug, tautomeric, pharmaceutically acceptable salt, N-oxide, or stereoisomeric form thereof, having a structure of Formula I:

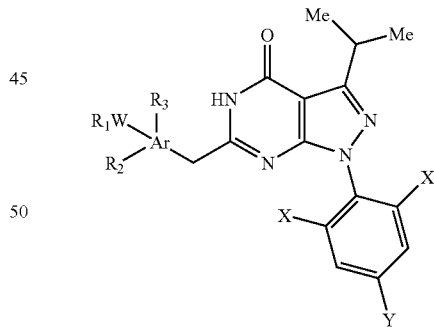

wherein

Ar represents an aryl or heteroaryl ring;

W represents O, or NR";

X represents, independently for each occurrence, methyl or halogen;

Y represents H, X, or a sulfonamide;

R' represents, independently for each occurrence, H, lower alkyl, or a metal counterion;

R" represents, independently for each occurrence, H or lower alkyl;

$R_1$ represents H, $P(=O)(OR')_2$, or $M_nQ$;

$R_2$ represents H, OH, or $M_nQ$, wherein one and only one of $R_1$ and $R_2$ represents H;

$R_3$ represents from 0 to 3 substituents on the ring to which it is attached, selected from halogen, lower alkyl, lower alkoxy, hydroxyl, and $N(R'')_2$;

M, independently for each occurrence, represents a substituted or unsubstituted methylene group (including C(=S) and C(=O)), NR'', O, S, S(O), S(O$_2$);

n represents an integer from 1 to 5; and

Q represents a nitrogen-containing heteroaryl ring, a tertiary amino substituent, or a substituted or unsubstituted nitrogen-containing heterocycle.

In certain embodiments, Q represents a substituted or unsubstituted nitrogen-containing heteroaryl ring. In certain embodiments $R_1W$ and $R_2$ are ortho to each other on Ar but are not ortho to the methylene substituent attached to the bicyclic core. In certain embodiments Ar represents a heteroaryl ring.

In certain embodiments, $R_3$ represents 1-3 substituents on the ring to which it is attached. In certain embodiments, Y represents $S(O_2)N(R'''')_2$, wherein R'''' represents, independently for each occurrence, H, lower alkoxyl, or lower alkyl while, in some embodiments, both occurrences of R'''' taken together with N form a substituted or unsubstituted nitrogen-containing heterocycle.

Certain embodiments include a compound, or isomeric, prodrug, tautomeric, pharmaceutically acceptable salt, N-oxide, or stereoisomeric forms thereof, having the structure of Formula II

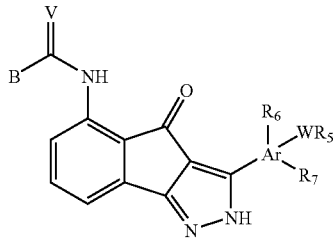

wherein

B represents $M_nR_8$.

Ar represents an aryl or heteroaryl ring;

V represents O, S, or N—CN;

W represents O, S, S(O$_2$), C(=O), C(=S), CH$_2$, or N'';

R' represents, independently for each occurrence, H, lower alkyl, or a metal counterion;

R'' represents, independently for each occurrence, H or lower alkyl;

R''' represents H, or optionally substituted lower alkyl;

$R_5$ represents H, P(=O)(OR')$_2$, $M_nJK$, or $M_nQ$;

$R_6$ represents H, OH, or $M_nQ$, provided that one and only one of $R_5$ and $R_6$ represents H;

$R_7$, independently for each occurrence, represents H, halogen, hydroxyl, lower alkyl, or lower alkoxyl;

$R_8$ represents substituted or unsubstituted alkyl, alkenyl, alkynyl, alkoxy, aryl, heteroaryl, cycloalkyl, heterocyclyl, or amine;

J represents C(=O), C(=S), or SO$_2$;

K represents OR', N(R'')$_2$, or N(R')SO$_2$R'';

M, independently for each occurrence, represents a substituted or unsubstituted methylene group (including C(=O), C(=S)), NR'', O, S, S(O), S(O$_2$), or CH$_2$;

n represents an integer from 1-7 when present in B, from 0-6 when present in $R_5$ and from 1-3 when present in $R_6$; and Q represents a substituted or unsubstituted: nitrogen-containing heteroaryl ring, secondary amino substituent, tertiary amino substituent, or nitrogen-containing heterocycle;

provided that compounds having a structure of Formula IIa are excluded:

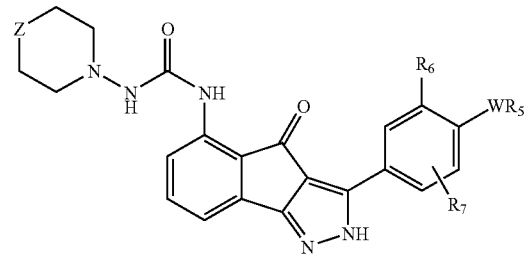

wherein

W and Z, independently, represent O or NR'';

R' represents, independently for each occurrence, H, lower alkyl, or a metal counterion;

R'' represents, independently for each occurrence, H or lower alkyl;

$R_5$ represents H, P(=O)(OR')$_2$, or $M_nQ$;

$R_6$ represents H, OH, or $M_nQ$, provided that one and only one of $R_5$ and $R_6$ represents H;

$R_7$, independently for each occurrence, represents hydrogen, halogen, lower alkyl, or lower alkoxyl;

M, independently for each occurrence, represents a substituted or unsubstituted methylene group (including C(=S) and C(=O)), NR'', O, S, S(O), S(O$_2$);

n represents an integer from 1-5; and

Q represents a nitrogen-containing heteroaryl ring, a tertiary amino substituent, or a substituted or unsubstituted nitrogen-containing heterocycle.

In certain embodiments, Q in Formula IIa represents a tertiary amino substituent, e.g., dialkyl amine. In certain embodiments Q in Formula IIa represents a substituted or unsubstituted nitrogen containing heterocycle such as morpholine, piperidine, piperazine, or pyrrolidine. In certain embodiments, Q represents a nitrogen-containing heteroaryl ring, a tertiary amino substituent, or a substituted or unsubstituted nitrogen-containing heterocycle.

In certain embodiments, in Formula II,

B represents $M_nR_8$;

Ar represents an aryl or heteroaryl ring;

V represents O, S, or N—CN;

W represents C(=O), C(=S), SO$_2$, or CH$_2$;

R' represents, independently for each occurrence, H, lower alkyl, a metal counterion, or alkaline earth metal counterion;

R'' represents, independently for each occurrence, H or lower alkyl;

R''' represents H, or optionally substituted lower alkyl;

$R_5$ represents H, P(=O)(OR')$_2$, $M_nJK$, or $M_nQ$;

$R_6$ represents H, OH, or $M_nQ$, provided that only one of $R_5$ and $R_6$ represents H;

$R_7$ represents H, halogen, hydroxyl, lower alkyl or lower alkoxyl;

$R_8$ represents substituted or unsubstituted alkyl, alkenyl, alkynyl, alkoxy, aryl, heteroaryl, cycloalkyl, heterocyclyl, or amine;

J represents $C(=O)$, $C(=S)$, or $SO_2$;

K represents $OR'$, $N(R'')_2$, or $N(R')SO_2R''$;

M, independently for each occurrence, represents a substituted or unsubstituted methylene group (including $C(=S)$ and $C(=O)$), $NR''$, O, S, $S(O)$, or $S(O_2)$;

n represents an integer from 1-4 when present in B, from 0-6 when present in $R_5$ and from 1-3 when present in $R_6$; and Q represents a substituted or unsubstituted: nitrogen-containing heteroaryl ring, secondary amino substituent, tertiary amino substituent, or nitrogen-containing heterocycle.

In certain embodiments Q represents a tertiary amino substituent, e.g., dialkyl amine, or a substituted or unsubstituted nitrogen containing heterocycle such as morpholine, piperidine, piperazine, or pyrrolidine.

In certain embodiments, in Formula II,

B represents $M_nR_8$;
Ar represents an aryl or heteroaryl ring;
V represents O, S, or N—CN;
W represents O, S, $S(O_2)$, $C(=O)$, $C(=S)$, $CH_2$, or $NR''$;
R' represents, independently for each occurrence, H, lower alkyl, a metal counterion, or alkaline earth metal counterion;
R'' represents, independently for each occurrence, H or lower alkyl;
R''' represents H, or optionally substituted lower alkyl;
$R_5$ represents H, $P(=O)(OR')_2$, $M_nJK$, or $M_nQ$;
$R_6$ represents H, OH, or $M_nQ$, provided that only one of $R_5$ and $R_6$ represents H;
$R_7$ represents H, halogen, hydroxyl, lower alkyl or lower alkoxyl;
$R_8$ represents substituted or unsubstituted alkyl, alkenyl, alkynyl, alkoxy, aryl, heteroaryl, cycloalkyl, heterocyclyl, or amine;
J represents $C(=O)$, $C(=S)$, or $SO_2$;
K represents $OR'$, $N(R'')_2$, or $N(R')SO_2R''$;
M, independently for each occurrence, represents a substituted or unsubstituted methylene group (including $C(=S)$ and $C(=O)$), $NR''$, O, S, $S(O)$, or $S(O_2)$;
n represents an integer from 1-4 when present in B, from 0-6 when present in $R_5$ and from 1-3 when present in $R_6$; and
Q represents a substituted or unsubstituted secondary amino substituent.

In other embodiments, in Formula II,

B represents $M_nR_8$;
Ar represents an aryl or heteroaryl ring;
V represents O, S, or N—CN;
W represents O, S, $S(O_2)$, $C(=O)$, $C(=S)$, $CH_2$, or $NR''$;
R' represents, independently for each occurrence, H, lower alkyl, a metal counterion, or alkaline earth metal counterion;
R'' represents, independently for each occurrence, H or lower alkyl;
R''' represents H, or optionally substituted lower alkyl;
$R_5$ represents $M_nJK$, provided that $R_5$ is not $CH_2COOH$;
$R_6$ represents H, OH, or $M_nQ$;
$R_7$ represents H, halogen, hydroxyl, lower alkyl or lower alkoxyl;
$R_8$ represents substituted or unsubstituted alkyl, alkenyl, alkynyl, alkoxy, aryl, heteroaryl, cyclo-alkyl, heterocyclyl, or amine;
J represents $C(=O)$, $C(=S)$, or $SO_2$;
K represents $OR'$, $N(R'')_2$, or $N(R')SO_2R''$;
M, independently for each occurrence, represents a substituted or unsubstituted methylene group (including $C(=S)$ and $C(=O)$), $NR''$, O, S, $S(O)$, or $S(O_2)$;
n represents an integer from 1-4 when present in B, from 0-6 when present in $R_5$ and from 1-3 when present in $R_6$; and
Q represents a substituted or unsubstituted: nitrogen-containing heteroaryl ring, secondary amino substituent, tertiary amino substituent, or nitrogen-containing heterocycle.

In certain embodiments, in Formula II, Q is a substituted or unsubstituted nitrogen-containing heteroaryl ring, while $R_8$ may represent substituted or unsubstituted morpholino, piperazinyl, or cyclohexyl. In Formula II, R'' may represent H.

M may also represent $CH_2$. In certain embodiments, in Formula II, W represents $CH_2$ and at least one occurrence of M represents substituted $NR''$.

In certain embodiments, in Formula II, Q represents a substituted or unsubstituted secondary amino group. In certain embodiments, in Formula II, Q represents a substituted or unsubstituted tertiary amino group. In certain embodiments, in Formula II, Q represents a substituted or unsubstituted nitrogen-containing heterocycle.

In certain embodiments, in Formula II, Q represents a substituted or unsubstituted: nitrogen-containing heteroaryl ring, tertiary amino substituent, or nitrogen-containing heterocycle.

In certain embodiments in Formula II, $R_5$ represents $M_nQ$ and Q represents a substituted or unsubstituted: nitrogen-containing heteroaryl ring, tertiary amino substituent, or nitrogen-containing heterocycle.

In certain embodiments in Formula II, Q represents a substituted or unsubstituted tertiary amino group.

In certain embodiments in Formula II, Q represents a substituted or unsubstituted nitrogen-containing heterocycle.

In certain embodiments in Formula II, $R_5$ represents $M_nQ$ and Q represents a substituted or unsubstituted secondary amino group.

In certain embodiments in Formula II, $R_5$ represents $M_nQ$ and Q is a substituted or unsubstituted nitrogen-containing heteroaryl ring.

In certain embodiments in Formula II, $R_8$ represents substituted or unsubstituted morpholino, piperazinyl, or cyclohexyl.

In certain embodiments in Formula II, R'' represents H.

In certain embodiments in Formula II, W represents $CH_2$.

In certain embodiments in Formula II, M when attached to Q is $CH_2$, $S(O_2)$, $C(=S)$, or $C(=O)$.

In certain embodiments in Formula II, M when attached to Q is $CH_2$.

In certain embodiments, in Formula II, the occurrence of M attached to Q is $CH_2$, $S(O_2)$, $C(=S)$, or $C(=O)$.

In certain embodiments, in Formula II, V is O, M represents NH, and $R_8$ has the structure:

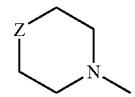

where Z represents O or NR''.

In certain embodiments, AR represents a phenyl ring and $R_6$ and $R_7$ represent H for all occurrences.

Certain embodiments include a compound, or a prodrug, isomeric, tautomeric, pharmaceutically acceptable salt, N-oxide, or stereoisomeric form thereof, having a structure of Formula V:

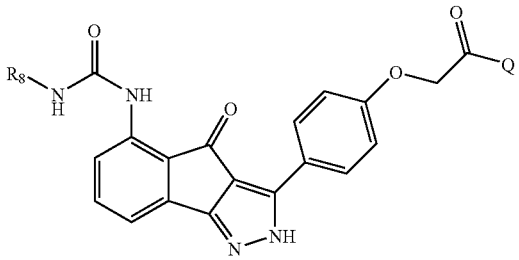

wherein
$R_8$ represents a substituted or unsubstituted heterocycle;
Q represents a substituted or unsubstituted: secondary amino substituent, tertiary amino substituent, or substituted or unsubstituted nitrogen-containing heterocycle.

As noted above, $R_8$ may represent a morpholino or piperazinyl ring in certain embodiments.

In certain embodiments, as noted above, Q may represent piperazine, morpholine, piperidine, pyridine, pyrrole, oxazole, isoxazole, imidazole, or pyrazole.

Certain embodiments include compounds selected from the group of A34, A36, A37, A44, A46, and A76 to A82, or prodrugs, isomers, tautomers, pharmaceutically acceptable salts, N-oxides, or stereoisomeric forms thereof.

Certain embodiments include compounds selected from the group of A47, A49, A51 and A82, or prodrugs, isomers, tautomers, pharmaceutically acceptable salts, N-oxides, or stereoisomeric forms thereof.

Certain embodiments include a compound, or an isomeric, prodrug, tautomeric, pharmaceutically acceptable salt, N-oxide, or stereoisomeric forms thereof, having a structure of Formula I:

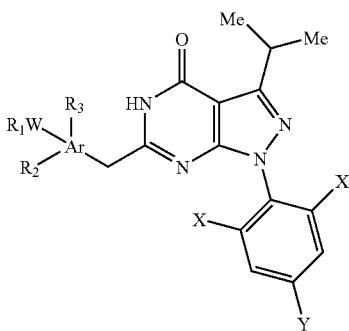

wherein
Ar represents an aryl or heteroaryl ring;
W represents O, $S(O_2)$, $C(=O)$, $C(=S)$, S, $CH_2$, or NR";
X represents, independently for each occurrence, methyl or halogen;
Y represents H, X, or a sulfonamide;
R' represents, independently for each occurrence, H, lower alkyl, or a metal counterion;
R" represents, independently for each occurrence, H or lower alkyl;
$R_1$ represents H, $P(=O)(OR')_2$, or $M_nQ$;
$R_2$ represents H, OH, or $M_nQ$, wherein one and only one of $R_1$ and $R_2$ represents H;
$R_3$ represents from 0 to 3 substituents on the ring to which it is attached, selected from halogen, lower alkyl, lower alkoxy, hydroxyl, and $N(R")_2$;
M, independently for each occurrence, represents a substituted or unsubstituted methylene group (including $C(=S)$ and $C(=O)$), NR", O, S, S(O), $S(O_2)$;
n represents an integer from 1 to 5; and
Q represents a substituted or unsubstituted: secondary amino substituent, tertiary amino substituent, or nitrogen-containing heterocycle;
provided that compounds having the structure of Formula Ia are excluded:

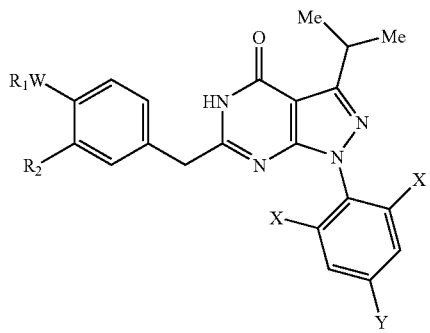

wherein
W represents O or NR";
X represents, independently for each occurrence, a halogen;
Y represents H or X;
R' represents, independently for each occurrence, H, lower alkyl, or a metal counterion;
R" represents, independently for each occurrence, H or lower alkyl;
$R_1$ represents H, $P(=O)(OR')_2$, or $M_nQ$;
$R_2$ represents H, OH, or $M_nQ$, provided that one and only one of $R_1$ and $R_2$ represents H;
M, independently for each occurrence, represents a substituted or unsubstituted methylene group (including $C(=S)$ and $C(=O)$), NR", O, S, S(O), or $S(O_2)$;
n represents an integer from 1 to 5; and
Q represents a tertiary amino substituent.

In certain embodiments, Q in Formula Ia represents a tertiary amino substituent, e.g., dialkyl amine. In certain embodiments Q in Formula Ia represents a substituted or unsubstituted nitrogen containing heterocycle such as morpholine, piperidine, piperazine, or pyrrolidine. In certain embodiments, Q represents a nitrogen-containing heteroaryl ring, a tertiary amino substituent, or a substituted or unsubstituted nitrogen-containing heterocycle.

In certain embodiments, in Formula I,
Ar represents an aryl or heteroaryl ring;
W represents O, $S(O_2)$, $C(=O)$, $C(=S)$, $CH_2$, S, or NR";
X represents, independently for each occurrence, methyl or halogen;
Y represents H, X, or a sulfonamide;
R' represents, independently for each occurrence, H, lower alkyl, or a metal counterion;
R" represents, independently for each occurrence, H or lower alkyl;
$R_1$ represents H, $P(=O)(OR')_2$, or $M_nQ$;

R$_2$ represents H, OH, or M$_n$Q, wherein one and only one of R$_1$ and R$_2$ represents H;

R$_3$ represents from 0 to 3 substituents on the ring to which it is attached, selected from halogen, lower alkyl, lower alkoxy, hydroxyl, and N(R")$_2$;

M, independently for each occurrence, represents a substituted or unsubstituted methylene group (including C(=S) and C(=O)), NR", O, S, S(O), S(O$_2$);

n represents an integer from 1 to 5; and

Q represents a substituted or unsubstituted: secondary amino substituent, or nitrogen-containing heteroaryl ring.

In certain embodiments, in Formula I,

Ar represents an aryl or heteroaryl ring;

W represents S(O$_2$), C(=O), C(=S), or CH$_2$;

X represents, independently for each occurrence, methyl or halogen;

Y represents H, X, or a sulfonamide;

R' represents, independently for each occurrence, H, lower alkyl, or a metal counterion;

R" represents, independently for each occurrence, H or lower alkyl;

R$_1$ represents H, P(=O)(OR')$_2$, or M$_n$Q;

R$_2$ represents H, OH, or M$_n$Q, wherein one and only one of R$_1$ and R$_2$ represents H;

R$_3$ represents from 0 to 3 substituents on the ring to which it is attached, selected from halogen, lower alkyl, lower alkoxy, hydroxyl, and N(R")$_2$;

M, independently for each occurrence, represents a substituted or unsubstituted methylene group (including C(=S) and C(=O)), NR", O, S, S(O), or S(O$_2$);

n represents an integer from 1 to 5; and

Q represents a substituted or unsubstituted: nitrogen-containing heteroaryl ring, tertiary amino substituent, secondary amino substituent, or nitrogen-containing heterocycle.

In certain embodiments W represents O, S(O$_2$), C(=O), C(=S), S, CH$_2$, or NR".

In certain embodiments, in Formula I, W is CH$_2$.

In certain embodiments, in Formula I, R$_1$W and R$_2$ are ortho to each other on Ar but are not ortho to the methylene substituent attached to the bicyclic core.

In certain embodiments, in Formula I, Ar represents a heteroaryl ring.

In certain embodiments, in Formula I, R$_3$ represents 1-3 substituents on the ring to which it is attached.

In certain embodiments, in Formula I, Y has the form S(O$_2$)N(R"")$_2$, wherein R"" represents, independently for each occurrence, H, lower alkoxyl, or lower alkyl, while in certain of such embodiments, both occurrences of R"" taken together with N form a substituted or unsubstituted nitrogen-containing heterocycle.

As noted previously, in certain embodiments Q represents a substituted or unsubstituted: nitrogen-containing heteroaryl ring, tertiary amino substituent, or nitrogen-containing heterocycle.

In certain embodiments, suitable substituents may include, independently for each occurrence, alkyl, oxo, acyl amino, hydroxyl, carbonyl, sulfonyl, ester, amide, NR", hydroxy alkyl, alkoxy alkyl, aryl, heterocyclyl, cycloalkyl, or oligo (ethylene glycol). In certain embodiments, where Q represents a secondary amino substituent, suitable substituents include alkyl, alkoxyalkyl, hydroxylakly, and hydroxyalkoxyalkyl. Those skilled in the art will readily recognize that the list of enumerated substituents is not exhaustive, and many other suitable substituents may be used.

Certain embodiments may include pharmaceutical compositions comprising a pharmaceutically acceptable excipient and a compound of any of the type disclosed herein, while certain embodiments include a method of treating a hyperproliferative disorder, comprising administering to an animal a compound of any of the type disclosed herein.

In certain embodiments, the compounds disclosed herein may be applied to methods of inhibiting proliferation of a cell, comprising contacting the cell with a compound of the type disclosed herein, or to methods of treating a viral infection (such as infection caused by a human immunodeficiency virus (HIV)), comprising administering to a mammal a compound of the type disclosed herein. Certain embodiments contemplate methods for the treatment or prevention of alopecia induced by chemotherapy or radiation therapy, comprising administering to a mammal a compound of the type disclosed herein conjointly with one or more chemotherapeutics or radiation therapy. The compounds disclosed herein may also be used for the manufacture of a medicament.

In certain embodiments, the present invention provides a novel pharmaceutical composition comprising a pharmaceutically acceptable carrier and a therapeutically effective amount of a compound of formula (I), (II), or (III), or any other compound disclosed herein, or an isomeric, prodrug, tautomeric, pharmaceutically acceptable salt, N-oxide or stereoisomeric form thereof.

In another embodiment, the present invention provides a novel method of treating cancer, or other proliferative or other diseases comprising administering to a host in need of such treatment a therapeutically effective amount of a compound of formula (I), (II), or (III), or any other compound disclosed herein, or an isomeric, prodrug, tautomeric, pharmaceutically acceptable salt, N-oxide or stereoisomeric form thereof.

In another embodiment, the present invention provides a novel method of treating cancer, or other proliferative or other diseases comprising administering to a host in need of such treatment a therapeutically effective amount of: (a) a compound of formula (I), (II), or (III), or any other compound disclosed herein, or an isomeric, prodrug, tautomeric, pharmaceutically acceptable salt, N-oxide or stereoisomeric form thereof; and (b) at least one compound selected from anticancer agents and anti-proliferative agents.

As described herein, the inhibitors of this invention are capable of inhibiting the cell-cycle machinery and consequently would be useful in modulating cell-cycle progression, which would ultimately control cell growth and differentiation. Such compounds would be useful for treating subjects having disorders associated with excessive cell proliferation, such as cancer, psoriasis, immunological disorders involving unwanted leukocyte proliferation, in the treatment of restenosis and other smooth muscle cell disorders, and the like. Such compounds would also be useful in the inhibition of human immunodeficiency virus type I (HIV-I) transcription (Wang et al., J. Virology 75:7266-7279 (2001).

Also described herein, the compounds of this invention may be used in the manufacture of a medicament, which can be used to treat diseases such as those discussed herein.

V. BRIEF DESCRIPTION OF THE DRAWINGS

FIG. 1 shows effects of exposure of compound A37 on.

FIG. 5 presents results obtained from the HCT-116 xenograft tumor assay with various compounds of the invention.

Figures 6A, 6B:
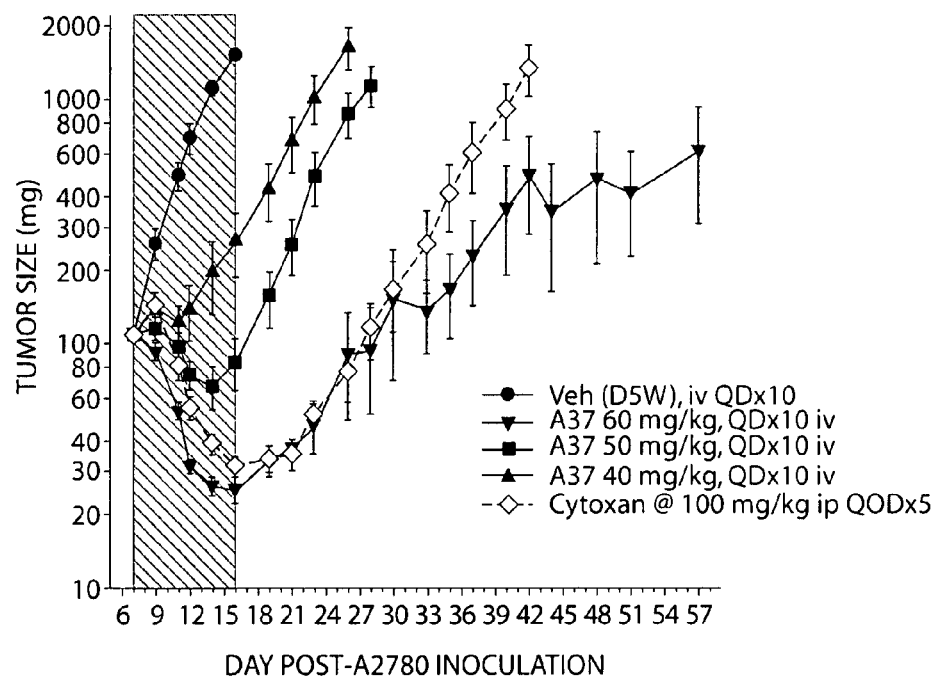

FIG. 6 shows the results obtained from the A2780 xenograft tumor assay with compound A37, represented by (FIG. 6A) time-course of tumor size at various doses; and (FIG. 6B) table of salient metrics from the assay.

Figures 7A, 7B:
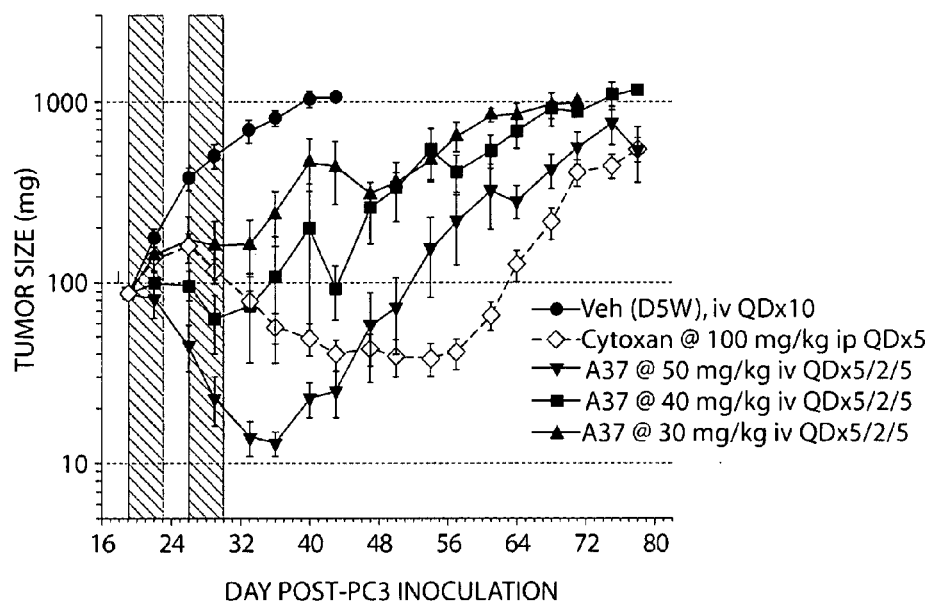

FIG. 7 shows the results obtained from the PC3 xenograft tumor assay with compound A37, represented by (FIG. 7A) time-course of tumor size at various doses; and (FIG. 7B) table of salient metrics from the assay.

Figures 8A, 8B:
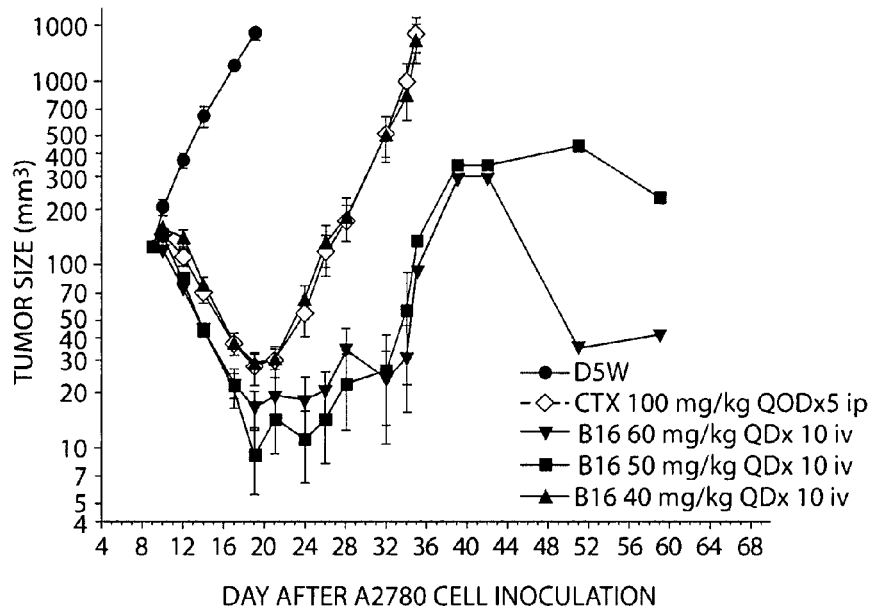

FIG. 8 shows the results obtained from the A2780 xenograft tumor assay with compound B16, represented by (FIG. 8A) time-course of tumor size at various doses; and (FIG. 8B) table of salient metrics from the assay.

Figure 9:
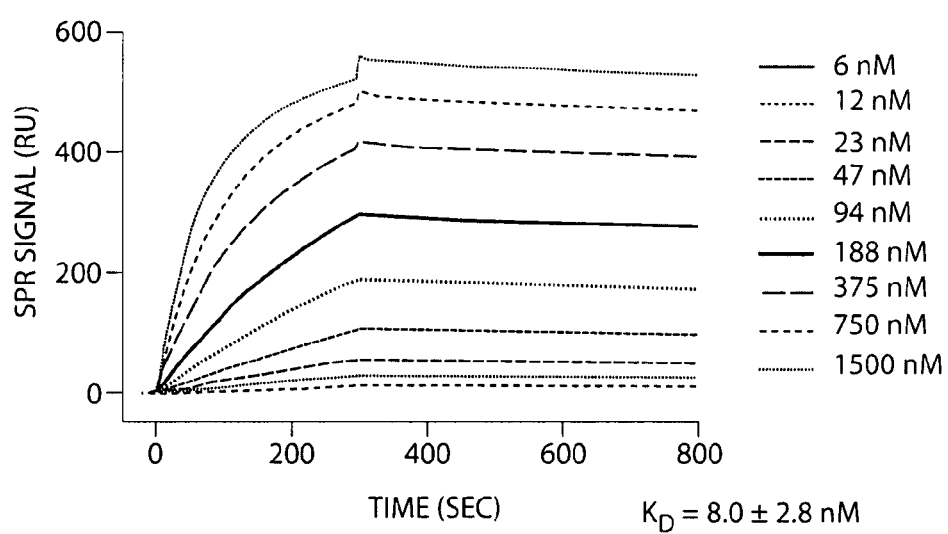

FIG. 9 shows as an example the results obtained for the binding of CDK2/cyclinE to the CM5-inhibitor-loaded chip. The $K_D$ calculated from these data amounts to 8.0+/−2.8 nM.

VI. DETAILED DESCRIPTION OF EXEMPLARY EMBODIMENTS

The invention pertains to novel cyclin dependent kinase inhibitors (cdks) and specifically, but not exclusively, as inhibitors of cdk/cyclin complexes. As described herein, the inhibitors of this invention are capable of inhibiting the cell-cycle machinery and consequently may be useful in modulating cell-cycle progression, ultimately controlling cell growth and differentiation. Such compounds would be useful for treating subjects having disorders associated with excessive cell proliferation, such as the treatment of cancer, psoriasis, immunological disorders involving unwanted leukocyte proliferation, in the treatment of restenosis and other smooth muscle cell disorders, and the like, as discussed in greater detail below.

In one embodiment, the present invention provides compounds, including isomeric, prodrug, tautomeric, pharmaceutically acceptable salt, N-oxide, or stereoisomeric forms thereof, having a structure of Formula I:

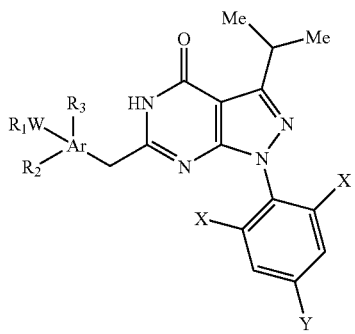

wherein
Ar represents an aryl or heteroaryl ring, such as a phenyl or pyrrole ring;
W represents O, S(O$_2$), C(=O), C(=S), CH$_2$, S, or NR";
X represents, independently for each occurrence, methyl or halogen, such as F, Cl, Br, or I, preferably Cl;
Y represents H, X, or a sulfonamide;
R' represents, independently for each occurrence, H, lower alkyl, or a metal counterion, such as an alkali or alkaline earth metal counterion;
R" represents, independently for each occurrence, H or lower alkyl, preferably Me;
$R_1$ represents H, P(=O)(OR')$_2$, or M$_n$Q;
$R_2$ represents H, OH, or M$_n$Q, preferably provided that one and only one of $R_1$ and $R_2$ represents H;
$R_3$ represents from 0 to 3 substituents on the ring to which it is attached, preferably selected from halogen, lower alkyl, lower alkoxy, hydroxyl, and N(R")$_2$;
M, independently for each occurrence, represents a substituted or unsubstituted methylene group (e.g., substituted with lower alkyl, oxo, hydroxyl, etc., may also include C(=S) and C(=O)), NR", O, S, S(O), or S(O$_2$), preferably CH$_2$, or, when attached to W or Q, CH$_2$, S(O$_2$), C(=S), or C(=O);
n represents an integer from 1 to 5, preferably from 2 to 4 when present in $R_1$ and from 1-3 when present in $R_2$; and
Q represents a nitrogen-containing heteroaryl ring, e.g., pyrrole, oxazole, isoxazole, imidazole, or pyrazole, a secondary amino substituent, a tertiary amino substituent, e.g., a dialkylamine, or a substituted or unsubstituted nitrogen-containing heterocycle such as morpholine, piperidine, piperazine, or pyrrolidine.

In certain embodiments, Q represents a nitrogen-containing heteroaryl ring, e.g., pyrrole, oxazole, isoxazole, imidazole, or pyrazole, a tertiary amino substituent, e.g., a dialkylamine, or a substituted or unsubstituted nitrogen-containing heterocycle such as morpholine, piperidine, piperazine, or pyrrolidine. In certain embodiments Q represents a substituted or unsubstituted secondary amino substituent. In certain such embodiments, the substituent on the secondary amino substituent is selected from alkyl, alkoxyalkyl, hydroxyalkyl, and hydroxyalkoxyalkyl.

In preferred embodiments, $R_1W$ and $R_2$ are adjacent (ortho) to each other on Ar, and are preferably not adjacent (ortho) to the methylene substituent attached to the bicyclic core. In certain embodiments, Ar represents a heteroaryl ring. In some embodiments $R_3$ represents 1-3 substituents on the ring to which it is attached.

In certain embodiments, appropriate substituents include, independently for each occurrence, alkyl, oxo, hydroxyl, alkoxy, hydroxy-alkoxy, carbonyl, sulfonyl, ester, amide, NR", alkyl halide, acyl amino, or substituted or unsubstituted aryl, heteroaryl, heterocyclyl, cycloalkyl, oligo(ethylene glycol) etc. It will be apparent to those skilled in the art that aryl and heteroaryl may employ any suitable substituent, including any of those listed above.

In certain embodiments, W represents O or NR". In certain embodiments W is CH$_2$. In certain other embodiments, W represents O, S(O$_2$), C(=O), C(=S), S, or NR".

In certain embodiments, X represents, independently for each occurrence, halogen, such as F, Cl, Br, or I, preferably Cl. In some embodiments Y represents H or X.

In certain embodiments, Y is a sulfonamide, e.g., of the form S(O$_2$)N(R"")$_2$, wherein R"" represents, independently for each occurrence, H, lower alkoxyl, or lower alkyl, or both occurrences of R"" taken together with N form a substituted or unsubstituted nitrogen-containing heterocycle, e.g., piperazine, morpholine, piperidine, pyridine, etc. In such embodiments, suitable substituents include substituted or unsubstituted occurrences of alkyl, alkoxyl, amino-alkyl, aryl (e.g., phenyl), aralkyl (e.g., benzyl), and heteroaryl.

In certain embodiments of compounds having a structure of Formula I, the present invention provides compounds, including isomeric, prodrug, tautomeric, pharmaceutically acceptable salt, N-oxide, or stereoisomeric forms thereof, having a structure of Formula Ia:

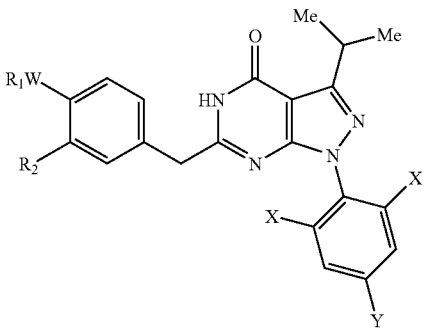

wherein
W represents O or NR";
X represents, independently for each occurrence, a halogen, such as F, Cl, Br, or I, preferably Cl;
Y represents H or X;
R' represents, independently for each occurrence, H, lower alkyl, or a metal counterion, such as an alkali or alkaline earth metal counterion;
R" represents, independently for each occurrence, H or lower alkyl, preferably Me;
$R_1$ represents H, P(=O)(OR')$_2$, or $M_nQ$;
$R_2$ represents H, OH, or $M_nQ$, preferably provided that one and only one of $R_1$ and $R_2$ represents H;
M, independently for each occurrence, represents a substituted or unsubstituted methylene group (e.g., substituted with lower alkyl, oxo, hydroxyl, etc.), NR", O, S, S(O), or S(O$_2$), preferably CH$_2$, or, when attached to W or Q, CH$_2$, S(O$_2$), C(=S), or C(=O);
n represents an integer from 1 to 5, preferably from 2 to 4 when present in $R_1$ and from 1-3 when present in $R_2$; and
Q represents a nitrogen-containing heteroaryl ring, e.g., pyrrole, oxazole, isoxazole, imidazole, or pyrazole, a tertiary amino substituent, e.g., a dialkylamine, or a substituted or unsubstituted nitrogen-containing heterocycle such as morpholine, piperidine, piperazine, or pyrrolidine.

In certain embodiments, Q represents a tertiary amino substituent, e.g., dialkyl amine. In certain embodiments Q represents a substituted or unsubstituted nitrogen containing heterocycle such as morpholine, piperidine, piperazine, or pyrrolidine. In certain embodiments, Q represents a nitrogen-containing heteroaryl ring, a tertiary amino substituent, or a substituted or unsubstituted nitrogen-containing heterocycle.

In certain embodiments, W represents O.

Exemplary compounds according to Formula I and Formula Ia include those shown in Table A.

In one embodiment, the present invention provides compounds having a structure selected from A1, A2, A4, A5, A30, A32, A38, A39, A42, A48, A50, A52 to A55, A58 to A64, A66, A67, C3 and C4, including isomeric, prodrug, tautomeric, pharmaceutically acceptable salt, N-oxide, or stereoisomeric forms thereof.

In certain embodiments, compounds with the structure of Formula I do not include compounds with the structure of Formula Ia.

In another embodiment, the present invention also provides compounds, including isomeric, prodrug, tautomeric, pharmaceutically acceptable salt, N-oxide, or stereoisomeric forms thereof, having a structure of Formula II:

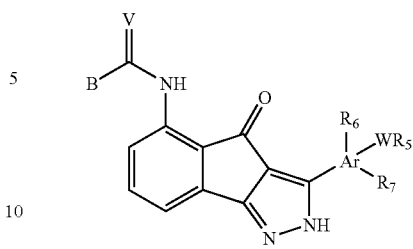

wherein
B represents $M_nR_8$.
Ar represents an aryl or heteroaryl ring, such as a phenyl ring;
V represents O, S, or N—CN, preferably O or S;
W represents O, S, S(O$_2$), C(=O), C(=S), CH$_2$, or NR";
R' represents, independently for each occurrence, H, lower alkyl, or a metal counterion, such as an alkali or alkaline earth metal counterion;
R" represents, independently for each occurrence, H or lower alkyl, preferably H;
R'" represents H, or optionally substituted lower alkyl, preferably with a substituent selected from ester, amide, acylamino, or acyloxy;
$R_5$ represents H, P(=O)(OR')$_2$, $M_nJK$, or $M_nQ$;
$R_6$ represents H, OH, or $M_nQ$, preferably provided that one and only one of $R_5$ and $R_6$ represents H;
$R_7$, independently for each occurrence, represents H, halogen, hydroxyl, lower alkyl, such as methyl, or lower alkoxyl, such as methoxy;
$R_8$ represents substituted or unsubstituted alkyl, alkenyl, alkynyl, alkoxy, aryl, heteroaryl, cycloalkyl, heterocyclyl, or amine;
J represents C(=O), C(=S), or SO$_2$;
K represents OR', N(R")$_2$, or N(R')SO$_2$R";
M, independently for each occurrence, represents a substituted or unsubstituted methylene group (e.g., substituted with lower alkyl, oxo, hydroxyl, etc.), NR", O, S, S(O), or S(O$_2$), preferably NR" or CH$_2$, or, when attached to W or Q, CH$_2$, S(O$_2$), C(=S), or C(=O);
n represents an integer from 0-10, preferably 1-7 or even 1-4 when present in B, from 0-6 when present in $R_5$ and from 1-3 when present in $R_6$; and
Q represents a substituted or unsubstituted: nitrogen-containing heteroaryl ring, e.g., pyrrole, tetrazole, oxazole, oxadiazole, isoxazole, imidazole, or pyrazole; secondary amino substituent, e.g., monoalkyl amine, arylalkyl amine, heteroarylalkyl amine; tertiary amino substituent, e.g., a dialkylamine; or nitrogen-containing heterocycle such as morpholine, piperidine, piperazine, pyridine, or pyrrolidine.

In certain embodiments, when K represents N(R')SO$_2$R", R" represents lower alkyl.

In certain embodiments where $R_5$ is $M_nJK$, $R_5$ is not CH$_2$COOH.

In certain embodiments, appropriate substituents include, independently for each occurrence, alkyl, oxo, hydroxyl, alkoxy, hydroxy-alkoxy, carbonyl, sulfonyl, ester, amide, NR", alkyl halide, acyl amino, or substituted or unsubstituted aryl, heteroaryl, heterocyclyl, cycloalkyl, oligo(ethylene glycol) etc. It will be apparent to those skilled in the art that aryl and heteroaryl may employ any suitable substituent, including any of those listed above.

In certain embodiments, $R_8$ represents any of the following substituents: alkyl, alkenyl, alkynyl, alkoxy, hydroxylalkoxy, aryl, amine, or heteroaryl. In certain embodiments, any of the aforementioned substituents may, in turn, optionally be substituted by any of the mentioned substituents, or even by halo, —CN, $N_3$, $NO_2$, or haloalkyl. Other suitable substituents may also include, for example, cyclohexyl, =O, carbonyl, sulfonyl, carboxyl, sulfoxyl, amide, heterocycle, ester, or ether.

In certain embodiments, at least one occurrence of M is substituted NR" when attached to $R_8$ and when present in $R_5$.

In certain embodiments, including any of the embodiments above, $R_8$ has the following form:

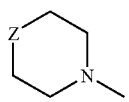

where Z represents O or NR". In certain embodiments $R_8$ represents morpholino or cyclohexyl. In certain such embodiments, $M_n$ is NR", preferably NH. In certain embodiments V is O.

In certain embodiments, W represents $CH_2$. In certain such embodiments, at least one occurrence of M is substituted NR".

In certain embodiments wherein R'" is present and is substituted lower alkyl, the lower alkyl is substituted with from 1-3 (preferably 1) substituents selected from lower alkyl, lower haloalkyl, $NR_8R_{8a}$, $NR"C(O)R_8$, =O, $COR_8$, $CO_2R_8$, $NR"CO_2R_8$, $C(O)NR_8R_{8a}$, $NR"C(O)NR_8R_{8a}$, $NR"C(S)NR_8R_{8a}$, $C(S)NR_8R_{8a}$, $NR"SO_2NR_8R_{8a}$, $SO_2NR_8R_{8a}$, $NR"SO_2R_{8a}$, $SO_2R_{8a}$, $NR"SO_2R_{8a}$, $C_{3-10}$ carbocycle substituted with 0-5 R'", and 5-10-membered heterocycle containing from 1-4 heteroatoms selected from O, N, and S, substituted with 0-3 $R_8$, wherein $R_8$ represents H, $C_{1-4}$ haloalkyl, $NR_{8a}R_{8a}$, $NR"C(O)OR_{8a}$, $NR"C(O)R_{8a}$, $COR_{8a}$, $CO_2R_{8a}$, $CONR_{8a}R_{8a}$, $NHC(O)NR_{8a}R_{8a}$, $NHC(S)NR_{8a}R_{8a}$, $SO_2NR_{8a}R_{8a}$, $SO_2R_{8a}$, $C_{1-4}$ alkyl, phenyl, benzyl, $C_{5-10}$ alkyl substituted with $C_{2-10}$ alkenyl optionally substituted with 0-3 R'", $C_{2-10}$ alkynyl substituted with 0-3 R'", —$(CF_2)_mCF_3$, $C_{3-10}$ carbocycle substituted with 0-5 R'", and 5-10-membered heterocycle containing from 1-4 heteroatoms selected from O, N, and S, substituted with 0-3 R'"; and $R_{8a}$, independently for each occurrence, represents a group selected from H, lower alkyl, phenyl, and benzyl.

In certain embodiments, R'" comprises an amino acid residue, such as a valine or glycine residue, e.g., R'" is a lower alkyl residue substituted with an amino acid residue through an amide or ester linkage.

In preferred embodiments, $R_5W$ and $R_6$ are adjacent (ortho) to each other on Ar, and are preferably not adjacent (ortho) to the bond to the tricyclic core.

In certain embodiments, V represents S or N—CN. In some embodiments, Ar represents a heteroaryl ring.

In certain embodiments of Formula II, W represents O, S or NR". In certain embodiments $R_5$ represents H, P(=O)(OR')$_2$, or $M_nQ$. In certain embodiments $R_7$ represents, independently for each occurrence, halogen, hydroxyl, lower alkyl, such as methyl, or lower alkoxy, such as methoxy. In certain embodiments n represents an integer from 0-5, preferably from 1-5, and more preferably from 2-4 when present in $R_5$.

In certain embodiments of Formula II, W represents O, $CH_2$, C(=O), C(=S), or $SO_2$. In certain embodiments, $R_5$ represents $M_nJK$ or $M_nQ$. In certain embodiments, $R_6$ and $R_7$ represent H. In certain embodiments, M represents C(=O) or $CH_2$. In certain embodiments, n is preferably 1, while in other embodiments n may be 0. In certain embodiments, J is preferably C(=O), and K is OR' or $N(R')SO_2R"$. In certain embodiments, $N(R')SO_2R"$ is $NHSO_2R"$.

In certain embodiments, Q represents a substituted or unsubstituted nitrogen-containing heteroaryl ring. In certain embodiments, Q represents a substituted or unsubstituted heteroaryl ring, e.g., a five-membered or six-membered ring, containing at least two nitrogen atoms. In certain embodiments, Q may be substituted or unsubstituted occurrences of tetrazole or oxadiazole. In certain embodiments Q may be substituted or unsubstituted occurrences of pyridine, piperidine, or piperazine.

In certain embodiments, Q represents a secondary amino substituent. In certain such embodiments, the substituent on the secondary amino substituent is selected from alkyl, alkoxyalkyl, hydroxyalkyl, and hydroxyalkoxyalkyl.

In certain embodiments of Formula II, W represents C(=O), $SO_2$, or C(=S), $R_6$ and $R_7$ represent H, and $R_5$ represents $M_nQ$, where n represents 0 and Q represents a substituted or unsubstituted nitrogen-containing heteroaryl ring. In certain embodiments, W represents $CH_2$, $R_6$ and $R_7$ represent H, and $R_5$ represents $M_nQ$, where n represents 0 and Q represents a substituted or unsubstituted nitrogen-containing heteroaryl ring.

In certain embodiments, W represents S, O, or NR", $R_6$ and $R_7$ represent H, and $R_5$ represents $M_nJK$, where n is an integer from 1-3, J is C(=O), and K is OR' or N(R') $SO_2R"$.

In certain embodiments, W represents S, O, or NR", $R_6$ and $R_7$ represent H, and $R_5$ represents $M_nQ$, where n is an integer from 1-3, and Q is a substituted or unsubstituted five-membered nitrogen-containing heterocycle. In such embodiments, n is preferably 1. In certain embodiments Q contains at least two nitrogen atoms.

In certain embodiments, W represents S, O, or NR", $R_6$ and $R_7$ represent H, and $R_5$ represents $M_nQ$, where n represents an integer from 1-3, and Q is a substituted or unsubstituted six-membered nitrogen-containing heterocycle. In certain of such embodiments, n is 2, and $M_n$ represents $CH_2C$(=O).

In certain embodiments, W represents O, S, or NR", $R_6$ and $R_7$ represent H, and $R_5$ represents $M_nQ$, where M is $CH_2$, n is an integer from 1-3, and Q is a substituted or unsubstituted nitrogen-containing heterocycle.

In certain embodiments, where Q represents a substituted nitrogen-containing heterocycle, e.g., piperazine, morpholine, piperidine, pyridine, thiazole, oxadiazole, tetrazole, pyrrole, etc., suitable substituents include substituted or unsubstituted occurrences of alkyl, amino-alkyl, alkoxyl, aralkyl (e.g., benzyl), aryl (e.g., phenyl), and heteroaryl, e.g., oxazyl, piperazyl, pyridyl, pyrrolyl. In certain such embodiments where Q contains a nitrogen not attached to M, that nitrogen is substituted, e.g., by such a substituent.

In certain embodiments of Formula II, the present invention provides compounds, including isomeric, prodrug, tautomeric, pharmaceutically acceptable salt, N-oxide, or stereoisomeric forms thereof, having a structure of Formula IIa:

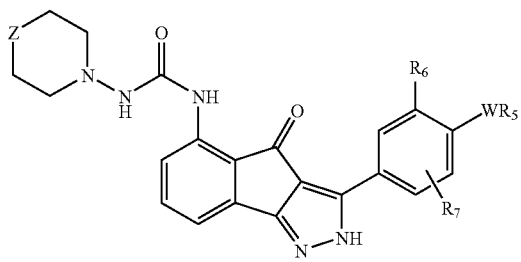

wherein

W and Z, independently, represent O or NR";

R' represents, independently for each occurrence, H, lower alkyl, or a metal counterion, such as an alkali or alkaline earth metal counterion;

R" represents, independently for each occurrence, H or lower alkyl, preferably H;

$R_5$ represents H, $P(=O)(OR')_2$, or $M_nQ$;

$R_6$ represents H, OH, or $M_nQ$, preferably provided that one and only one of $R_5$ and $R_6$ represents H;

$R_7$, independently for each occurrence, represents hydrogen, halogen, lower alkyl, such as methyl, or lower alkoxyl, such as methoxy;

M, independently for each occurrence, represents a substituted or unsubstituted methylene group (e.g., substituted with lower alkyl, oxo, hydroxyl, etc.), NR", O, S, S(O), or $S(O_2)$, preferably $CH_2$, or, when attached to W or Q, $CH_2$, $S(O_2)$, $C(=S)$, or $C(=O)$;

n represents an integer from 1-5, preferably from 2-4 when present in $R_5$ and from 1-3 when present in $R_6$; and Q represents a nitrogen-containing heteroaryl ring, e.g., pyrrole, oxazole, isoxazole, imidazole, or pyrazole, a tertiary amino substituent, e.g., a dialkylamine, or a substituted or unsubstituted nitrogen-containing heterocycle such as morpholine, piperidine, piperazine, or pyrrolidine.

In certain embodiments Q represents a tertiary amino substituent, e.g., dialkyl amine. In certain embodiments Q represents a substituted or unsubstituted nitrogen containing heterocycle such as morpholine, piperidine, piperazine, or pyrrolidine. In certain embodiments, Q represents a nitrogen-containing heteroaryl ring, a tertiary amino substituent, or a substituted or unsubstituted nitrogen-containing heterocycle.

In certain embodiments, compounds with the structure of Formula II do not include compounds with the structure of Formula IIa.

Exemplary compounds of Formula II and Ia include those shown in Table B.

The invention also provides for compounds having a structure selected from A3, A7 to A29, A31, A33 to A37, A40, A41, A44 to A47, A49, A51, A56, A57, A65, A69 to A82, C1, C2, and C5, including isomeric, prodrug, tautomeric, pharmaceutically acceptable salt, N-oxide, or stereoisomeric forms thereof. In a certain embodiments, the invention provides a compound having a structure A37, including isomeric, prodrug, tautomeric, pharmaceutically acceptable salt, N-oxide, or stereoisomeric forms thereof.

In an alternative embodiment, the present invention provides for an isolated prodrug or pharmaceutically acceptable salt of a metabolite of compound A37. A preferred such embodiment is a prodrug or pharmaceutically acceptable salt of compound A68 or C5.

In another embodiment, the present invention provides compounds having a structure selected from B1 to B20, and C1, C2 and C5, including isomeric, prodrug, tautomeric, pharmaceutically acceptable salt, N-oxide, or stereoisomeric forms thereof. In a preferred embodiment, the invention provides a compound having a structure B16 or C5, including isomeric, prodrug, tautomeric, pharmaceutically acceptable salt, N-oxide, or stereoisomeric forms thereof. In another embodiment, the invention provides a compound having a structure B3, including isomeric, prodrug, tautomeric, pharmaceutically acceptable salt, N-oxide, or stereoisomeric forms thereof.

In an alternative embodiment, the present invention provides for an isolated prodrug or pharmaceutically acceptable salt of a metabolite of compound B16. A preferred such embodiment is a prodrug or pharmaceutically acceptable salt of compound B3.

In certain embodiments, the invention provides a compound, or a prodrug, isomeric, tautomeric, pharmaceutically acceptable salt, N-oxide, or stereoisomeric form thereof, having a structure of Formula V:

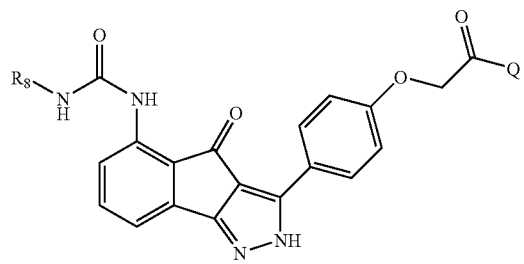

wherein $R_8$ represents a substituted or unsubstituted heterocycle; and

Q represents a substituted or unsubstituted: tertiary amino substituent, or nitrogen-containing heterocycle.

In one embodiment, the present invention provides compounds, including isomeric, prodrug, tautomeric, pharmaceutically acceptable salt, N-oxide, or stereoisomeric forms thereof, having a structure of Formula III:

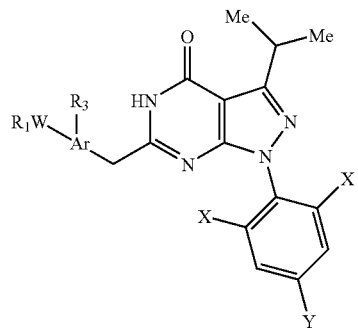

wherein

Ar represents an aryl or heteroaryl ring, such as a phenyl or thiazole ring;

W is absent or represents O, S, $S(O_2)$, $C(=O)$, $C(=S)$, or NR", preferably O;

X represents, independently for each occurrence, methyl or halogen, such as F, Cl, Br, or I, preferably Cl;

Y represents H, X, or a sulfonamide, preferably Cl;

R' represents, independently for each occurrence, H, lower alkyl, or a metal counterion, such as an alkali or alkaline earth metal counterion;

R" represents, independently for each occurrence, H or lower alkyl, preferably Me;

$R_1$ represents lower alkyl or $R_9$O-lower alkyl;

$R_3$ represents from 0 to 3 substituents on the ring to which it is attached, preferably selected from halogen, lower alkyl, lower alkoxy, hydroxyl, and N(R")$_2$; and $R_9$ represents H, lower alkyl, P(=O)(OR')$_2$, alkoxyalkyl, hydroxyalkyl, hydroxyalkoxyalkyl, monoalkyl amine, arylalkyl amine, heteroarylalkyl amine, oligo ethylene glycol, or an amino acid residue, such as an alpha-amino acid residue.

In certain embodiments, Ar represents a five-membered heteroaryl ring, preferably a thiazole, oxazole, or imidazole ring. In certain such embodiments, W is absent, and $R_1$ represents lower alkyl, optionally substituted with $R_9$O.

In certain embodiments, $R_9$ represents H, lower alkyl, P(=O)(OR')$_2$, or an amino acid residue, such as an alpha-amino acid residue. In other embodiments, $R_9$ represents alkoxyalkyl, hydroxyalkyl, hydroxyalkoxyalkyl, monoalkyl amine, arylalkyl amine, heteroarylalkyl amine, or an oligo ethylene glycol.

In certain embodiments, Ar represents a phenyl ring, W represents O, NR", or S (preferably O), and $R_1$ represents lower alkyl, optionally substituted with $R_{9O}$. In certain such embodiments, the lower alkyl group is selected from ethyl, isopropyl, and t-butyl.

In certain preferred embodiments, $R_3$ is absent.

In other embodiments of the invention, the compounds shown in Tables C and D are exemplary, and the invention includes isomeric, prodrug, tautomeric, pharmaceutically acceptable salt, N-oxide, or stereoisomeric forms of the compounds depicted therein.

In another embodiment, the present invention provides a novel pharmaceutical composition comprising a pharmaceutically acceptable carrier and a therapeutically effective amount of a compound of Formula I, Ia, II, Ia, III or any compound disclosed herein, or an isomeric, prodrug, tautomeric, pharmaceutically acceptable salt, N-oxide, or stereoisomeric form thereof. In a preferred embodiment, such pharmaceutical composition comprises a therapeutically effective amount of a compound selected from A1 to A82, B1 to B20 and C1 to C5, or an isomeric, prodrug, tautomeric, pharmaceutically acceptable salt, N-oxide, or stereoisomeric form thereof. In alternative embodiment, such pharmaceutical composition comprises a therapeutically effective amount of a prodrug or pharmaceutically acceptable salt of a metabolite of compound A37 or B16, preferably a metabolite having the structure A68 or C5.

In another embodiment, the present invention provides a novel method of treating cancer, or other proliferative or other diseases, including any disease or condition discussed below, comprising administering to a host in need of such treatment a therapeutically effective amount of a compound of Formula I, Ia, II, Ia, III or any compound disclosed herein, or an isomeric, prodrug, tautomeric, pharmaceutically acceptable salt, N-oxide, or stereoisomeric form thereof. In certain embodiments, at least one compound selected from anti-cancer agents and anti-proliferative agents may be administered conjointly with a compound of Formula I, Ia, II, IIa, III or any compound disclosed herein, or an isomeric, prodrug, tautomeric, pharmaceutically acceptable salt, N-oxide, or stereoisomeric form thereof. In a preferred embodiment, such methods of treatment comprise suitable administration of a therapeutically effective amount of a compound selected from A1 to A82, B1 to B20 and C1 to C5, or a isomeric, prodrug, tautomeric, pharmaceutically acceptable salt, N-oxide, or stereoisomeric form thereof. Conjoint administration, as the term is used herein, encompasses therapies wherein two therapeutics are combined in a single preparation, are administered, e.g., simultaneously or at different times, in separate preparations, or are otherwise administered to a patient as part of a therapeutic regimen.

In another embodiment, the invention provides a method for formulating a pharmaceutical composition comprising a therapeutically effective amount of a compound of Formula I, Ia, II, Ia, III or any compound disclosed herein, or an isomeric, prodrug, tautomeric, pharmaceutically acceptable salt, N-oxide, or stereoisomeric form thereof, and optionally a pharmaceutically acceptable carrier. In a preferred embodiment, such pharmaceutical composition comprises a therapeutically effective amount of a compound selected from A1 to A82, B1 to B20, and C1 to C5, or an isomeric, prodrug, tautomeric, pharmaceutically acceptable salt, N-oxide, or stereoisomeric form thereof. In alternative embodiment, such pharmaceutical composition comprises a therapeutically effective amount of a prodrug or pharmaceutically acceptable salt of a metabolite of compound A37 or B16, preferably a metabolite having the structure A68 or C5.

In further embodiments, the pharmaceutical compositions of the invention are for use in treating a disease, such as cancer, and other proliferative or other diseases, including any disease or condition discussed below.

In certain embodiments of the present invention, where substituted groups are used, suitable substituents can include, for example, a halogen, a hydroxyl, a carbonyl (e.g., ketones, aldehydes, carboxyls, esters, acyls), a thiocarbonyl (e.g., thioester, a thioacetate, a thioformate), an alkoxyl, a phosphoryl (e.g., phosphonate, phosphinate), a phosphate, a phosphonate, a phosphinate, an amino, an amino-alkyl, an amido, an amidine, an imine, a cyano, a nitro, an azido, a sulfhydryl, an alkylthio, ethers, —CF$_3$, alkyls, alkenyls, alkynyl, cycloalkyl, alkoxyl, silyl, sulfonyl (e.g., sulfate, sulfonamido, sulfamoyl, sulfonate), a heterocyclyl, an aralkyl (e.g., benzyl), or an aromatic or heteroaromatic moiety (e.g., phenyl, oxazyl, piperazyl, pyridyl, pyrryl). Such substituents may also, themselves, be substituted or unsubstituted.

ii. DEFINITIONS

As used herein, the following terms and expressions have the indicated meanings. The compounds of the present invention may contain an asymmetrically substituted carbon atom, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are intended, unless the specific stereochemistry or isomer form is specifically indicated. All processes used to prepare compounds of the present invention and intermediates made therein are considered to be part of the present invention.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include $^{12}$C and $^{14}$C.

The term "alkyl" is intended to include both branched and straight-chain saturated aliphatic hydrocarbon groups having the specified number of carbon atoms. Examples of alkyl include but are not limited to, methyl, ethyl, n-propyl, i-propyl, n-butyl, s-butyl, t-butyl, n-pentyl, and s-pentyl. In addition, the term is intended to include both unsubstituted and substituted alkyl groups, the latter referring to alkyl moieties having one or more hydrogen substituents replaced by, but not limited to, halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl. It will also be understood by those skilled in the art that the substituted moieties themselves can be substituted as well when appropriate. The term "lower alkyl" refers to those alkyl groups having from 1 to 6 carbon atoms, preferably from 1 to 4 carbon atoms, and the term "lower alkoxy" refers to such lower alkyl groups attached to an oxygen atom. In certain embodiments, alkyl substituents are preferably lower alkyl substituents.

The terms "halo" or "halogen" as used herein refer to fluoro, chloro, bromo and iodo.

The term "aryl" is intended to mean an aromatic moiety such as, but not limited to phenyl, indanyl or naphthyl.

The terms "cycloalkyl", and "bicycloalkyl" are intended to mean any stable ring system, which may be saturated or partially unsaturated. Examples of such include, but are not limited to, cyclopropyl, cyclopentyl, cyclohexyl, norbornyl, bicyclo[2 21nonane, adamantyl, or tetrahydronaphthyl (tetralin).

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.0]bicyclooctane, [4.0]bicyclononane, [4.0]bicyclodecane (decalin), [2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated, partially unsaturated, or unsaturated (aromatic/heteroaryl), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen in the heterocycle may optionally be quaternized. In certain embodiments, when the total number of S and O atoms in the heterocycle exceeds 1, then these heteroatoms need not be adjacent to one another. It is preferred that the total number of S atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from N, O and S. It is preferred that the total number of S and O atoms in the aromatic heterocycle is not more than 1. Examples of heterocycles include, but are not limited to, 1H-indazole, 2-pyrrolidonyl, 2H16H dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids.

For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, EtOAc, ethanol, isopropanol, or acetonitrile are preferred. Lists of suitable salts are found in *Remington's Pharmaceutical Sciences*, $18^{th}$ ed., Mack Publishing Company, Easton, Pa., 1990, p. 1445, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto or oxo (i.e., =O) group, then 2 hydrogens on the atom are replaced. Keto/oxo substituents are not present on aromatic moieties. Exemplary substituents include, for example, an alkyl, a perfluoroalkyl (such as trifluoromethyl), a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aromatic or heteroaromatic moiety. It will be understood by those skilled in the art that substituents, such as heterocyclyl, aryl, alkyl, etc., can themselves be substituted, if appropriate.

The term "therapeutically effective amount" of a compound of this invention means an amount effective to inhibit the class of enzymes known as cyclin-dependent kinases or treat the symptoms of cancer or other proliferative or other diseases in a host.

As used herein, the term "anti-cancer" or "anti-proliferative" agent includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, JM 118, etoposide, teniposide, vinblastine, vincristine, vinorelbine, procarbazine, asparaginase, pegaspargase, octreotide, estramustine, and hydroxyurea.

iii. DOSAGE AND FORMULATION

The cyclic dependent kinase inhibitors of this invention can be administered as treatment for cancer or proliferative or other diseases by any means that produces contact of the active agent with the agent's site of action in the body of a mammal. They can be administered by any conventional means available for use in conjunction with pharmaceuticals, either as individual therapeutic agents or in a combination of therapeutic agents. The chemical features of the inhibitors described herein bestow favorable solubility properties on the compounds, rendering them suitable for administration as intravenous formulations, topical formulations, oral formulations, and others as discussed in greater detail below. They can be administered alone, but preferably are administered with a pharmaceutical carrier selected on the basis of the chosen route of administration and standard pharmaceutical practice. Suitable vehicles and their formulation are described, for example, in the book *Remington's Pharmaceutical Sciences* (Remington's Pharmaceutical Sciences. Mack Publishing Company, Easton, Pa., USA 1985).

In another aspect, the present invention provides pharmaceutically acceptable compositions which comprise a therapeutically effective amount of one or more compounds of the subject invention, such as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments, the pharmaceutical preparations may be non-pyrogenic, i.e., do not elevate the body temperature of a patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association an inhibitor of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active inhibitor(s) of the present invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active prenyltransferase inhibitor, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing an inhibitor of the present invention in the proper medium. Absorption enhancers can also be used to increase the flux of the drug across the skin. The rate of such flux can be controlled by either providing a rate controlling membrane or dispersing the compound of the present invention in a polymer matrix or gel.

Ophthalmic formulations, eye ointments, powders, solutions and the like, are also contemplated as being within the scope of this invention.

Pharmaceutical compositions of this invention suitable for parenteral administration comprise one or more inhibitors of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the therapeutic effect of an inhibitor, it is desirable to slow the absorption of the inhibitor from subcutaneous or intramuscular injection. This may be accomplished by the use of a liquid suspension of crystalline or amorphous material having poor water solubility. The rate of absorption of the inhibitor then depends upon its rate of dissolution which, in turn, may depend upon crystal size and crystalline form. Alternatively, delayed absorption of a parenterally administered inhibitor form is accomplished by dissolving or suspending the inhibitor in an oil vehicle.

Injectable depot forms are made by forming microencapsulated matrices of the subject inhibitors in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the CDK inhibitors useful in the subject method may be used in a suitable hydrated form, and/or the pharmaceutical compositions of the present invention, are formulated into pharmaceutically acceptable dosage forms by conventional methods known to those of skill in the art.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol, or Capmul, in a soft gelatin capsule. Antioxidants may be added to prevent long-term degradation as appropriate.

Liquid dosage forms for oral administration can contain coloring and flavoring to increase patient acceptance. In general, water, a suitable oil, saline, ethanol, aqueous dextrose (glucose), and related sugar solutions, glycols such as propylene glycol or polyethylene glycols, or mixtures of these are suitable carriers for parenteral solutions.

For intravenous administration, compounds disclosed above may be formulated as a sterile solution of the active ingredient, either in its free or salt form, in physiological buffer or sterile water. Sugar-containing carrier liquids (such as Ringer's lactate, or other glucose or dextrose solutions) can be used if desired, provided that the total sugar content does not cause undesired levels of lactic acidosis. Intravenous administration can be either through bolus injection (preferably several times per day), or through continuous infusion over a sustained period of time. Total preferred dosages for bolus injection or infusion may vary substantially, depending on a patient's physical condition; in general, they will usually range from about 25 mg/kg to about 250 mg/kg.

Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben, and chlorobutanol. Suitable pharmaceutical carriers are described in *Remington's Pharmaceutical Sciences*, 18$^{th}$ ed., Mack Publishing Company, Easton, Pa., 1990, a standard reference text in this field, the disclosure of which is hereby incorporated by reference.

iv. THERAPEUTIC APPLICATIONS

Due to the key role of cdks in the regulation of cellular proliferation in general, the compounds disclosed herein may act as reversible cytostatic agents which may be useful in the treatment of any disease process which features abnormal cellular proliferation, such as hyperproliferative diseases, including cancer, benign prostate hyperplasia, familial adenomatosis polyposis, neurofibromatosis, psoriasis, fungal infections, endotoxic shock, hypertrophic scar formation, inflammatory bowel disease, transplant rejection, vascular smooth muscle cell proliferation associated with atherosclerosis, psoriasis, pulmonary fibrosis, arthritis, glomerulonephritis, restenosis following angioplasty or vascular surgery, and other post-surgical stenosis and restenosis. See, for example, U.S. Pat. Nos. 6,114,365 and 6,107,305.

The compounds disclosed herein are expected to be useful in the therapy of proliferative or hyperproliferative diseases such as cancer, autoimmune diseases, viral diseases, fungal diseases, neurodegenerative disorders and cardiovascular disease.

More specifically, the compounds disclosed herein are useful in the treatment of a variety of cancers, including (but not limited to) the following: carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma; hematopoietic tumors of myeloid lineage, including acute and chronic myelogenous leukemias, myelodysplastic syndrome, and promyelocytic leukemia; tumors of mesenchymal origin, including fibrosarcoma and rhabdomyosarcoma; tumors of the central and peripheral nervous system, including astrocytoma, neuroblastoma, glioma, and schwannomas; and other tumors, including melanoma, seminoma, teratocarcinoma, osteosarcoma, xenoderoma pigmentosum, keratoctanthoma, thyroid follicular cancer, and Kaposi's sarcoma.

Compounds disclosed herein may also be useful in the treatment of Alzheimer's disease, as suggested by the recent finding that cdk5 is involved in the phosphorylation of tau protein (J. Biochem, 117, 741-749 (1995)).

Compounds disclosed herein may induce or inhibit apoptosis. The apoptotic response is aberrant in a variety of human diseases. Compounds described herein, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds disclosed herein, as inhibitors of the cdks, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus, and adenovirus).

Compounds disclosed herein may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds disclosed herein may also be useful in inhibiting tumor angiogenesis and metastasis.

Compounds disclosed herein may also be employed in the prevention of hair loss that ordinarily accompanies many traditional chemotherapeutic regimens. For example, a CDK inhibitor of the invention may be used to inhibit proliferation of cells in hair follicles, thereby sparing them from attack by a cytotoxic agent that targets proliferating cells.

Compounds disclosed herein may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methotrexate. In such combinations, the compounds and formulations of the present invention may be useful for the prevention or reduction of incidence of alopecia, which is often induced by radiation therapy or chemotherapy.

If formulated as a fixed dose, such combination products employ the compounds of this invention within the dosage range described below and the other pharmaceutically active agent or treatment within its approved dosage range. For example, the cdc2 inhibitor olomucine has been found to act synergistically with known cytotoxic agents in inducing apoptosis (*J. Cell Sci.,* 108, 2897 (1995)). Compounds described herein may also be administered sequentially with known anticancer or cytotoxic agents when a combination formulation is inappropriate. The invention is not limited in the sequence of administration; compounds described herein may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research,* 57, 3375 (1997).

v. SYNTHESIS

The compounds of the present invention can be synthesized using the methods described below, together with synthetic methods known in the art of synthetic organic chemistry, or variations thereon as appreciated by those skilled in the art. Preferred methods include, but are not limited to, those methods described below. Each of the references cited below is hereby incorporated herein by reference.

Key intermediates preparing the compounds of Formula I, Ia, III and certain other compounds disclosed herein, are pyrazole aminonitriles II, aminocarboxamides III, and aminoesters IV. The preparation of these intermediates has precedence in the chemical literature, and several methods are summarized in Schemes A (A. O. Abdelhamid, et al., *J. Heterocycl. Chem.* 1984, 21, 1049), B (C. C. Cheng and R. K. Robins, *J. Org. Chem.* 1956, 21, 1240.), C (P. Schmidt and J. Druey, *Helv. Chem. Acta* 1956, 39, 986.). See also Tominaga et al., *J. Heterocycl. Chem.* 1990, 27, 775, and PCT Applications Nos. WO 00/21926 and WO 99/54308. A wide variety of starting hydrazines and aldehydes are commercially available or can be prepared by standard organic transformations. The substituent Ar, as used below, indicates an aryl ring, substituted to conform to or to be converted to a corresponding aryl substitutent of Formula I. Compounds of Formula I can also be prepared by treating PrCOCl with $CH_2(CN)_2$ in the presence of base, treating the resulting compound with $PCl_5$, and reacting the product with $ArNHNH_2$.

Scheme A

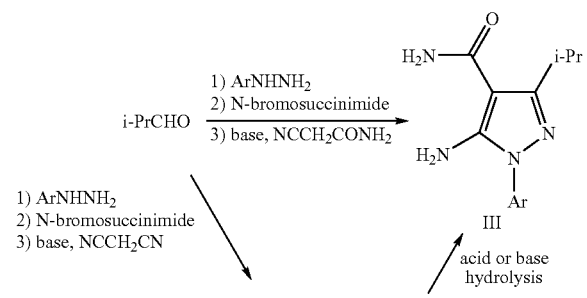

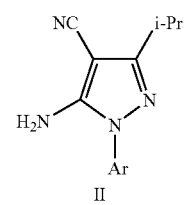

Scheme B

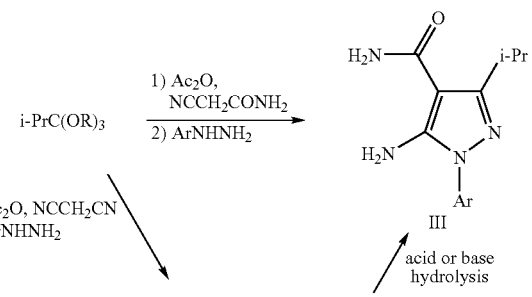

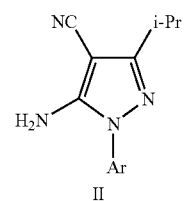

Scheme C

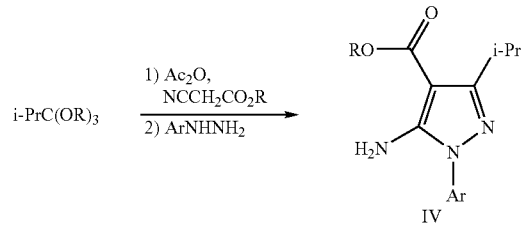

Aminonitriles II can be converted to pyrazolo[3,4-d]pyrimidines of the present invention as shown in Scheme D. In summary, the aminocarboxamide is acylated, optionally in the presence of a suitable solvent, such as dichloromethane, by treatment with a suitable base, such as triethylamine, followed by an acid halide of the formula ArCH$_2$COX, preferably an acid chloride to give carboxamidonitriles V. Alternately carboxamidonitriles V can be prepared by coupling aminonitriles II with carboxylic acids of the general formula ArCH$_2$CO$_2$H in the presence of a suitable base and coupling reagent in a suitable solvent. The coupling of amines and carboxylic acids has been reviewed (Klausnew and Bodansky, *Synthesis* 1972, 453-463), and the variety of reagents available for effecting it can be appreciated by those skilled in the art.

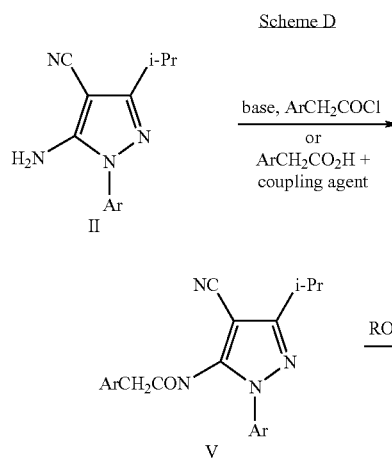

Transformation of carboxamidonitriles V to the compounds of the present invention can be accomplished by treatment with an excess of hydrogen peroxide in the presence of a suitable base, preferably a metal hydroxide or alkoxide base in a solvent, preferably water, an alcohol, or a water-alcohol mixture at a temperature in the range of about 0° C. up to 100° C.

Alternatively, carboxamidonitriles V can be transformed to the compounds of the present invention by heating, preferably for about an hour in concentrated, strong acid, preferably 85% H$_3$PO$_4$. Scheme E shows an alternative means for preparing the compounds of the present invention. Amino carboximides III in a suitable solvent, preferably a lower alkanol, are treated with an excess of an ester of the formula ArCH$_2$CO$_2$R, where R is, for example, lower alkyl, and an excess of a base, preferably a metal lower alkoxide, preferably at the boiling point of the solvent, to give compounds of the present invention. Many arylacetic esters are commercially available or can be prepared in one step from commercially available arylacetic acids by esterification with an excess of an alcohol, ROH, preferably at reflux with ethyl or methyl alcohol, used as solvent in the presence of an acid catalyst such as H$_2$SO$_4$ or p-TsOH. Alternatively, a coupling reagent such as DCC can be used, preferably in a solvent such as CH$_2$Cl$_2$ with a catalyst such as DMAP.

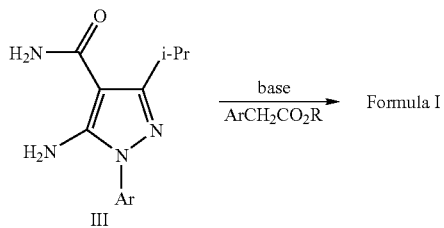

Phenylacetic acids may be prepared by acid or base hydrolysis of arylacetonitriles, which in turn may be prepared by treatment of aryl halides with CN—, preferably in solvents such as DMF, MeOH, ETOH, water, DMSO, or mixtures thereof. Further examples of arylacetic esters may be prepared from aryl carboxylic acids under Arndt-Eistert (Meier and Zeller, *Angew. Chem. Int. Ed. Engl.* 1975, 14, 32) or related homologation conditions.

Aminoesters of the formula IV can be converted to compounds of the present invention by reaction with an excess of a nitrile of the formula ArCH$_2$CN and sodium.

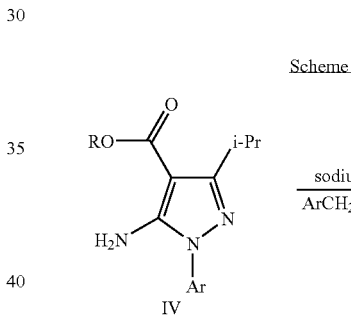

This reaction is preferably performed neat with heating.

Pyrazolo[3,4-d]pyrimidinones may be further elaborated as described below to give additional compounds of the present invention. Electrophilic aromatic substitution reactions can be performed on the Ar group to introduce substituents. Such reactions include, but are not limited to, nitration, acylation (Friedel-Crafts), halogenation, alkylation (Friedel-Crafts), chloromethylation, sulfonation, and aminomethylation (Mannich reaction). Conditions for performing these reactions are familiar to those skilled in the art of organic synthesis, generally involving reaction of the electrophile with the aryl or heteroaryl substrate in the presence of a catalyst. In the case of nitrations or Mannich reactions, the catalyst is preferably a protic acid that may serve as solvent, where the electrophile is generated in situ from saltpeter, or an amine and a carbonyl component, respectively. For other electrophilic aromatic substitution reactions, preferred catalysts are Lewis acids, including, but not limited to, FeX$_3$, AlX$_3$, and ZnX$_2$, where X is halogen.

The compounds prepared above which have an amino group can be derivatized by reaction with electrophiles including, but not limited to acyl halides, anhydrides, isocyanates, chloroformates, sulfonyl halides, alkyl halides, lactones, or esters. Conditions for performing these addition reactions are familiar to those skilled in the art of organic synthesis, generally involving addition of the electrophile to the nucleophile, preferably in solution at a temperature between 0° C. and RT. Addition of a base may be necessary. It should be noted that the products of these reactions may react further with some electrophiles at the pyrimidinone nitrogen (N5). The resulting functional groups (amides, carbamates, etc.) are less stable to basic hydrolysis than the desired anilino- or aliphatic groups and can be cleaved back to the pyrimidinone having H on N5.

Reaction of compounds bearing an amine group with agents such as haloacyl halides, α,β-unsaturated acid halides, or halosulfonyl halides gives intermediates which can react with nucleophiles such as primary or secondary amines, diamines, alkoxides, amino alcohols, or thiols.

The compounds prepared above, which have a carboxyl group, can be derivatized by activation and reaction with nucleophiles including, but not limited to amines and alcohols to give, respectively, amides and esters. The coupling of amines and carboxylic acids with carbodiimides has been reviewed (Klausnew and Bodansky, *Synthesis* 1972, 453-463), and the variety of additional reagents available for effecting it as well as the potential need for protecting groups (Green and Wuts, "Protective Groups in Organic Synthesis" Second Edition, John Wiley & Sons, 1991) to mask reactive functionality can be appreciated by those skilled in the art. The preparation of esters from acids has been described above. Reduction of these amides and esters to amines and alcohols can be performed using a suitable hydride reducing agent.

The compounds prepared above which have an amino group can be derivatized by conversion to an electrophilic species by activation with phosgene or a phosgene equivalent (*Tetrahedron: Asymmetry* 1995, 61, 745; *J. Org. Chem.* 1994, 59, 1937), preferably in the presence of a base, and reaction with nucleophiles including, but not limited to, amines, alcohols, and sulfonamides to give, respectively, ureas, carbamates, and sulfonylureas. Conditions for performing these reactions and the hazards associated with handling phosgene and phosgene equivalents are familiar to those skilled in the art of organic synthesis, and all appropriate precautions should be taken.

Further transformations which may be required to prepare compounds of the present invention include reductions of ketones, aldehydes, esters, acids, amides or reductive aminations by alumino- and borohydride reagents (J. Seyden-Penne, "Reductions by the Alumino and Borohydrides in Organic Synthesis" VCH Publishers, Inc., 1991) and oxidations of groups including but not limited to alcohols, aldehydes, olefins, thioethers, sulfoxides, and heteroaryl groups (Milos Hudlicky, "Oxidations in Organic Chemistry" American Chemical Society, 1990).

Reduction of functional groups such as alkenes, alkynes, nitrogen, nitro, or cyano groups can be accomplished by catalytic hydrogenation or by dissolving metal reduction. Further elaboration of intermediates containing electrophilic sites to compounds of the present invention can be accomplished by displacement with nucleophiles including, but not limited to, CN—, amines, alkoxides, mercaptans, or carbanions. Still other compounds of the present invention can be prepared by coupling of aryl halides or triflates with the appropriate boronic acids or stannanes (Stille, J. K., *Angew. Chem. Int. Ed. Engl.* 1986, 25, 508; Suzuki, A. *Pure Appl. Chem.* 1985, 57, 1749). The compounds prepared above, which have a carbonyl group, can be derivatized further by reaction with nucleophiles to give secondary alcohols. Such nucleophiles include, but are not limited to, Grignard reagents, alkyl-, alkenyl-, and alkynyl-lithium reagents, and allyl stannanes, silanes, and the like. Compounds prepared as described above can be further elaborated by rearrangements such as the Beckmann (Gawley in *Org. React.* 1988, 35, 1) or other rearrangements.

Further elaboration of the compounds prepared above can be accomplished by generation of an organomagnesium or organolithium species by directed metallation (Beak and Meyers, *Acc. Chem. Res.* 1986, 19, 356-363; Beak and Snieckus, *Acc. Chem. Res.* 1982, 15, 306-312; Katritzky, Lam, and Sengupta, *Prog. Heterocycl. Chem.* 1989, 11, 1-29) or from an aryl halide by lithium-halogen exchange (Parham and Bradsher, *Acc. Chem. Res.* 1982, 15, 300-305).

An approach to preparing compounds of Formula II, IIa and certain other compounds disclosed herein is presented in Scheme I and can be used to prepare compounds of the present invention. The substituents Z, $R_5$, $R_6$, and $R_7$ represent substituents as set forth in Formula II, or substituents that can be converted to those substituents using standard organic transformations. P represents a suitable protecting group. Examples of protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). The nitro group of dimethyl nitrophthalate was reduced to the amine using catalytic hydrogenation. The aniline was acylated using acetic anhydride and pyridine as a base. A mixture of the resulting acetamide 2 and an acetophenone were treated with a strong base in an appropriate solvent at elevated temperature to give the desired triketone 3. Additional means of preparing triketones are known to one skilled in the art as described in Kilgore et al, *Industrial and Engineering Chemistry* 34:494-497, 1946. The triketone was treated with hydrazine at elevated temperature in an appropriate solvent to give the indeno[1,2-c]pyrazolone ring system.

Additional means of preparing indeno[1,2-c]pyrazolones are known to one skilled in the art as described in Lemke et al., *J. Heterocyclic Chem.* 19:1335-1340, 1982; Mosher and Soeder, *J. Heterocyclic Chem.* 8:855-59, 1971; Hrnciar and Svanygova, *Collect. Czech. Chem. Commun.* 59:2734-40, 1994. The amide was deacylated by heating with a strong acid in an appropriate solvent to give aniline 4. This aniline was acylated under standard conditions using an acid chloride in an appropriate solvent to give the desired product 5.

Scheme 1

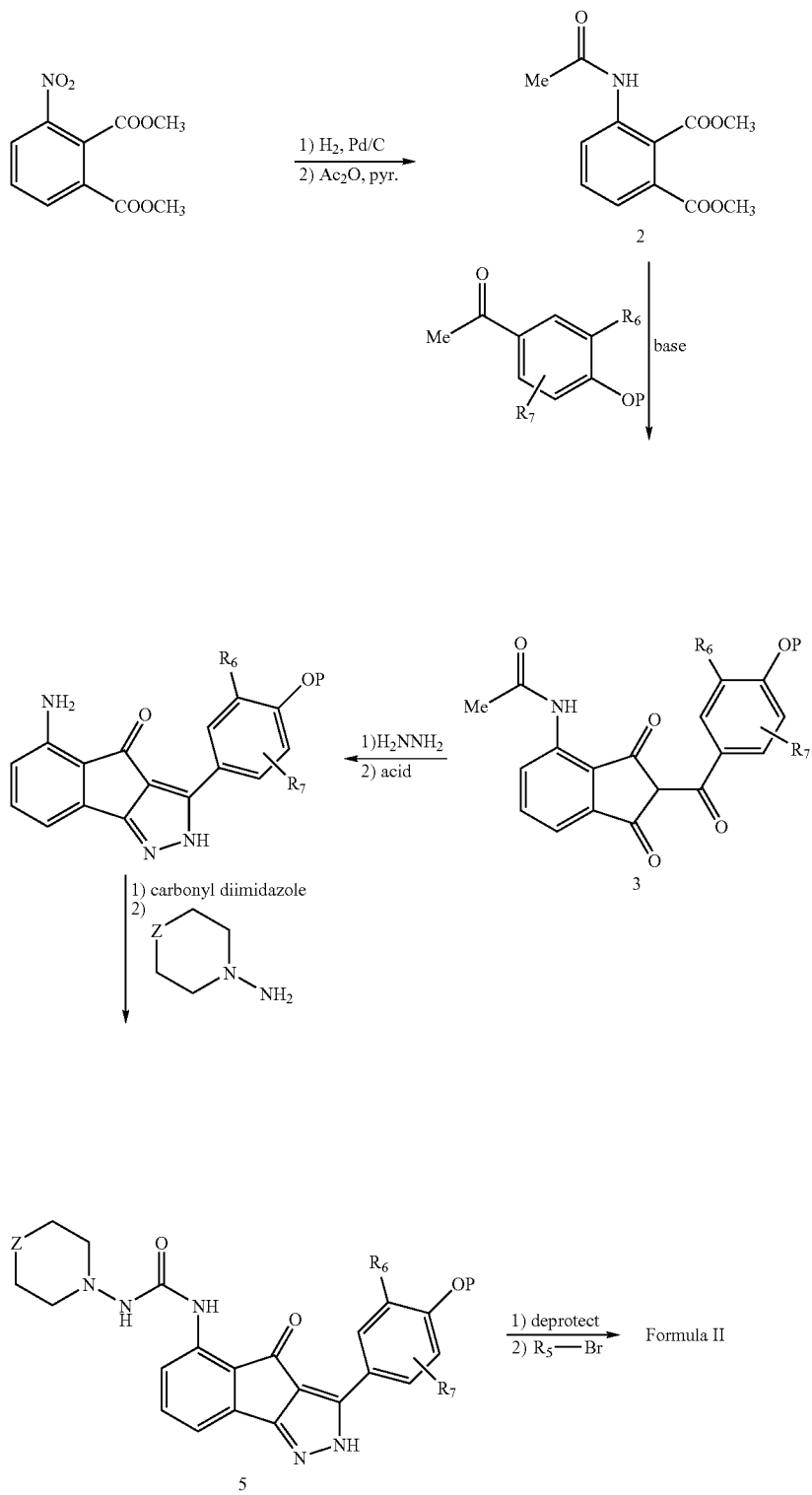

An alternative method for making compounds of the present invention is shown in Scheme 2. The intermediate triketone 3 can be deacylated with strong acid and reacylated with an appropriate acid chloride using methods known to those skilled in the art. Subsequently, triketone 6 can the be converted to the indeno[1,2-c]pyrazolone ring system using the same conditions described previously in Scheme 1.

Scheme 2

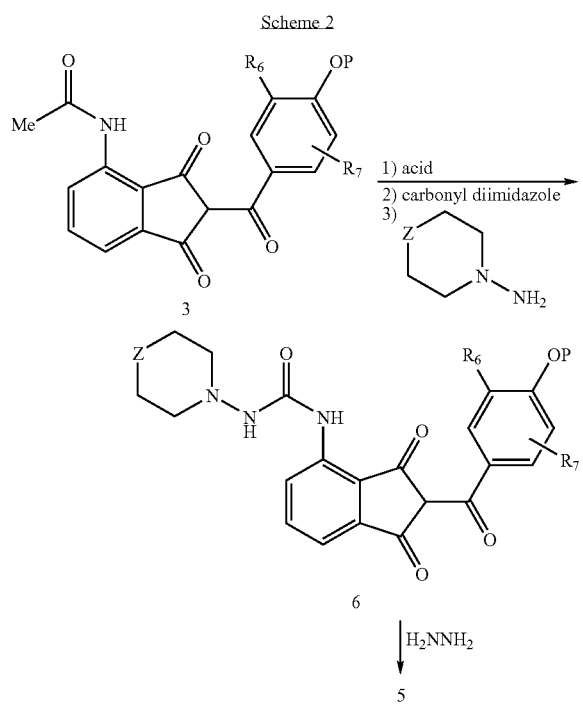

Another method for preparing the triketones 6 of Scheme 2 employs the condensation of a 1,3-diketone 6a with 3-nitrophthalic anhydride as described in Rotberg and Oshkaya, *Zh. Organ. Khim.* 8:84-87, 1972; *Zh. Organ. Khim.* 9:2548 2550, 1973. The 1,3-diketones, when not commercially available, can be readily prepared by one skilled in the art by the acetylation or trifluoroacetylation of the requisite methyl ketone. Reduction of the resulting nitro derivative to the aniline 6b can be accomplished in a variety of ways including catalytic hydrogenation, treatment with zinc or iron under acidic conditions, or treatment with other reducing agents such as sodium dithionite or stannous chloride. Subsequently the aniline 6c can be converted to the indeno[1,2-c]pyrazolones of this invention by acylation followed by treatment with hydrazine as described previously in Scheme 2.

Another method for making the indeno[1,2-c]pyrazolone ring system is shown in Scheme 3. Dimethyl hydrazine was reacted with 3-acetylpyridine with no solvent to give the hydrazone 7. This was treated in a similar fashion as described in Scheme 1 to give the desired intermediate 8.

Scheme 3

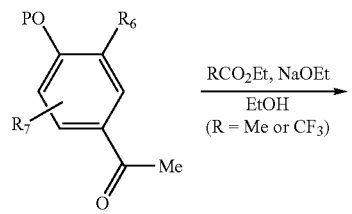

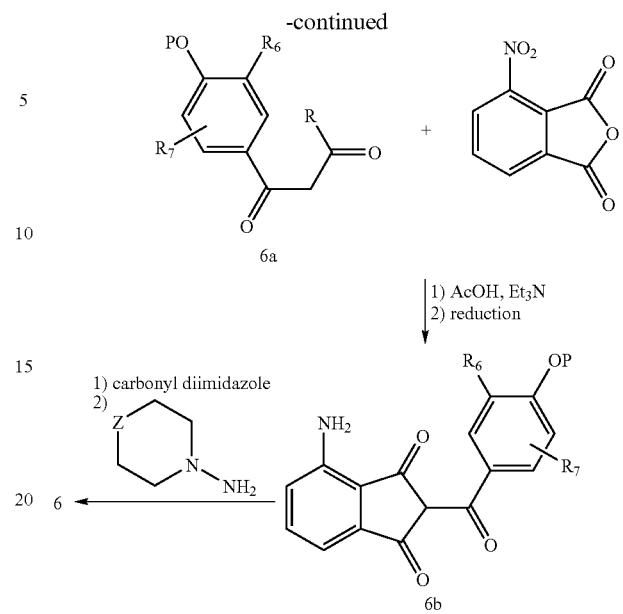

Alternatively, 6b can be treated with an activated acylated N-amino morpholine or piperazine ring, such as a nitrophenyl carbamate Additional means of preparing similar intermediates are known to one skilled in the art as described in Rappoport, *J. Org. Chem.* 49:2948-2953, 1984. This intermediate was carried through the sequence in a similar fashion as described in Scheme 1.

Although the foregoing schemes describe general synthesis routes where W is oxygen, following such general disclosure, a person skilled in the art will be able to envision and practice the synthesis of other compounds of the invention where W is not oxygen. For example, where W is selected from S, S(O$_2$), C(=O), C(=S), CH$_2$, and NR".

Other features of the invention will become apparent in the course of the following descriptions of exemplary embodiments that are given for illustration of the invention and are not intended to be limiting thereof.

v. EXEMPLIFICATION

Formula I, Ia and Certain Other Compounds Disclosed Herein

Synthesis Procedures

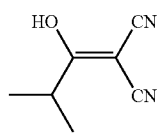

Synthesis of (1-hydroxy-2-methylpropylidene)methane-1,1-dicarbonitrile

A solution of malononitrile (4.0 g, 60 mmol) in THF (30 mL) was added dropwise over 1 h to a suspension of NaH (95%, 3.0 g, 120 mmol) in THF (75 mL) at 0° C. The reaction was then warmed to room temp and stirred for 1 h. The suspension was then cooled to 0° C. and treated dropwise with a solution of isobutyryl chloride (6.3 mL, 60 mmol) in THF (25 mL). The addition was controlled so that the internal temp does not rise above 10° C. Upon completion of the addition the reaction was warmed to room temp and stirred for 24 h. The reaction was then quenched with H₂O (10 mL) and evaporated. The residue was then partitioned between EtOAc (100 mL) and 1 N HCl (75 mL). The aqueous layer was extracted again with EtOAc (50 μL) and the combined organic layers were washed with brine (100 mL), dried (c), filtered, and evaporated to yield the desired product (7.95 g, 96%).

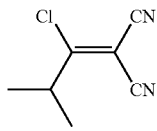

Synthesis of (1-chloro-2-methylpropylidene)methane-1,1-dicarbonitrile

To a solution of (1-hydroxy-2-methylpropylidene)methane-1,1-dicarbonitrile (5.1 g, 37 mmol) in CH₂Cl₂ (50 mL) was added phosphorous pentachloride (8.6 g, 41 mmol). The reaction was stirred at room temp for 16 h. The reaction was then poured onto ice (50 g) and partitioned between CH₂Cl₂ (50 mL) and H₂O (75 mL). The aqueous layer was extracted again with CH₂Cl₂, and the combined organic layers were washed with sat. NaHCO₃ (50 mL) and brine (75 mL). The organic layer was then dried (MgSO₄), filtered, and evaporated to yield the desired chloride (4.85 g, 84%).

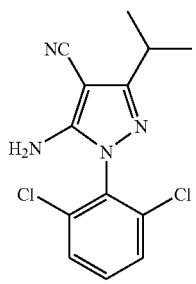

Synthesis of 5-amino-1-(2,6-dichlorophenyl)-3-isopropyl-1H-pyrazole-4-carbonitrile A solution of (1-chloro-2-methylpropylidene)methane-1,1-dicarbonitrile (9.4 g, 61 mmol) in THF (250 mL) was treated with 2,6-dichlorophenylhydrazine hydrochloride (13.0 g, 61 mmol) followed by triethylamine (12.3 g, 122 mmol). The reaction was then heated to reflux for 18 h. The reaction was then cooled to room temp and partitioned between EtOAc (150 mL) and 1N NaOH (100 mL). The aqueous layer was extracted with EtOAc (2×150 mL) and the combined organic layers were washed with 10% aq. citric acid (150 mL), sat. aq. NaHCO₃ (150 mL), and brine (150 mL). The organic layer was dried (MgSO4), filtered, and evaporated. The crude product was recrystallized from EtOAc/hexane to yield the desired pyrazole (11.2 g, 62%).

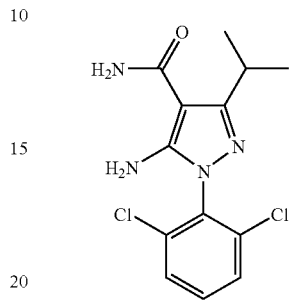

Synthesis of 5-amino-1-(2,6-dichlorophenyl)-3-isopropyl-1H-pyrazole-4-carboxylic acid amide 5-Amino-1-(2,6-dichlorophenyl)-3-isopropyl-1H-pyrazole-4-carbonitrile (15 g, 50 mmol) was taken up in conc. H₂SO₄ (45 mL) and stirred at room temp for 16 h. The reaction was then poured onto 3 N NaOH (850 mL) at 0° C. The resulting solid was then filtered and washed with H₂O (1 L). The product was then dried under vacuum to yield the desired amide (14 g, 88%).

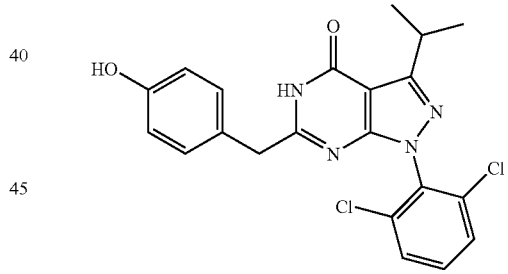

Synthesis of 1-(2,6-dichlorophenyl)-6-(4-hydroxybenzyl)-3-isopropyl-1,5-dihydropyrazolo[3,4-d]pyrimidin-4-one To a suspension of 5-amino-1-(2,6-dichlorophenyl)-3-isopropyl-1H-pyrazole-4-carboxylic acid amide (5.0 g, 16 mmol) in EtOH (20 mL) was added ethyl 4-hydroxyphenylacetate (8.6 g, 48 mmol) followed by NaOEt (2.66M in EtOH, 36 mL, 96 mmol). The reaction was then heated to reflux for 3 h. The reaction was then cooled to room temp and poured onto 10% aq. HOAc (100 mL). The resulting suspension was then cooled to 0° C. and filtered. The precipitate was then washed with 1:1 MeOH/H₂O (100 mL) and 1:1 Et₂O/hexane (75 mL). The solid was then dried under vacuum to yield the desired product (5.2 g, 76%).

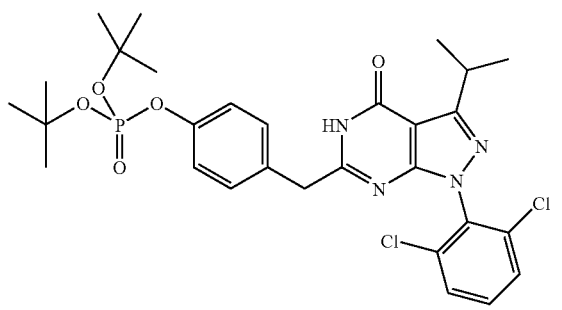

Synthesis of tert-butyl 4-{[1-(2,6-dichlorophenyl)-3-(methylethyl)-4-oxo-5-hydropyrazolo[5,4-d]pyrimidin-6-yl]methyl}benzenephosphate To a solution of 1-(2,6-dichlorophenyl)-6-(4-hydroxybenzyl)-3-isopropyl-1,5-dihydropyrazolo[3,4-d]pyrimidin-4-one (2.5 g, 5.8 mmol) in DMF (15 mL) was added di-tert-butyl N,N-diisopropylphosphoramidite (3.4 mL, 10.7 mmol) and tetrazole (1.82 g, 26 mmol). The reaction was stirred at room temp for 3 h then treated with a solution of 3-chloroperbenzoic acid (57-80%, 2.2 g, 7.2 mmol) in CH$_2$Cl$_2$ (15 mL). The reaction was stirred for 15 min then partitioned between EtOAc (50 mL) and 10% aq. Na$_2$S$_2$O$_3$ (75 mL). The organic layer was then washed with 10% aq. Na$_2$S$_2$O$_3$ (50 mL), sat. NaHCO$_3$ (50 mL), and brine (75 mL). The organic layer was then dried (MgSO$_4$), filtered, and evaporated. The crude product was purified by flash column chromatography (silica, 50% EtOAc/hexane) to yield the desired phosphate (2.7 g, 75%).

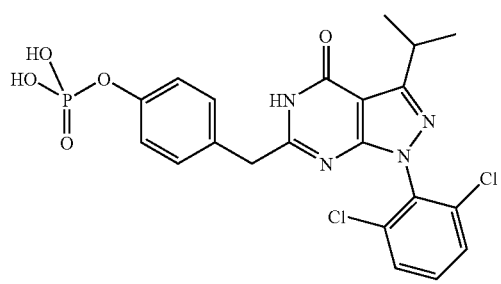

Synthesis of 1-(2,6-dichlorophenyl)-3-(methylethyl)-6-{[4-(phosphonooxy)phenyl]methyl}-5-hydropyrazolo[5,4-d]pyrimidin-4-one tert-Butyl 4-{[1-(2,6-dichlorophenyl)-3-(methylethyl)-4-oxo-5-hydropyrazolo[5,4-d]pyrimidin-6-yl]methyl}benzenephosphate (2.7 g, 4.3 mmol) was dissolved in 90% aq. trifluoroacetic acid (25 mL). The reaction was stirred at room temp for 1 h then evaporated and azeotroped with toluene (3×50 mL) to yield the free phosphate (2.15 g, 97%).

Formula II, IIa and Certain Other Compounds Disclosed Herein—Synthesis Procedures

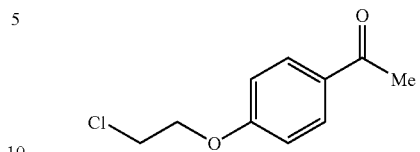

Synthesis of 1-[4-(2-chloroethoxy)phenyl]ethanone

To a solution of 4'-hydroxyacetophenone (101 g, 0.74 mole) in acetone (800 mL) was added 1-bromo-2-chloroethane (638 g, 4.45 mole) followed by K$_2$CO$_3$ (307 g, 2.22 mole). The reaction was heated to reflux for 48 h then filtered. The K$_2$CO$_3$ was washed with acetone (1 L) and the filtrate was evaporated. The residue was then partitioned between EtOAc (800 mL) and 1 N NaOH (250 mL). The organic layer was washed with 1N NaOH (250 mL) then dried and evaporated to yield 146 g of the desired product (99% yield).

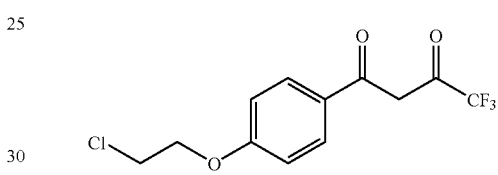

Synthesis of 1-[4-(2-chloroethoxy)phenyl]4,4,4-trifluorobutane-1,3-dione

To a solution of 1-[4-(2-chloroethoxy)phenyl]ethanone (40.5 g, 204 mmol) in THF (400 mL) at 0° C. was added ethyl 2,2,2-trifluoroacetate (34.8 g, 245 mmol). A 21 wt. % solution of NaOEt in EtOH (77 mL, 204 mmol) was added dropwise via addition funnel over 1 h. The ice bath was removed and the reaction was allowed to warm to room temp overnight. H$_2$O (400 mL) was added and the pH was adjusted to 2 by the addition of conc. HCl. The mixture was extracted with EtOAc (2×250 mL). The combined organic layers were washed with brine (200 mL), dried (MgSO$_4$) then concentrated under reduced pressure to give the diketone as a tan solid (59.3 g, 98% yield).

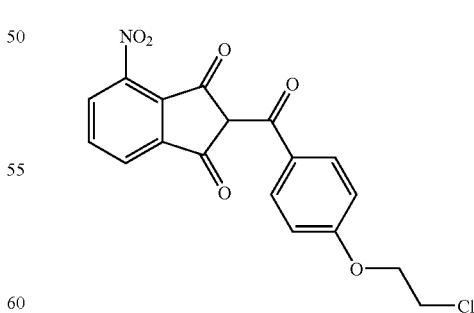

Synthesis of 2-[4-(2-Chloroethoxy)benzoyl]-4-nitroindan-1,3-dione

To a suspension of 1-[4-(2-chloroethoxy)phenyl]4,4,4-trifluorobutane-1,3-dione (59.3 g, 201 mmol) and 3-nitrophthalic anhydride (38.9 g, 201 mmol) at 0° C. in acetic anhydride (114 mL) was added triethylamine (41 g, 403 mmol). The mixture slowly turned deep red and became homogeneous. The reaction was allowed to warm to room temp overnight. The reaction mixture was cooled to 0° C. and 2N HCl (600 mL) was added slowly. The mixture was vigorously stirred for 45 min. at room temp. until a brown granular ppt formed. The brown solid was collected by filtration, resuspended in H₂O (250 mL) and stirred for 20 min. The brown solid was filtered and dried under vacuum. The crude reaction product was suspended in EtOH (500 mL) and then heated to boiling. The solution slowly turned deep red and the solid became bright yellow. The suspension was allowed to cool to room temp. The product was collected by filtration and dried under vacuum to give the triketone as a bright yellow solid (45 g, 60% yield).

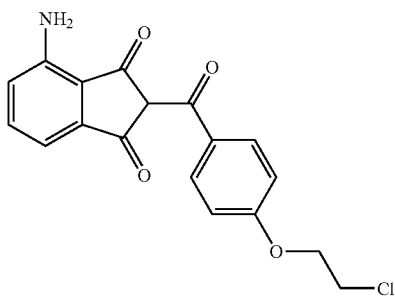

Synthesis of 4-Amino-2-[4-(2-chloroethoxy)benzoyl]indan-1,3-dione

To a suspension of 2-[4-(2-chloroethoxy)benzoyl]-4-nitroindan-1,3-dione (27 g, 72 mmol) in THF (1200 mL) under argon was added 10% Pd/C (2 g, 1.9 mmol). The argon was evacuated and replaced by a balloon of H₂. The reaction was stirred overnight and the catalyst removed by filtration. The solvent was evaporated under reduced pressure to give the desired aniline as a yellow solid (24 g, 98% yield).

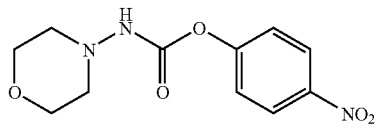

Synthesis of morpholin-4-ylcarbamic acid 4-nitrophenyl ester

To a solution of 4-nitrophenyl chloroformate (27.8 g, 0.14 mole) in CH₂Cl₂ (350 mL) at 0° C. was added a solution of 4-aminomorpholine (10.2 g, 0.1 mole) and triethylamine (10.2 g, 0.1 mole) in CH₂Cl₂ (40 mL) via addition funnel over 1 h. A white ppt formed during the addition. After the addition was complete, the ice bath was removed and the reaction was stirred an additional 1 h. The solid was collected by filtration, re-suspended in Et₂O and filtered to give the desired product as a white solid (15 g, 62% yield).

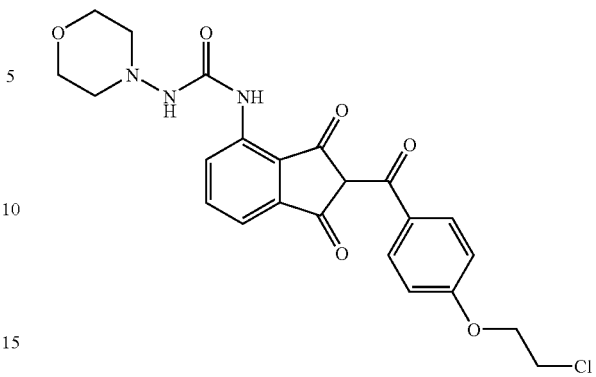

Synthesis of 1-[2-[4-(2-chloroethoxy)benzoyl]-1,3-dioxo-indan-4-yl]-3-morpholin-4-yl-urea To a suspension of 4-amino-2-[4-(2-chloroethoxy)benzoyl]indan-1,3-dione (36 g, 105 mmol) in CH₃CN (600 mL) was added morpholin-4-ylcarbamic acid 4-nitrophenyl ester (40 g, 120 mmol) followed by 4-dimethylaminopyridine (640 mg, 5.2 mmol). The reaction was heated at reflux for 4 hours then cooled to room temp. and stirred overnight. The bright yellow solid is collected by filtration, rinsed with Et₂O and dried under vacuum to give the desired semicarbazide (40.5 g, 82% yield).

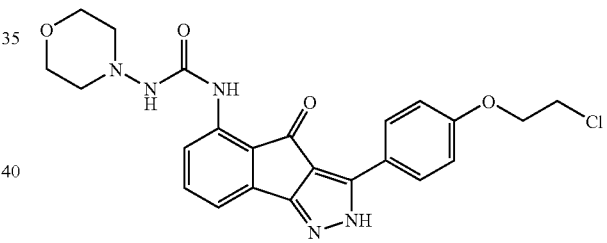

Synthesis of 1-{3-[4-(2-chloroethoxy)phenyl]-4-oxo-2,4-dihydroindeno[1,2-c]pyrazol-5-yl}-3-morpholin-4-yl urea To a suspension of 1-{2-[4-(2-chloroethoxy)benzoyl]-1,3-dioxo-indan-4-yl}-3-morpholin-4-yl-urea (39 g, 82.6 mmol) in EtOH (425 mL) was added hydrazine monohydrate (20.7 g, 413 mmol) followed by AcOH (9.9 g, 165.3 mmol). The reaction mixture was heated at reflux for 48 h. The reaction mixture was cooled to room temp. The yellow solid was collected by filtration, rinsed with EtOH and dried under vacuum. The solid was suspended in THF (1000 mL) and 1N HCl (500 mL) was added. The resulting suspension was stirred for 90 min. Brine (500 mL) was added and the pH was adjusted to 13 with 50% NaOH. The layers were separated and the aqueous layer was washed with THF (2×300 mL). The combined organic layers were washed with 1N HCl/brine (1×250 mL, 1:1), then brine (1×250 mL), dried (MgSO₄), and concentrated under reduced pressure. The yellow solid was triturated with Et₂O then dried under vacuum to give the desired pyrazole (23.5 g, 61% yield).

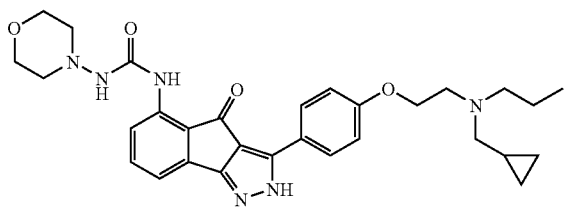

Synthesis of 1-(3-{4-[2-(cyclopropylmethyl-propylamino)ethoxy]phenyl}-4-oxo-2,4-dihydroindeno[1,2-c]pyrazol-5-yl)-3-morpholin-4-yl urea To a solution of 1-{2-[4-(2-chloroethoxy)benzoyl]-1,3-dioxo-indan-4-yl}-3-morpholin-4-yl-urea (36 g, 77 mmol) in DMSO (200 mL) was added (cyclopropylmethyl)propylamine (33 mL, 231 mmol). The reaction was heated to 70° C. for 6 days then cooled to room temp and poured onto $H_2O$ (1 L). The resulting precipitate was filtered and washed with $H_2O$. The crude product was then taken up in 3N HCl (1.5 L) and extracted with 20% $MeOH/CH_2Cl_2$ (3×1 L). The aqueous layer was then made basic (pH=12) with solid NaOH. The resulting precipitate was then filtered, washed with $H_2O$, and dried under vacuum to yield 30.7 g of the desired product (73% yield).

Formula II, IIa and Certain Other Compounds Disclosed Herein—Further Synthesis Procedures A further general process to synthesize compounds of the invention is shown in Scheme 4 below, using the synthesis of compound A37 as a specific example.

Scheme 4

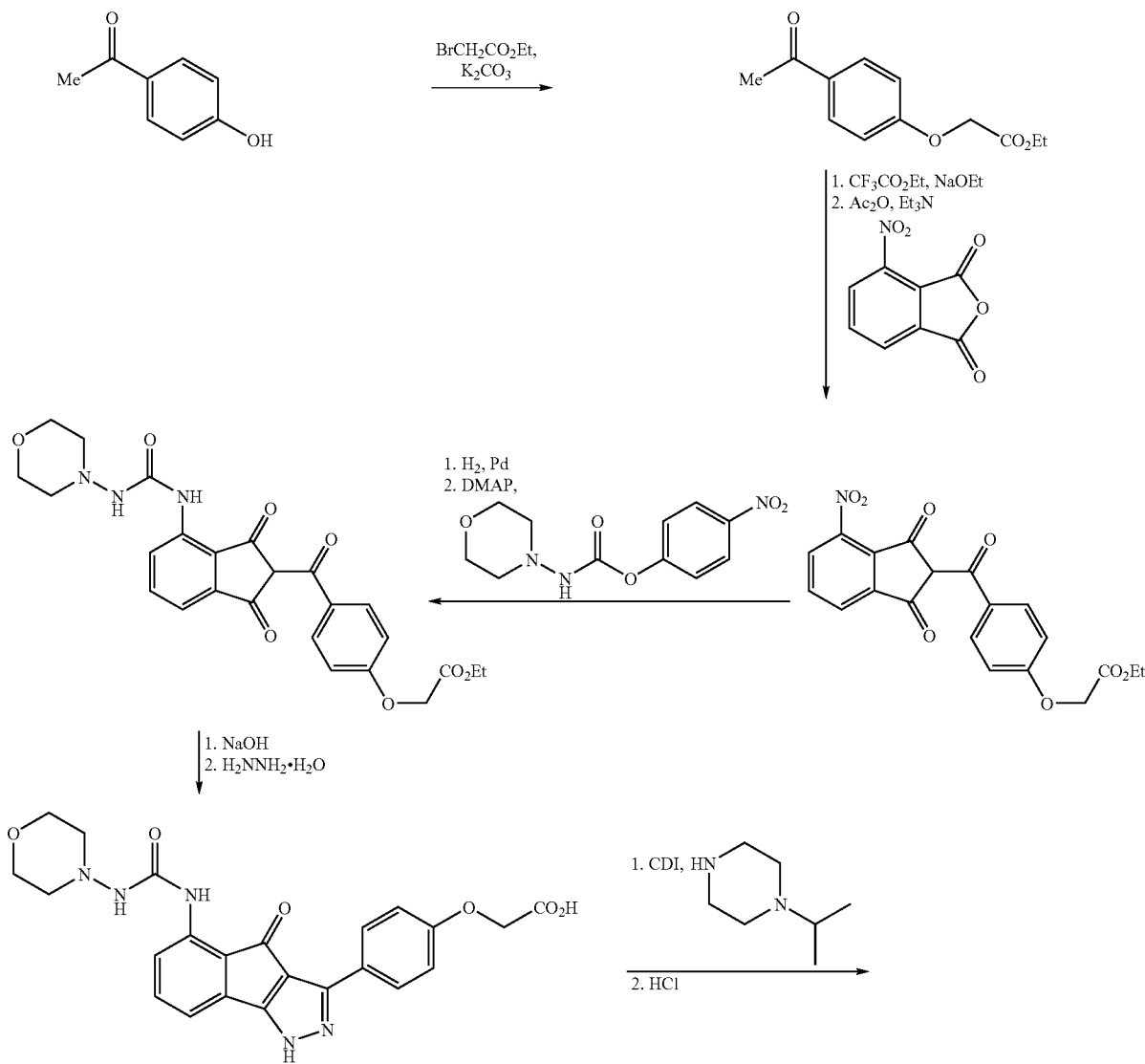

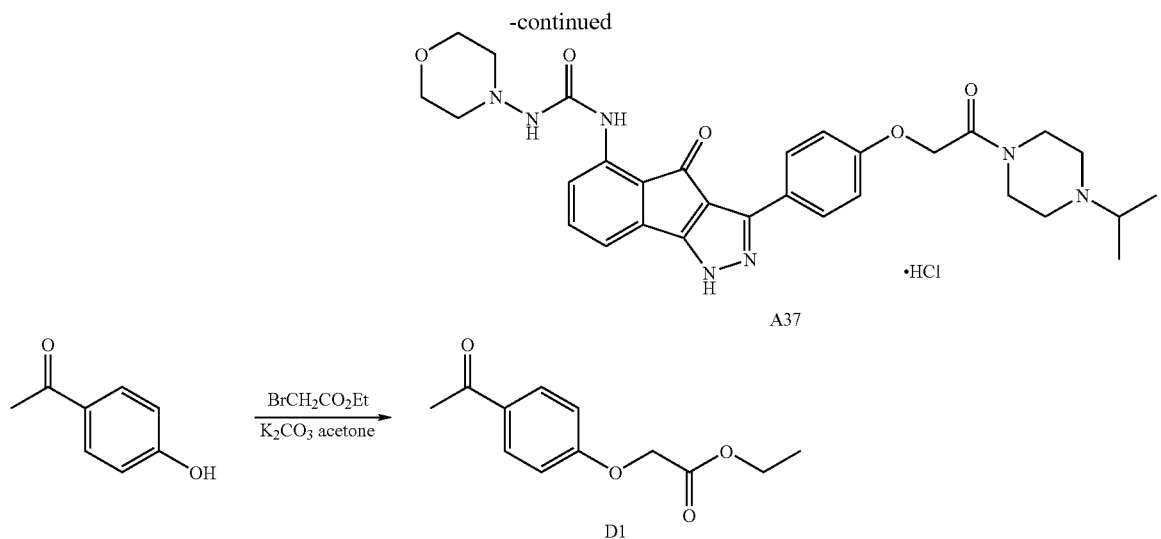

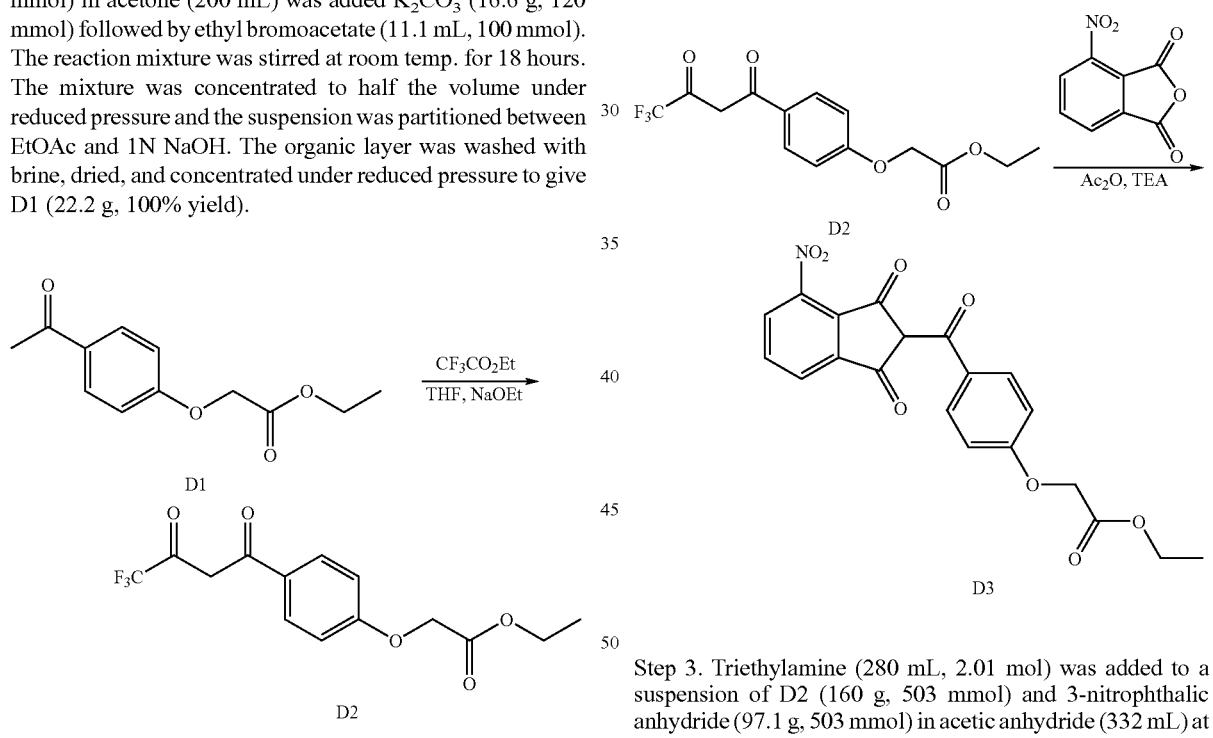

Step 1. To a solution of 4-hydroxyacetophenone (13.6 g, 100 mmol) in acetone (200 mL) was added K$_2$CO$_3$ (16.6 g, 120 mmol) followed by ethyl bromoacetate (11.1 mL, 100 mmol). The reaction mixture was stirred at room temp. for 18 hours. The mixture was concentrated to half the volume under reduced pressure and the suspension was partitioned between EtOAc and 1N NaOH. The organic layer was washed with brine, dried, and concentrated under reduced pressure to give D1 (22.2 g, 100% yield).

Step 2. A 21 wt. % solution of NaOEt in EtOH (204 mL, 542 mmol) was added dropwise via addition funnel over 40 min to a solution of D1 (110 g, 493 mmol) and ethyl trifluoroacetate (84.1 g, 592 mmol) in THF (1000 mL) at 0° C. The ice bath was removed and the reaction was allowed to warm to room temp. overnight. 2N HCl (300 mL) and brine (300 mL) were added and the layers separated. The aq layer was extracted with EtOAc (2×250 mL). The combined organic layers were washed with brine (2×200 mL), dried (MgSO$_4$), and concentrated under reduced pressure to give D2 as a tan solid (155 g, 99% yield).

Step 3. Triethylamine (280 mL, 2.01 mol) was added to a suspension of D2 (160 g, 503 mmol) and 3-nitrophthalic anhydride (97.1 g, 503 mmol) in acetic anhydride (332 mL) at 0° C. The reaction mixture was allowed to warm to room temp. overnight and slowly turned deep red, becoming homogeneous after 30 minutes. The reaction mixture was cooled to 0° C. and 1.5N HCl (4000 mL) was added. The mixture was mechanically stirred for 1 hour at room temp. until a brown granular ppt formed. The brown solid was collected by filtration, suspended in H$_2$O (2000 mL) and stirred for 20 min. The brown solid was collected by filtration, rinsed with H$_2$O (500 mL), and dried under vacuum to give 224 g of crude product. The crude reaction product was suspended in EtOH (800 mL) and heated to boiling. The solution slowly turned deep red and the solid became bright yellow. The suspension was allowed to cool to room temp. then placed in a freezer overnight. The product was collected by filtration, rinsed with cold EtOH (300 mL), and dried under vacuum to give D3 as a bright yellow solid (126 g, 63% yield).

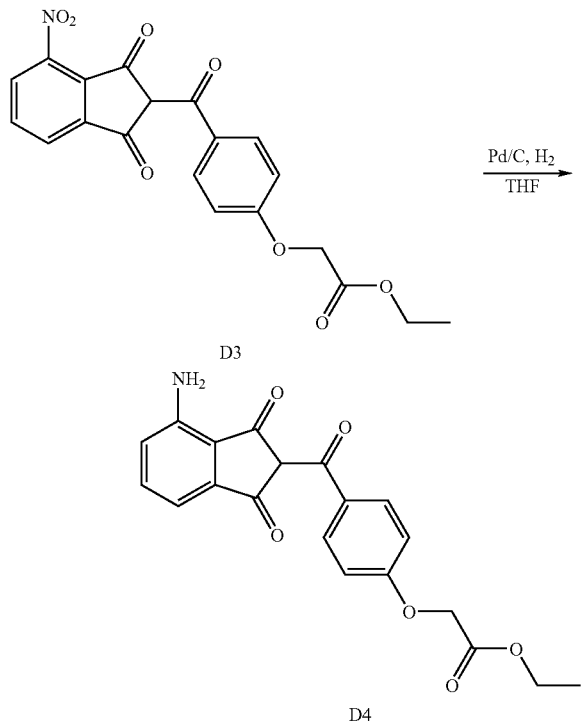

Step 4. To a solution of D3 (108 g, 273 mmol) in THF (3000 mL) under argon was added 10% Pd/C (17.0 g, 16.0 mmol). The argon was exchanged for H₂ under balloon pressure and the reaction mixture was stirred overnight. The catalyst was removed by filtration through a plug of celite and the solvent was evaporated under reduced pressure to give D4 as a yellow solid (90.3 g, 90% yield).

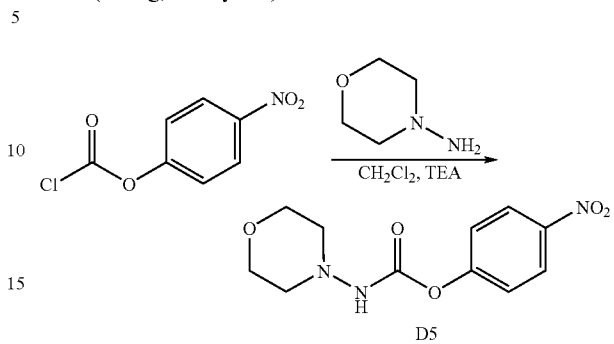

Step 5. A solution of aminomorpholine (116 g, 1.14 mol) and triethylamine (174 mL, 1.25 mol) in $CH_2Cl_2$ (210 mL) was added via addition funnel over 2 hours to a solution of 4-nitrophenyl chloroformate (275 g, 1.36 mol) in $CH_2Cl_2$ (3000 mL) at 0° C. under mechanical stirring. A white ppt formed during the addition. The reaction was stirred for 1 hour after the addition was complete. The product was collected by filtration, re-suspended in $CH_2Cl_2$ (1000 mL), stirred for 20 min, and collected by filtration (198 g, 65% yield). The combined $CH_2Cl_2$ filtrates were washed with 1N HCl (2×500 mL) and brine (2×350 mL), then dried (MgSO₄) and concentrated. The off-white solid was suspended in Et₂O (1000 mL), stirred for 20 min and collected by filtration. The Et₂O rinse was repeated to give a second crop of product (81.2 g, 27% yield). The combined batches contain ~2 wt % TEA HCl and a small amount of p-nitrophenol.

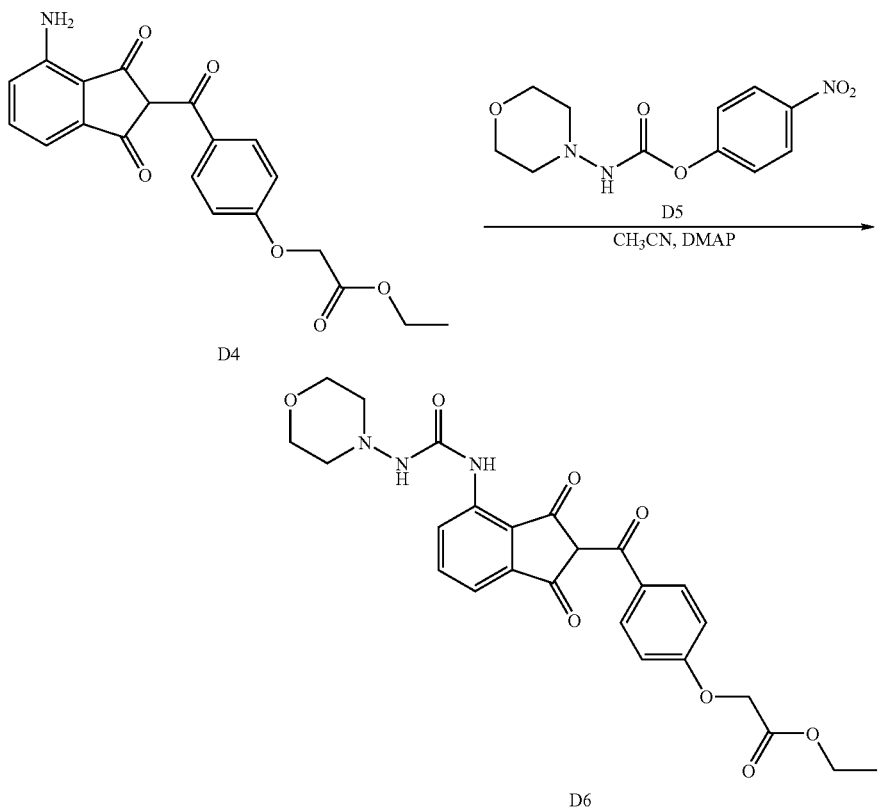

Step 6. Dimethylaminopyridine (1.50 g, 12.3 mmol) was added to a suspension of D4 (90.3 g, 246 mmol) and D5 (79.0 g, 295 mmol) in CH$_3$CN (850 mL) at room temp. The reaction mixture was heated at reflux for 4 hours. The reaction mixture became homogeneous upon heating forming a yellow ppt after 1.5 hours. After cooling to 0° C., the bright yellow solid was collected by filtration, rinsed with cold CH$_3$CN (150 mL), followed by Et$_2$O (2×200 mL), and dried under vacuum to give D6 (84.5 g, 69% yield) as a yellow solid.

with EtOAc (2×500 mL), suspended in 1N HCl (500 mL) and stirred for 20 min. After collecting the product by filtration, the HCl wash was repeated. The solid was collected by filtration, rinsed with H$_2$O (2×400 mL) and dried in a vacuum oven overnight at 75° C. to give D7 (77.4 g, 97% yield) as a yellow solid.

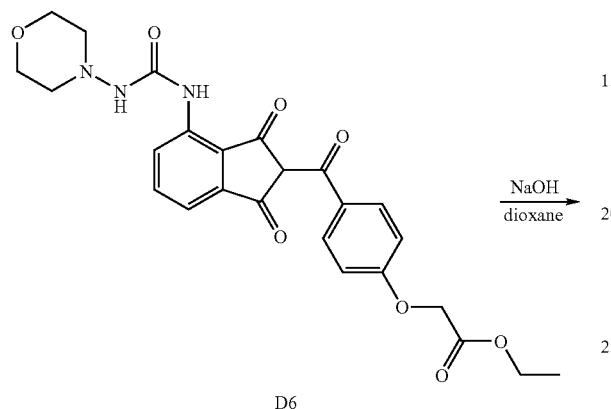

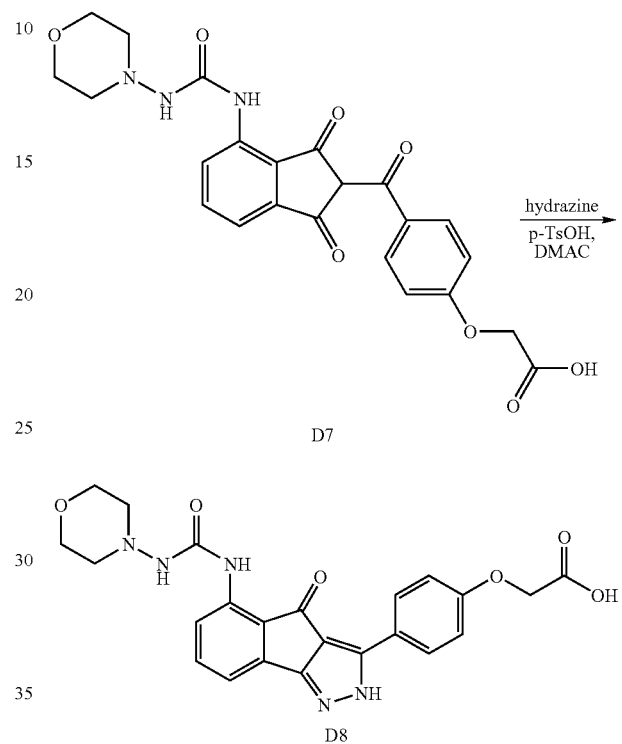

Step 7. 1N NaOH (375 mL, 375 mmol) was added to a suspension of D6 (84.5 g, 171 mmol) in dioxane (1750 mL) at room temp. The reaction mixture became homogeneous forming a yellow ppt after 15 min. The reaction mixture was stirred for 3 hours. The ppt was collected by filtration, rinsed Step 8. Hydrazine monohydrate (12.2 mL, 252 mmol) was added to a solution of D7 (23.5 g, 50.4 mmol) and p-TsOH (479 mg, 2.52 mmol) in DMAC (150 mL). The reaction mixture darkened and was heated at 50° C. overnight forming a yellow ppt after 1.5 hours. The reaction mixture was cooled to room temp. The yellow solid was collected by filtration, rinsed with EtOH (150 mL), then Et$_2$O (150 mL), and dried under vacuum to give the hydrazine salt of D8 (21 g, 84% yield). The hydrazine salt was suspended in 1N HCl (200 mL), stirred for 20 min, and collected by filtration. The yellow solid was rinsed with H$_2$O (150 mL), EtOH (150 mL), and Et$_2$O (150 mL) to give D8 (17.2 g, 74% yield) as the free acid.

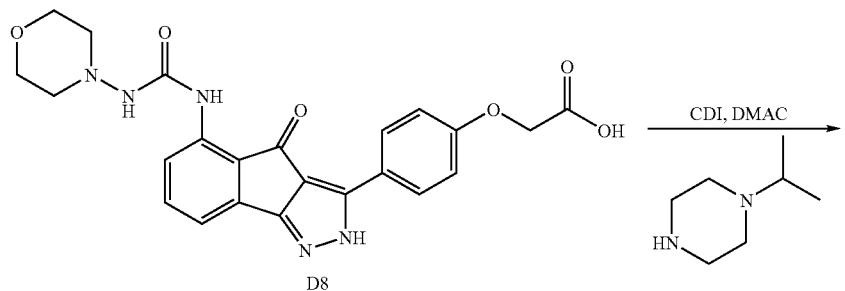

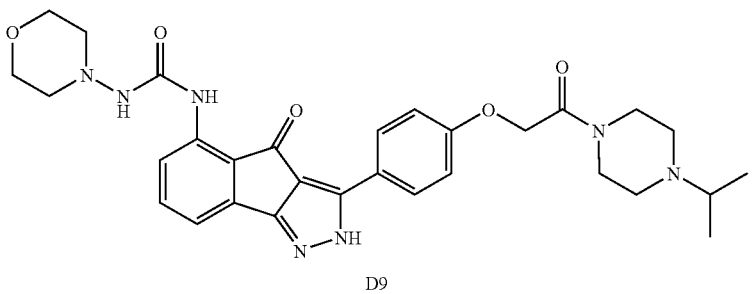

D9

Step 9. N,N'-carbonyldiimidazole (11.0 g, 67.5 mmol) was added to a solution of D8 (14.9 g, 32.2 mmol) in DMAC (100 mL) at room temp. Vigorous gas evolution was evident. The reaction mixture was stirred for 1 hour forming a yellow ppt after 15 min. Additional DMAC (50 mL) was added to aid stirring. i-Propylpiperazine (9.5 g, 74.0 mmol) was added and the reaction mixture became homogeneous. The reaction mixture was stirred overnight, forming a yellow ppt, then poured into H$_2$O (1000 mL). The solid was collected by filtration, suspended in EtOH (300 mL) and heated to boiling. After cooling slightly, the solid was collected by filtration, rinsed with EtOH (50 mL), then Et$_2$O (100 mL), and dried under vacuum to give D9 (17.4 g, 94% yield) as a yellow solid.

Step 10. A suspension of D9 (11.5 g, 20.0 mmol) in MeOH (400 mL) was heated to near boiling and a solution of 4N HCl in dioxane (5.50 mL, 22.0 mmol) was added. The mixture became homogeneous forming a yellow ppt within 5 min. After cooling to room temp. overnight, the solid was collected by filtration, rinsed with EtOH (100 mL) then Et$_2$O (200 ml), and dried in a vacuum oven (75° C., 48 hours) to give compound A37 (D10) (11.4 g, 91% yield) as a yellow solid.

An alternative general process to synthesize certain compounds of the invention is shown in Scheme 5 below, using the synthesis of compound B16 as a specific example:

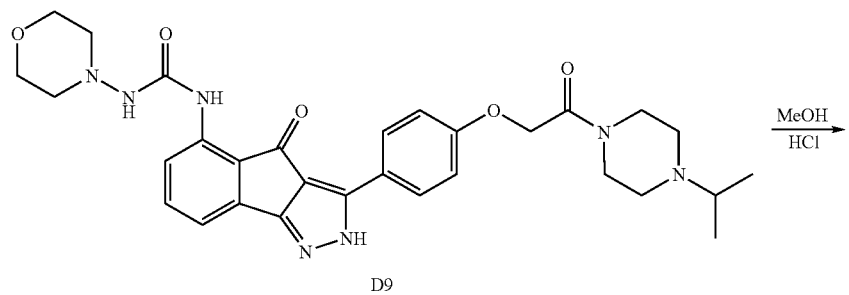

D9

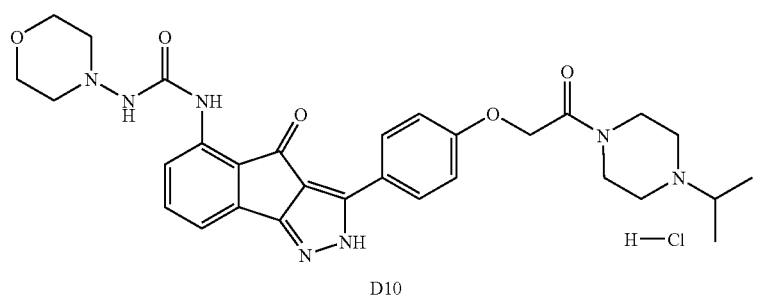

D10

Scheme 5

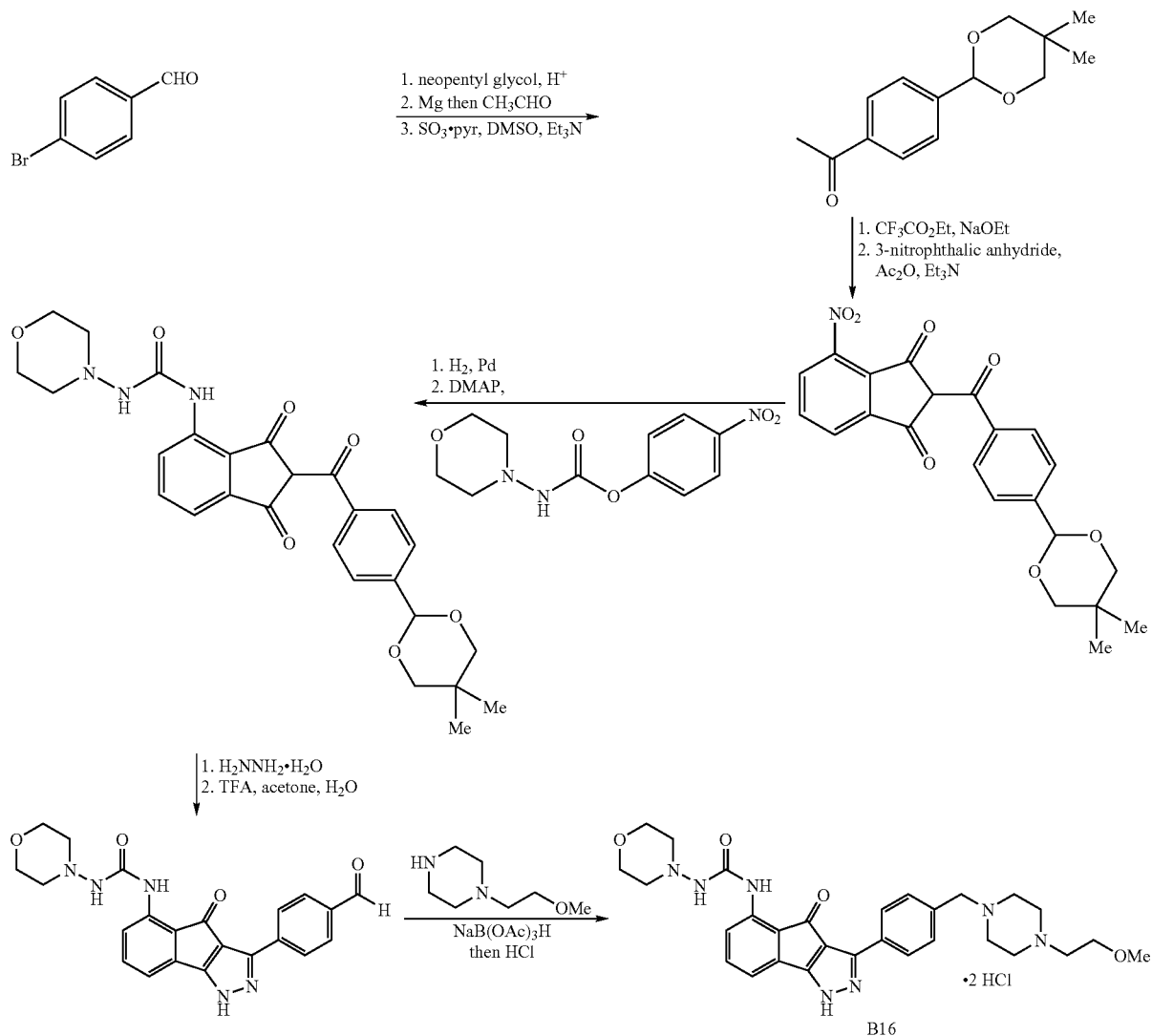

Procedures:

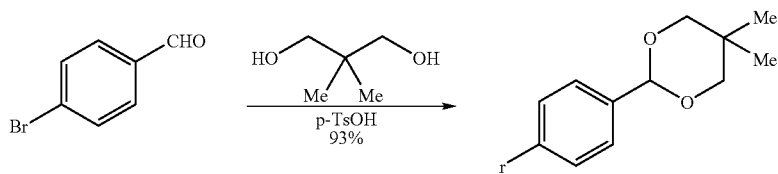

Synthesis of 2-(4-bromophenyl)-5,5-dimethyl-1,3-dioxane

A mixture of 4-bromobenzaldehyde (100 g, 0.54 mole), neopentyl glycol (115 g, 1.10 mole), and p-toluenesulfonic acid (800 mg, 4 mmole) in benzene (800 mL) was heated to reflux using a Dean Stark apparatus for 16 h. The reaction mixture was cooled to room temperature and most of the benzene was removed. The residue was partitioned between ethyl acetate (500 mL) and cold water (150 mL). The organic phase was washed with water (2×150 mL) and brine (1×150 mL), then dried ($Na_2SO_4$) and concentrated to give the desired product (136 g, 93%).

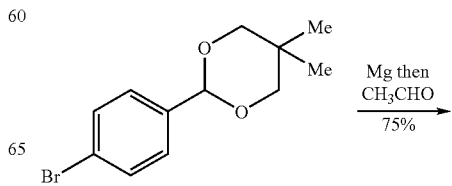

Synthesis of 1-[4-(5,5-dimethyl-1,3-dioxan-2-yl)phenyl]ethan-1-ol

To a suspension of Mg (14.4 g, 0.59 mole) in THF (1400 mL) was added 1,2-dibromoethane (0.4 mL). The suspension was then heated to 30° C. After 10 minutes a solution of the aryl bromide (146.4 g, 0.54 mole) in THF (500 mL) was added dropwise and the reaction was stirred at 35° C. overnight. The resulting dark gray solution was cooled to −5° C. in an ice/salt bath, and was treated with acetaldehyde (45.4 mL, 0.81 mole). The reaction was stirred at 0° C. for 1 h, then poured onto ice. The reaction mixture was then extracted with MTBE (750 mL), and the aqueous layer was extracted with MTBE (2×500 mL). The organic layers were combined, washed with sat. NaHCO$_3$ (750 mL), brine (750 mL), dried (Na$_2$SO$_4$), and concentrated to give the desired product as a red oil (128 g, contains ~25% reduced product by wt.; corrected yield is 96 g, 75%).

Synthesis of 1-[4-(5,5-dimethyl-1,3-dioxan-2-yl)phenyl]ethan-1-one

To a solution of the alcohol (54 g, 0.228 mole) in dichloromethane (1100 mL) at 0° C. was added triethylamine (95 mL, 0.684 mole), followed by a suspension of sulfur trioxide pyridine complex (72.6 g, 0.456 mole) in DMSO (160 mL), keeping the temperature below 5° C. The reaction was allowed to warm up to room temperature, and was stirred at room temperature for 16 h. The reaction mixture was diluted with dichloromethane (400 mL) and washed with 1N HCl (500 mL), sat. NaHCO$_3$ (500 mL), and brine (500 mL). The organic phase was then dried (Na$_2$SO$_4$) and concentrated to give 52 g (97%) of the desired product.

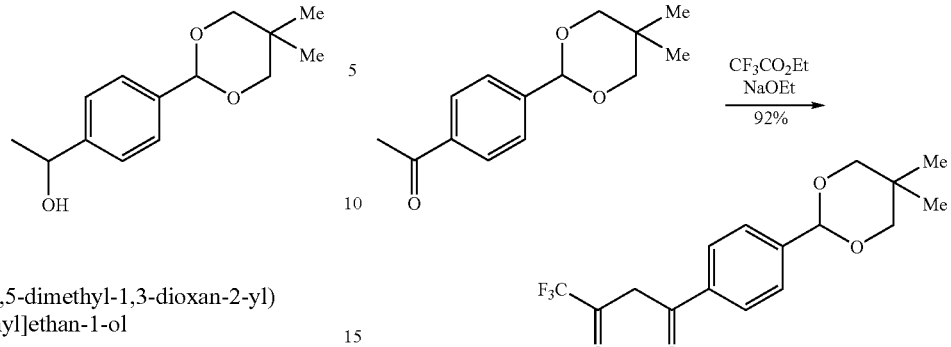

Synthesis of 1-[4-(5,5-dimethyl(1,3-dioxan-2-yl))phenyl]4,4,4-trifluorobutane-1,3-dione To a solution of the ketone (147.6 g, 0.63 mole) and ethyl trifluoroacetate (90.2 mL, 0.76 mole) in THF (1250 mL) at −4° C. was added a 21% solution of NaOEt in EtOH (308 mL, 0.82 mole) over 45 min. The resulting solution was kept at 0° C. for 1 h then warmed to room temp and stirred for 2.5 h. The reaction was then diluted with MTBE (1500 mL) and treated with 1N HCl (700 mL) and brine (500 mL). The layers were then separated and the organic phase was washed with brine (2×500 mL) then dried over Na$_2$SO$_4$, and concentrated in vacuo, to afford the β-diketone (191.3 g, 92%) as a brown solid.

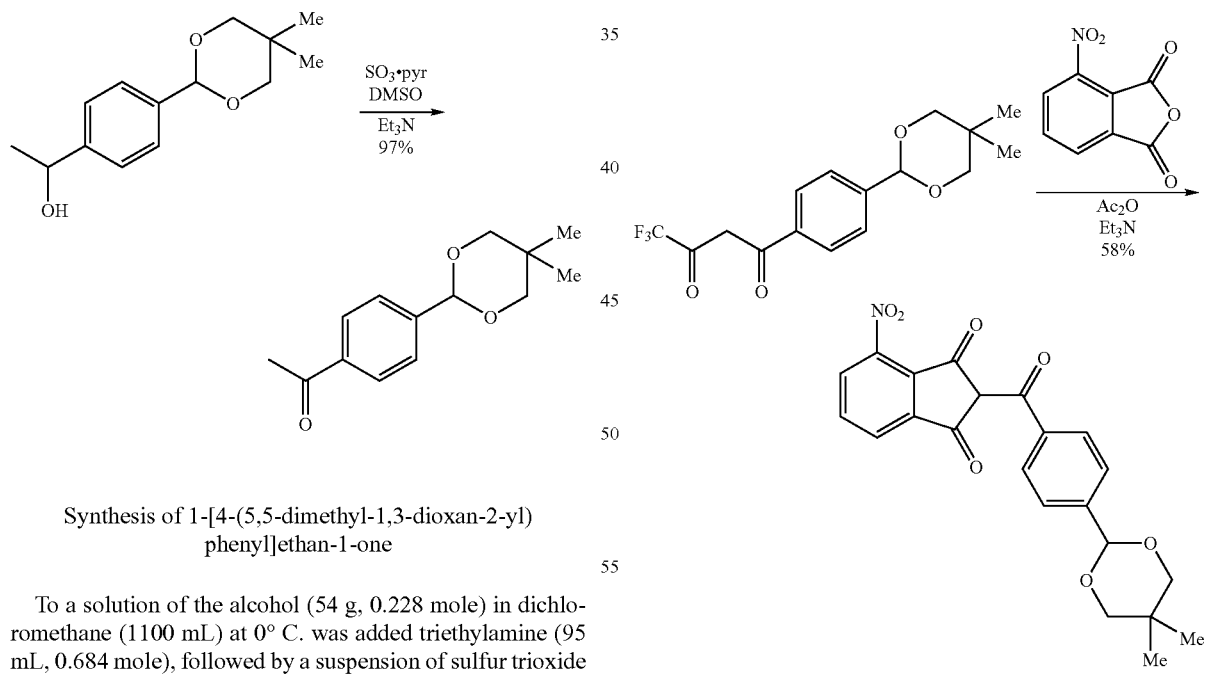

Synthesis of 2-{[4-(5,5-dimethyl(1,3-dioxan-2-yl))phenyl]carbonyl}-4-nitro-2-hydrocyclopenta[1,2-a]benzene-1,3-dione To a suspension of β-diketone (191.3 g, 0.58 mole) and 3-nitrophthalic anhydride (111.8 g, 0.58 mole) in acetic anhydride (383 mL, 4.1 mole) at 0° C. was added triethylamine (323 mL, 2.3 mole) over 15 min. The resulting dark red solution was stirred at 0° C. for 1.5 h then warmed to room temp and stirred for 16 h. The reaction was then cooled to 0° C. and treated with 1N HCl (2500 mL). The brown tarry solid was then stirred vigorously for 30 min. The liquid was then decanted and the resulting sticky brown solid was suspended in H₂O (~4 L) and stirred vigorously at room temp for 45 min. The decanting/resuspension sequence was repeated twice more and the resulting brown granular solid was dried under vacuum to yield 249 g of crude product. The crude product was then suspended in MTBE (750 mL) and heated to boiling. The resulting suspension was then placed in a 4° C. refrigerator for 16 h then filtered. The solid was then filtered, washed with cold MTBE (500 mL), and dried under vacuum to yield the desired nitrotriketone (136 g, 58%).

Synthesis of 4-amino-2-{[4-(5,5-dimethyl(1,3-dioxan-2-yl))phenyl]carbonyl}-2-hydrocyclopenta[1,2-a]benzene-1,3-dione A solution of the nitrotriketone (136 g, 0.33 mole) in THF (2500 mL) was hydrogenated using a hydrogen balloon in the presence of 10% Pd on C (2.5 g) for 18 h. The catalyst was removed by filtration through a celite pad. The filtrate was then evaporated to yield the desired amine (124 g, 99%) as a yellow foam.

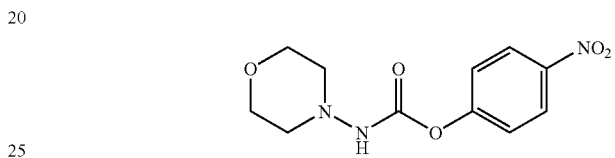

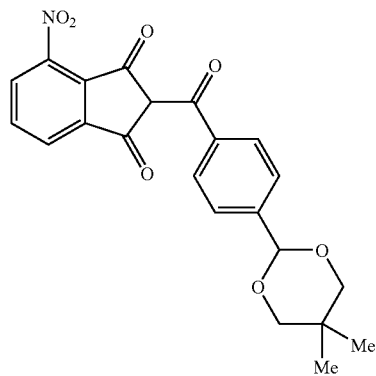

Synthesis of N-morpholin-4-yl(4-nitrophenoxy)carboxamide

A solution of aminomorpholine (116 g, 1.14 mole) and triethylamine (174 mL, 1.25 mole) in CH₂Cl₂ (210 mL) was added via addition funnel over 2 hours to a solution of 4-nitrophenyl chloroformate (275 g, 1.36 mole) in CH₂Cl₂ (3000 mL) at 0° C. under mechanical stirring. A white ppt formed during the addition. The reaction was stirred for 1 hour after the addition was complete. The product was collected by filtration, re-suspended in CH₂Cl₂ (1000 mL), stirred for 20 min, and collected by filtration (198 g, 65% yield). The combined CH₂Cl₂ filtrates were washed with 1N HCl (2×500 mL) and brine (2×350 mL), then dried (MgSO₄) and concentrated. The off-white solid was suspended in Et₂O (1000 mL), stirred for 20 min and collected by filtration. The Et₂O rinse was repeated to give a second crop of product (81.2 g, 27% yield). The combined batches contain ~2 wt % triethylamine hydrochloride and a small amount of p-nitrophenol.

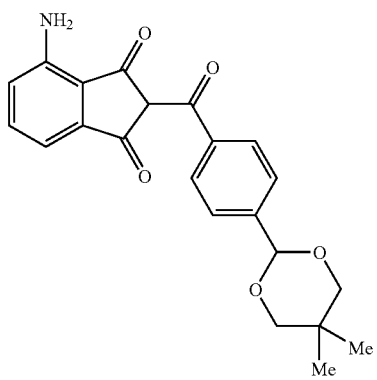

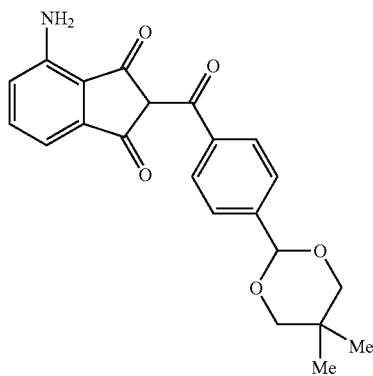

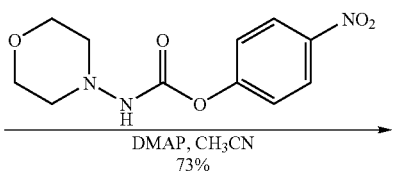

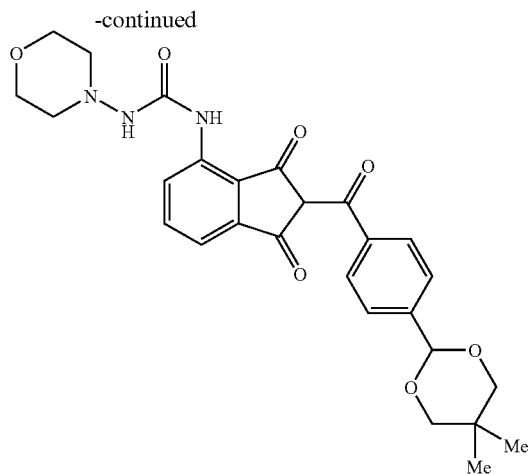

Synthesis of N-(2-{[4-(5,5-dimethyl(1,3-dioxan-2-yl))phenyl]carbonyl}-1,3-dioxo(2-hydrocyclopenta[2,1-b]benzen-4-yl))(morpholin-4-ylamino)carboxamide The aminotriketone (17 g, 0.045 mole), N-morpholin-4-yl (4-nitrophenoxy)carboxamide (15.6 g, 0.058 mole), and DMAP (0.27 g) were suspended in CH₃CN (200 mL) and heated to reflux for 18 h. The reaction mixture was then placed in a 4° C. refrigerator for 12 h. The grayish yellow solid was isolated by filtration and dried under vacuum to give the desired product (16.7 g, 73%).

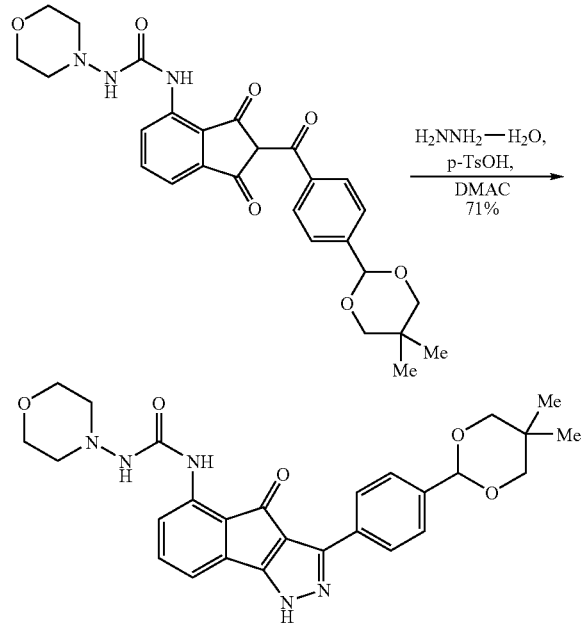

Synthesis of N-{3-[4-(5,5-dimethyl(1,3-dioxan-2-yl))phenyl]-4-oxoindeno[2,3-d]pyrazol-5-yl}(morpholin-4-ylamino)carboxamide Hydrazine hydrate (56.5 mL, 1.2 mole) was added to a suspension of the triketone (118 g, 0.23 mole) and p-toluenesulfonic acid (2.2 g, 12 mmole) in DMAC (750 mL). The reaction darkens and becomes homogeneous. The reaction was then heated to 50° C. for 18 h. After about 2 h of heating a thick yellow precipitate formed and additional DMAC (100 mL) was added to facilitate stirring. Upon completion of heating, the reaction was placed in a 4° C. refrigerator for 16 h. The resulting yellow precipitate was then filtered and washed with cold ethanol (500 mL) and H₂O (500 mL). The solid was then dried under vacuum to yield the desired pyrazole (83.4 g, 71%; contains ~8% by wt. DMAC).

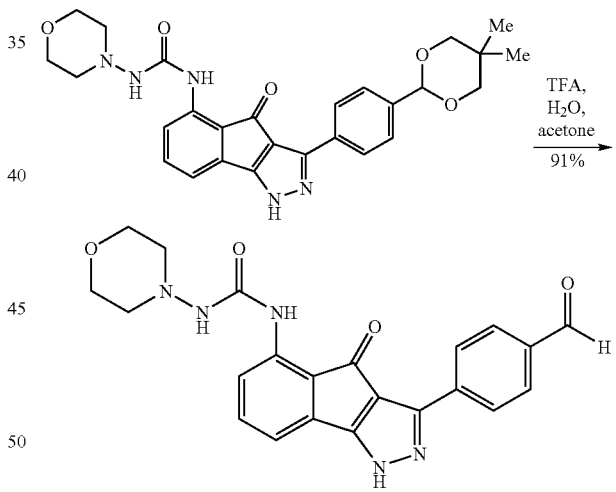

Synthesis of N-[3-(4-carbonylphenyl)-4-oxoindeno[2,3-d]pyrazol-5-yl](morpholin-4-ylamino)carboxamide To a solution of the indenopyrazole (13.1 g, 0.026 mole) in TFA (160 mL) was added acetone (75 mL) followed by water (12 mL). Solid product precipitated out of the red clear solution. The reaction mixture was stirred vigorously for 20 h, then diluted with acetone/water (100 mL, 1:1) mixture and placed in a 4° C. refrigerator for 16 h. The solid was collected by filtration and washed with water (100 μL), and acetone (50 mL). The solid was then dried under vacuum to give the desired product (9.8 g, 91%).

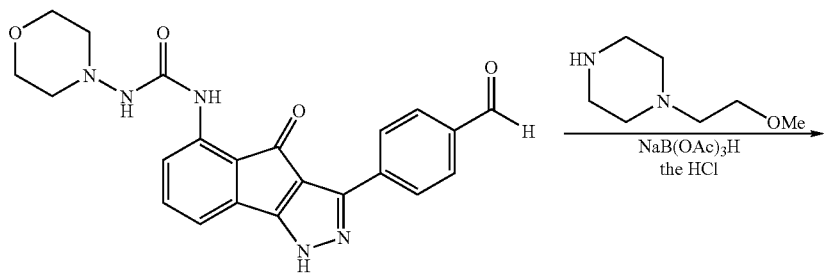

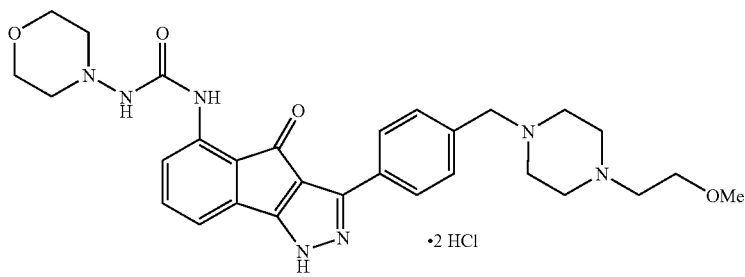

Synthesis of N-[3-(4-{[4-(2-methoxyethyl)-piperazinyl]methyl}phenyl)-4-oxoindeno-[2,3-d]pyrazol-5-yl](morpholin-4-ylamino)-carboxamide dihydrochloride
(compound B16)

Acetic acid (5.76 g, 96 mmole) was added to a suspension of aldehyde (10 g, 24 mmole) and piperazine (6.91 g, 48 mmole) in NMP (150 mL). The reaction was stirred at room temp for 16 h then treated with NaB(OAc)$_3$H (12.7 g, 60 mmole). The reaction was stirred at room temp for 20 h during which time the reaction becomes very viscous. 1N NaOH (200 mL) was then added and the reaction was stirred for 1 h. The reaction was then poured onto H$_2$O (750 mL) and filtered. The solid was washed with H$_2$O (2×350 mL), EtOH (100 mL), and Et$_2$O (200 mL). The solid was then dried under vacuum to yield the desired amine as the free base (9.98 g, 76%). The free base was then suspended in EtOH (200 mL) and heated to boiling. The suspension was then treated with 4N HCl in dioxane (15 mL). The suspension clears then after ~15 min, a thick precipitate forms. Additional EtOH (200 mL) was added to facilitate stirring. Once the suspension cooled to room temp, it was filtered and the solid was washed with EtOH (200 mL) and Et$_2$O (200 mL). The solid was then dried under vacuum to yield the desired bis-hydrochloride salt (10.3 g) designated compound B16.

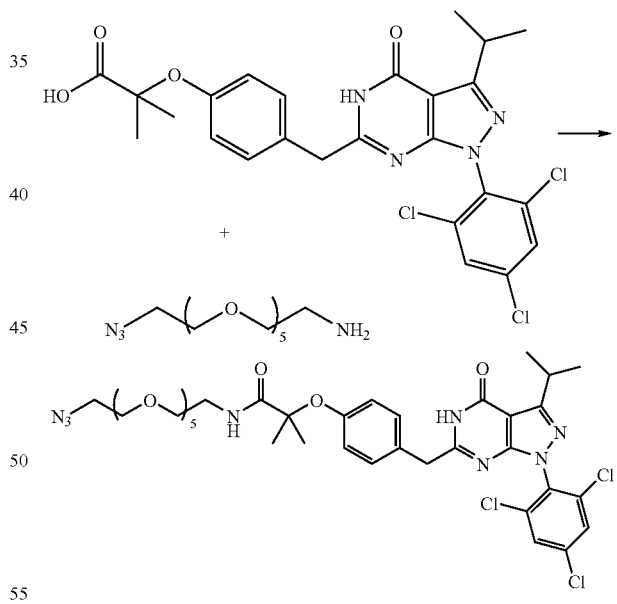

Synthesis of Compound R

To a solution of acid (1.4 g, 2.5 mmol) and amine (0.8 g, 2.6 mmol) in DMF (10 mL) was added DIEA (0.8 mL, 4.6 mmol) followed by HBTU (1.5 g, 4 mmol). The reaction mixture was stirred at room temperature for 24 h, poured into an ethyl acetate/1 N NaOH partition. Aqueous layer extracted with ethyl acetate. Organic extracts washed with 1 N HCl, dried and concentrated to give an oil. The crude oil was purified by silica gel chromatography to give the product azide as a colorless oil (0.9 g).

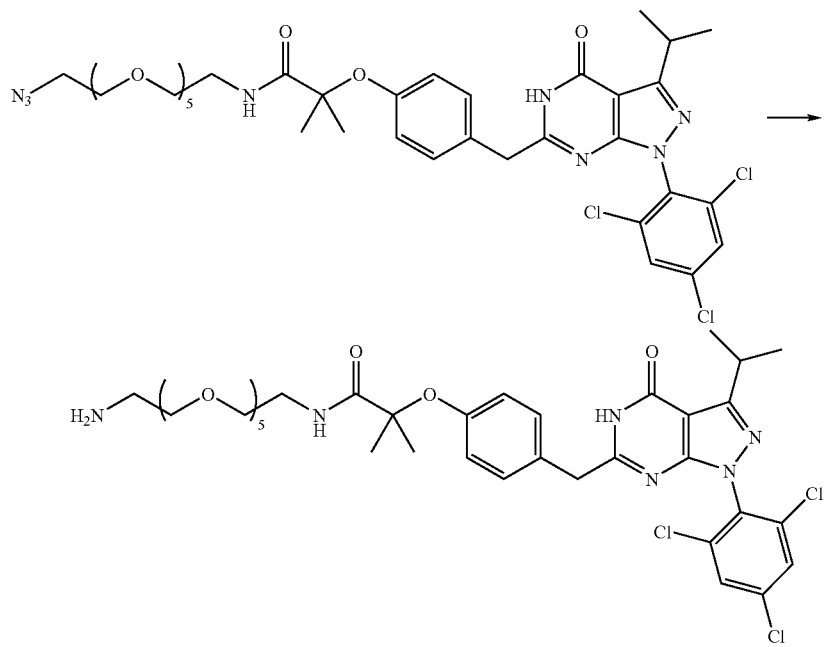

The azide (0.9 g, 1 mmol) was dissolved in THF/water (10/0.5 mL). Ph₃P (0.45 g, 1.7 mmol) was added and reaction was allowed to stir overnight at room temperature. The reaction mixture was poured into 50% NaOH solution and extracted with ethyl acetate. The organic extracts were dried and concentrated. A hydrochloride salt was made with 3 N HCl in isopropanol. The solid (Compound R hydrochloride) was taken up in MeOH and precipitated with ether. The solid was filtered and dried to give the product (0.79 g).

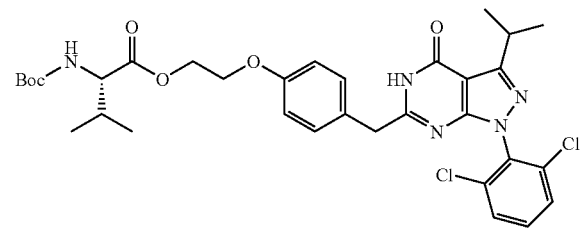

Synthesis of 2-(4-{[1-(2,6-dichlorophenyl)-3-(methylethyl)-4-oxo-5-hydropyrazolo[5,4-d]pyrimidin-6-yl]methyl}phenoxy)ethyl (2S)-2-[(tert-butoxy)carbonylamino]-3-methylbutanoate To a solution of 1-(2,6-dichlorophenyl)-6-{[4-(2-hydroxyethoxy)phenyl]methyl}-3-(methylethyl)-5-hydropyrazolo[5,4-d]pyrimidin-4-one (4.1 g, 8.7 mmol) in DMF (40 mL) at room temp was added Boc-Val-OH (2.82 g, 13 mmol), EDC (2.5 g, 13 mmol), 1-hydroxybenzotriazole (2.0 g, 13 mmol), and diisopropylethylamine (2.3 mL, 13 mmol). The resulting solution was then stirred at ambient temp for 24 h then partitioned between EtOAc (250 mL) and 1 N HCl (200 mL). The organic layer was then washed with sat. aq. NaHCO₃ (200 mL), H₂O (200 mL), and brine (200 mL). The organic layer was then dried (MgSO₄), filtered, and evaporated. The crude product was then purified by flash column chromatography (40% EtOAc/hexanes as eluent) to yield the desired product (5.7 g, 98%).

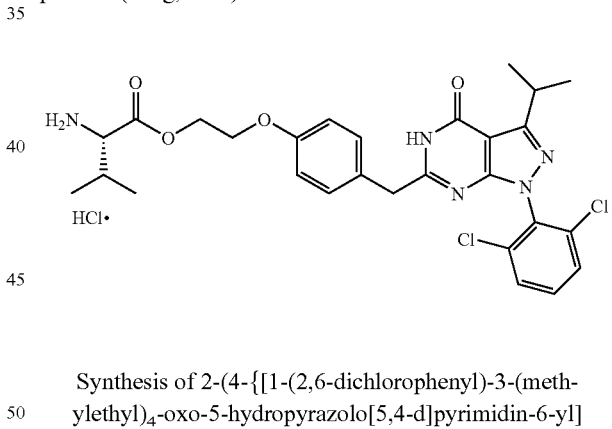

Synthesis of 2-(4-{[1-(2,6-dichlorophenyl)-3-(methylethyl)₄-oxo-5-hydropyrazolo[5,4-d]pyrimidin-6-yl]methyl}phenoxy)ethyl (2S)-2-amino-3-methylbutanoate To a solution of 2-(4-{[1-(2,6-dichlorophenyl)-3-(methylethyl)-4-oxo-5-hydropyrazolo[5,4-d]pyrimidin-6-yl]methyl}phenoxy)ethyl (2S)-2-amino-3-methylbutanoate in dioxane (50 mL) was added 4 N HCl in dioxane (10 mL). The reaction was then stirred at ambient temp for 48 h then evaporated. The crude product was then suspended in boiling EtOAc (50 mL) and brought into solution with a minimum of THF. The product was then crystallized by adding hexanes and cooling to 0° C. The solid was then filtered, washed with hexane, and dried under vacuum to yield the desired HCl salt (4.6 g, 92%).

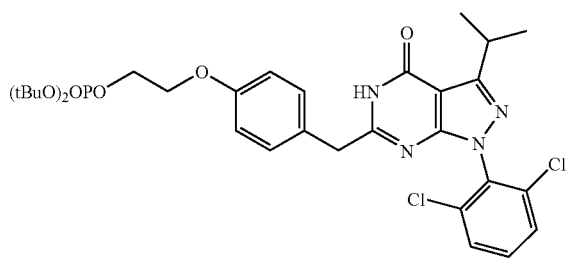

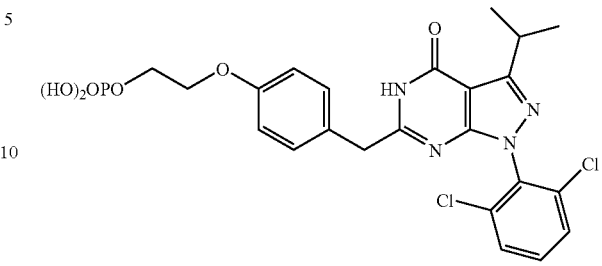

Synthesis of tert-butyl[2-(4-{[1-(2,6-dichlorophenyl)-3-(methylethyl)-4-oxo-5-hydropyrazolo[5,4-d]pyrimidin-6-yl]methyl}phenoxy)ethyl]phosphate To a solution of 1-(2,6-dichlorophenyl)-6-{[4-(2-hydroxyethoxy)phenyl]methyl}-3-(methylethyl)-5-hydropyrazolo[5,4-d]pyrimidin-4-one (4.0 g, 8.4 mmol) in DMF (25 mL) was added di-tert-butyl diisopropylphosphoramidite (4.8 mL, 15 mmol) followed by 1H-tetrazole (2.65 g, 38 mmol). The reaction was then stirred at ambient temp for 1 h then cooled to 0° C. and treated with a solution of mCPBA (3.2 g, 10.5 mmol) in CH$_2$Cl$_2$ (25 mL). The reaction was stirred at 0° C. for 30 min then partitioned between EtOAc (250 mL) and 10% aq. Na$_2$S$_2$O$_3$ (250 mL). The organic layer was washed with 10% aq. Na$_2$S$_2$O$_3$ (200 mL), sat. NaHCO$_3$ (150 mL), and brine (150 mL). The organic layer was then dried (MgSO$_4$), filtered, and evaporated. The crude product was suspended in boiling EtOAc (75 mL) and brought into solution with a minimum of THF. The product was then crystallized by adding hexanes and cooling to 0° C. The solid was then filtered, washed with hexane, and dried under vacuum to yield the desired phosphate (5.1 g, 91%).

Synthesis of 1-(2,6-dichlorophenyl)-3-(methylethyl)-6-({4-[2-(phosphonooxy)ethoxy]phenyl}methyl)-5-hydropyrazolo[5,4-d]pyrimidin-4-one Tert-butyl[2-(4-{[1-(2,6-dichlorophenyl)-3-(methylethyl)-4-oxo-5-hydropyrazolo[5,4-d]pyrimidin-6-yl]methyl}phenoxy)ethyl]phosphate was dissolved in 90% TFA/H$_2$O (50 mL) and stirred at ambient temp for 1 h then evaporated. The residue was azeotroped with toluene (2×100 mL) then dried under vacuum. The crude product was then triturated with boiling EtOAc (200 mL) and filtered. The solid was washed with hexanes (250 mL) and dried under vacuum to yield the desired product (4.2 g, 99%).

Synthesis of Other Compounds Disclosed Herein

Other compounds disclosed herein may be synthesized by methods analogous to those above, or by following the syntheses described below.

Scheme 6

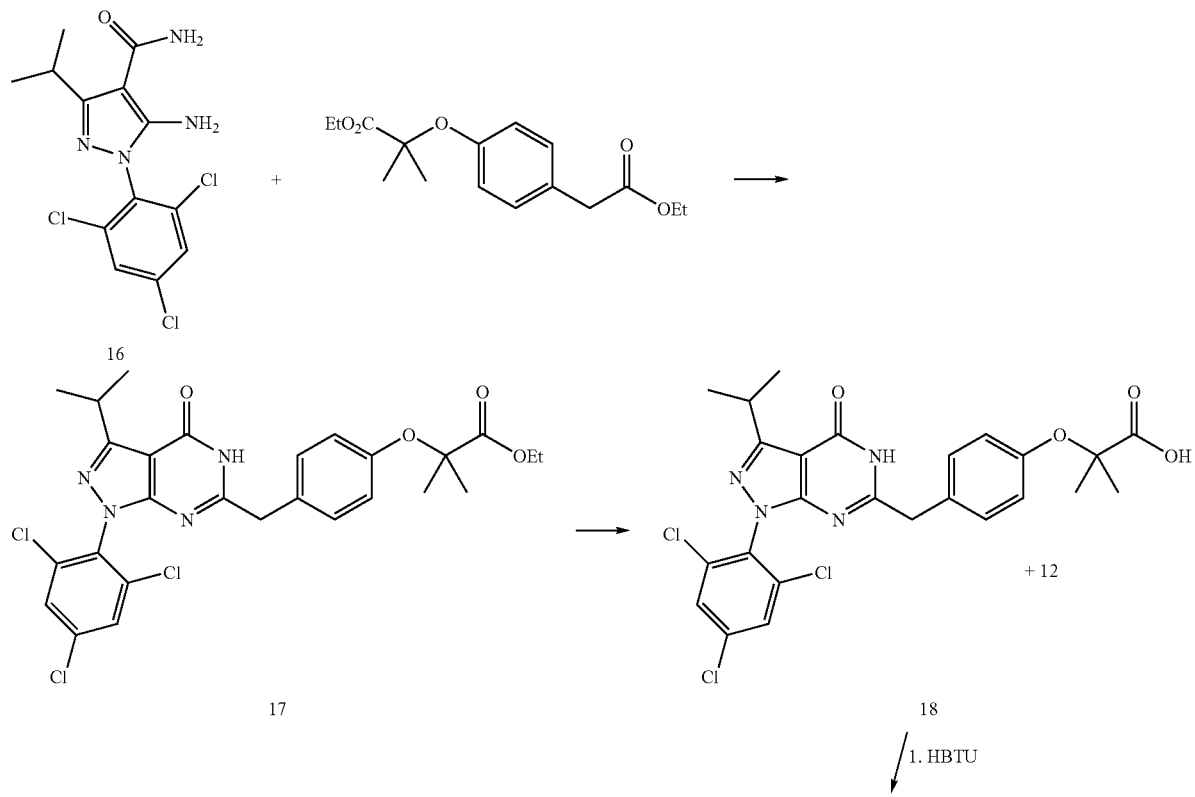

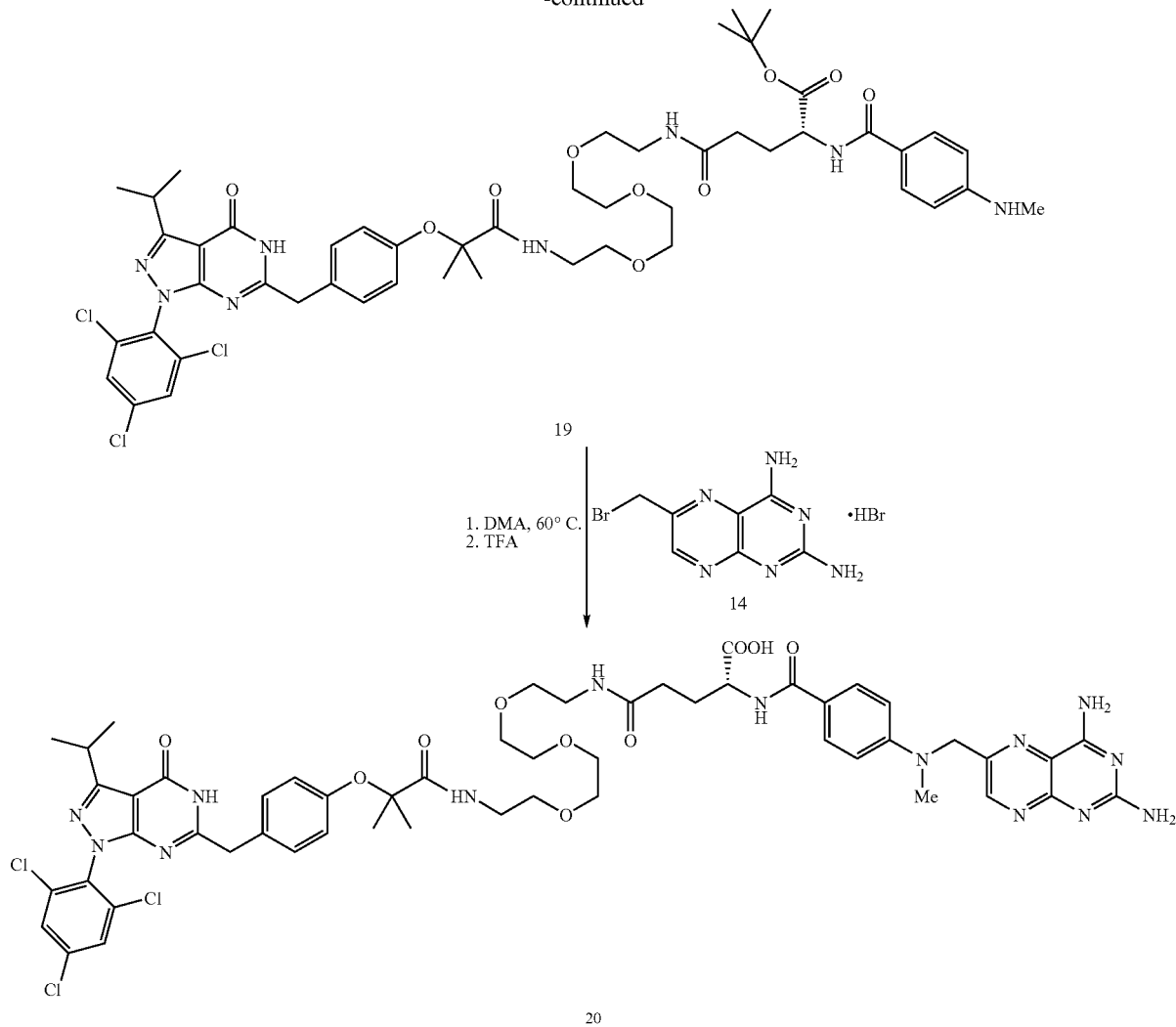

Synthesis of ethyl 2-methyl-2-(4-{[3-(methylethyl)-4-oxo-1-(2,4,6-trichlorophenyl)(5-hydropyrazolo[5,4-d]pyrimidin-6-yl)]methyl}phenoxy) propanoate (17; designated G1)

Compound 16 (2.5 g, 7.2 mmol; synthesized, for example, by Scheme A herein) and ethyl 2-{4-[(ethoxycarbonyl)methyl]phenoxy}-2-methylpropanoate (4.5 g, 15.3 mmol) were dissolved in 15 ml of ethanol and 5.8 ml of a 2.66M solution of sodium ethoxide in ethanol (15.3 mmol) was added. The reaction mixture was heated to reflux for 5 hours, cooled to room temperature and let stand overnight. The reaction mixture was then diluted with ethyl acetate and washed with water and brine, dried over magnesium sulfate, filtered and concentrated to 1.6 g (2.8 mmol, 38%) of a beige solid (compound 17) designated compound G1.

Synthesis of 2-methyl-2-(4-{[3-(methylethyl)₄-oxo-1-(2,4,6-trichlorophenyl)(5-hydropyrazolo[5,4-d]pyrimidin-6-yl)]methyl}phenoxy)propanoic acid (18)

Compound 17 (1.6 g, 2.8 mmol) was dissolved in 30 ml dioxane, 10 ml methanol and treated with 5 ml (5 mmol) of 1N NaOH. The reaction was stirred at room temperature overnight, then diluted with ethyl acetate and washed with 1N HCl and then brine. The organic layer was dried over magnesium sulfate, filtered and concentrated to a solid (1.4 g, 2.5 mmol, 91%, compound 18) designated G2.

Synthesis of tert-butyl (2R)-2-{[4-(methylamino)phenyl]carbonylamino}4-(N-{2-[2-(2-{2-[2-methyl-2-(4-{[3-(methylethyl)-4-oxo-1-(2,4,6-trichlorophenyl)(5-hydropyrazolo[5,4-d]pyrimidin-6-yl)]methyl}phenoxy)propanoylamino]ethoxy}ethoxy)ethoxy]ethyl}carbamoyl)butanoate (19)

Compound 18 (0.70 g, 1.3 mmol) and compound 12 (0.63 g, 1.2 mmol; synthesized as described below) were dissolved in dimethyl formamide and HBTU (0.75 g, 2 mmol) was added followed by diisopropylethylamine (0.5 ml, 2.9 mmol). The reaction mixture was stirred at room temperature for 3 days, diluted with ethyl acetate and then washed with 0.5N NaOH and brine. The organic layer was dried over magnesium sulfate, filtered and concentrated to an oil which was purified by flash silica chromatography (5 to 10% MeOH/EtOAc) to give 430 mg (0.41 mmol, 34%) of brown foam (compound 19).

Synthesis of (2R)-2-[(4-{[(2,4-diaminopteridin-6-yl) methyl]methylamino}phenyl) carbonylamino]4-(N-{2-[2-(2-{2-[2-methyl-2-(4-{[3-(methylethyl)-4-oxo-1-(2,4,6-trichlorophenyl)(5-hydropyrazolo[5,4-d]pyrimidin-6-yl)]methyl}phenoxy)propanoylamino]ethoxy}ethoxy)ethyl}carbamoyl)butanoic acid (20, designated G3)

Compound 19 (0.43 g, 0.41 mmol) was dissolved in 10 ml dimethyl acetamide and 0.27 g compound 14 (0.80 mmol; synthesis described below) was added to the reaction mixture as a solid. The reaction mixture was heated to 60° C. for 5 hours, then let cool to room temperature and 100 ml diethyl ether added. The supernatant was decanted off leaving a dark brown residue which was taken up in 10 ml of a cleavage cocktail (10:10:1:1 TFA:CH$_2$Cl$_2$: Me$_2$S: H$_2$O) and stirred for one hour. Solvent removed under reduced pressure, and the residue was purified by RPHPLC. Fractions containing the product were combined, concentrated to a small volume and lyophilized to yield a yellow solid (101 mg, 0.086 mmol, 21%, compound 20; designated G3).

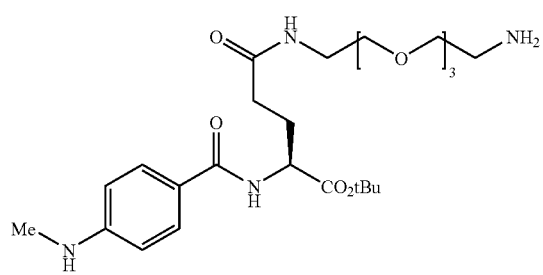

12

The synthesis of the linker moeity (12) and compound 14 were conducted as follows:

Synthesis of tert-butyl (2R)-4-[N-(2-{2-[2-(2-azido-ethoxy)ethoxy]ethoxy}ethyl)carbamoyl]-2-[(fluoren-9-ylmethoxy)carbonylamino]butanoate (103)

Fmoc-Glutamic acid a-tert-butyl ester (2.15 g, 5.1 mmol) was dissolved in 10 ml dimethyl formamide (DMF) and 1-amino-11-azido-3,6,9-trioxaundecane (1.0 g, 4.6 mmol) was added in 10 ml DMF. To this solution O-Benzotriazole-N,N,N'N'-tetramethyl-uronium-hexafluorophosphate (HBTU) (2.3 g, 6 mmol) and diisopropylethylamine (DIEA) (1.75 ml, 10 mmol) were added and the reaction stirred at room temperature for 2 hours. The reaction mixture was diluted with 100 ml ethyl acetate and the organic layer was washed with saturated sodium bicarbonate, 10% citric acid, and brine, and then dried over magnesium sulfate and concentrated to a brown oil. The crude product (compound 103) was purified by flash silica chromatography (2% MeOH in EtOAc) to yield a light brown oil, 2.3 g, 3.7 mmol, 80%.

Synthesis of tert-butyl (2R)-2-amino-4-[N-(2-{2-[2-(2-azidoethoxy)ethoxy]ethoxy}ethyl) carbamoyl] butanoate (104)

Compound 103 (2.7 g, 4.3 mmol) was dissolved in 30 ml methylene chloride and 30 ml diethylamine was added. The reaction mixture was stirred at room temperature for 2 h, and then concentrated to an oil under reduced pressure. The residue was dissolved with diethyl ether and ethyl acetate (ca. 50 ml ea.) and extracted with 10% citric acid. The aqueous layer was neutralized to pH13 with 10N NaOH and extracted with ethyl acetate. The organic layer was washed with brine, dried over magnesium sulfate and concentrated under reduced pressure to give 1.6 g of a brown oil, 4.0 mmol, 92% (compound 104).

Synthesis of tert-butyl (2S)$_4$-[N-(2-{2-[2-(2-azidoethoxy)ethoxy]ethoxy}ethyl)carbamoyl]-2-({4-[N-methyl(phenylmethoxy)carbonylamino]phenyl}carbonylamino)butanoate (111)

Compound 104 (0.81 g, 2.0 mmol) and 4-carboxybenzyl-methylaminobenzoic acid (compound 110) (0.61 g, 2.1 mmol) were dissolved in 10 ml DMF. To this solution, HBTU (1.0 g, 2.6 mmol) was added as a solid followed by DIEA (0.8 ml, 4.6 mmol). The reaction mixture was stirred overnight at room temperature, diluted with ethyl acetate and the organic layer was washed with 0.5N NaOH, brine, dried over magnesium sulfate and concentrated under reduced pressure to give a brown oil. The crude product was purified by flash silica chromatography (5% MeOH in EtOAc) to yield a brown oil (1.03 g, 1.5 mmol, 77%, compound 111).

Synthesis of tert-butyl (2S)-4-[N-(2-{2-[2-(2-aminoethoxy)ethoxy]ethoxy}ethyl)carbamoyl]-2-({4-[N-methyl(phenylmethoxy)carbonylamino]phenyl}carbonylamino)butanoate (12)

Compound 111 (1.0 g, 1.49 mmol) was dissolved in 50 ml MeOH and 130 mg 10% Pd/C added. The reaction mixture was shaken under 40 psi hydrogen for 16 hours, the catalyst was filtered off, and the filtrate was concentrated under reduced pressure to give 0.75 g (1.47 mmol, 98%) of a colorless oil (compound 12, linker moiety where n=3).

Synthesis of tert-butyl (2S)-4-(N-{2-[2-(2-{2-[2-(2-aminoethoxy)ethoxy]ethoxy}ethoxy)ethoxy]ethyl}carbamoyl)-2-{[4-(methylamino)phenyl]carbonylamino}butanoate (26)

Compound 26 (linker moiety where n=5) was synthesized by an analogous procedure as employed for compound 12, but using 1-amino-17-azido-3,6,9,12,15-pentaoxaheptadecane instead of 1-amino-11-azido-3,6,9-trioxaundecane in the first step of synthesis.

Synthesis of 2,4-diamino-6-(bromomethyl)pteridine hydrobromide (14)

Synthesis of 2,4-diamino-6-(bromomethyl)pteridine hydrobromide (compound 14) was carried out in two steps individually described in the literature (Taghavi and Pfleiderer, Tetrahedron Lett., 1997, 38:6835-36; Taylor and Portnoy, J. Org. Chem., 1973, 38:806).

Scheme 7

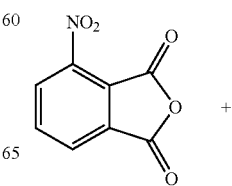

-continued

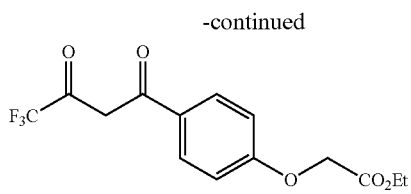

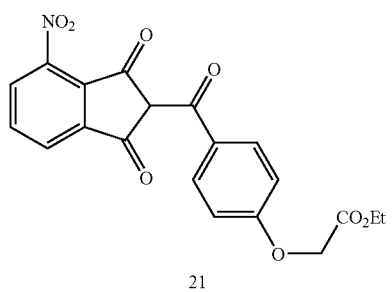
21

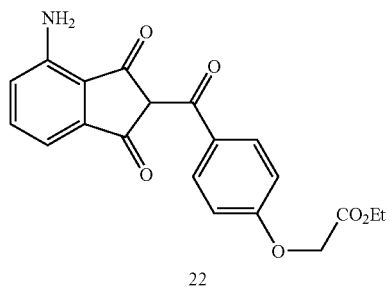
22

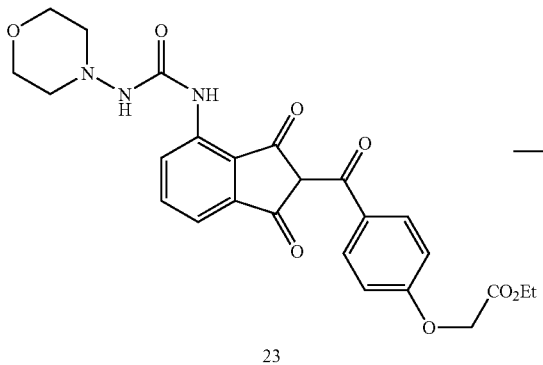
23

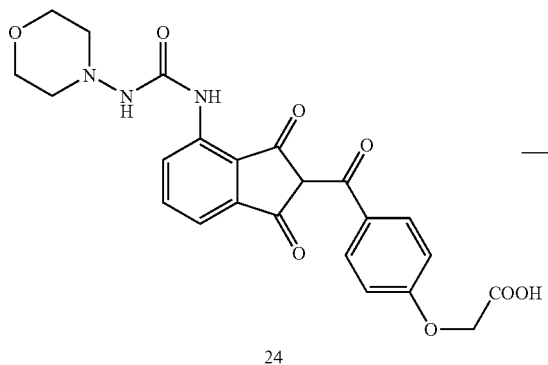
24

-continued

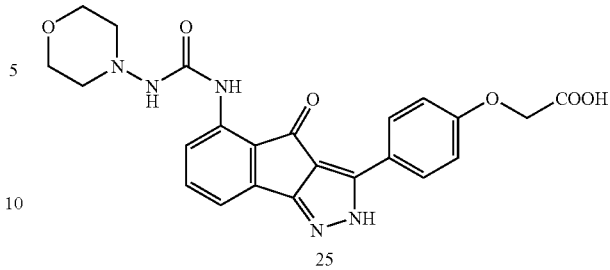
25

Synthesis of ethyl 2-{4-[(4-nitro-1,3-dioxo-2-hydrocyclopenta[3,4-a]benzen-2-yl)carbonyl]phenoxy}acetate (21)

Ethyl 2-[4-(4,4,4-trifluoro-3-oxobutanoyl)phenoxy]acetate (31.9 g, 0.1 mol) was combined with 19.3 g (0.1 mol) 3-nitrophthalic anhydride and 57 ml (0.6 mol) of acetic anhydride added. The slushy suspension was stirred at 0° C. and 28 ml (0.2 mol) triethyl amine added. The reaction mixture became homogenous and red and was stirred at room temperature overnight at which time 600 ml 1N HCl added. The resulting tacky suspension was stirred for 2 hours and the precipitate became a granular solid which was filtered off, resuspended in 200 ml ethanol, heated to reflux and then cooled to 0° C. A yellow solid was filtered off, washed with ethanol (3×40 ml) and dried to 12.7 g, 32 mmol, 32% yield (compound 21).

Synthesis of ethyl 2-{4-[(4-amino-1,3-dioxo-2-hydrocyclopenta[3,4-a]benzen-2-yl)carbonyl]phenoxy}acetate (22)

Compound 21 (12.7 g, 32 mmol) was partially dissolved in 600 ml ethyl acetate and 1.5 g of 10% Pd/C added. The reaction was stirred under a balloon of $H_2$ overnight. The balloon was recharged with $H_2$ and stirred for 24 hours more. The reaction was filtered through celite with the help of THF and $CH_2Cl_2$ to dissolve the product, and the filtrate was concentrated to 10.7 g (29.1 mmol, 91%) of solid (compound 22).

Synthesis of ethyl 2-[4-({4-[(morpholin-4-ylamino)carbonylamino]-1,3-dioxo-2-hydrocyclopenta[3,4-a]benzen-2-yl}carbonyl)phenoxy]acetate (23)

Compound 22 (6.4 g, 17.4 mmol) was combined in acetonitrile with 4-nitrophenyl morpholine-4-carboxylate (containing 1 eq. triethyl ammonium chloride impurity) (8.0 g, 19.8 mmol) and dimethylaminopyridine (0.20 g, 1.6 mmol) was added. The suspension was heated to reflux for 3 hours, cooled to 0° C. and a yellow solid filtered off. This solid was washed with a minimum of cold acetonitrile, and dried to 6.7 g, 13.5 mmol, 78% (compound 23).

Synthesis of 2-[4-({4-[(morpholin-4-ylamino)carbonylamino]-1,3-dioxo-2-hydrocyclopenta[3,4-a]benzen-2-yl}carbonyl)phenoxy]acetic acid (24)

Compound 23 (6.7 g, 13.5 mmol) was dissolved in 200 ml dioxane and 20 ml (20 mmol) 1N NaOH added. The reaction mixture was stirred for one hour. The white suspension was diluted with 1 l ethyl acetate and washed with 1N HCl and brine. The organic layer was dried over magnesium sulfate, filtered and concentrated to a yellow solid (6.3 g, 13.5 mmol, 100%, compound 24).

Synthesis of 2-(4-{5-[(morpholin-4-ylamino)carbonylamino]-4-oxoindeno[3,2-c]pyrazol-3-yl}phenoxy)acetic acid (25): compound G4

Compound 24 (6.5 g, 13.5 mmol) was dissolved in 200 ml THF, 100 ml DMSO and treated with 4 g (80 mmol) hydrazine hydrate and 190 mg, (1 mmol) p-toluenesulfonic acid hydrate. The reaction mixture was heated to 60° C. for 5 hours, let cool to room temperature and 600 ml $Et_2O$ added. The resulting suspension was then filtered, the precipitate washed with 1N HCl and dried under vacuum to yield 4.0 g (8.6 mmol, 64%) of yellow solid (compound 25) designated compound G4.

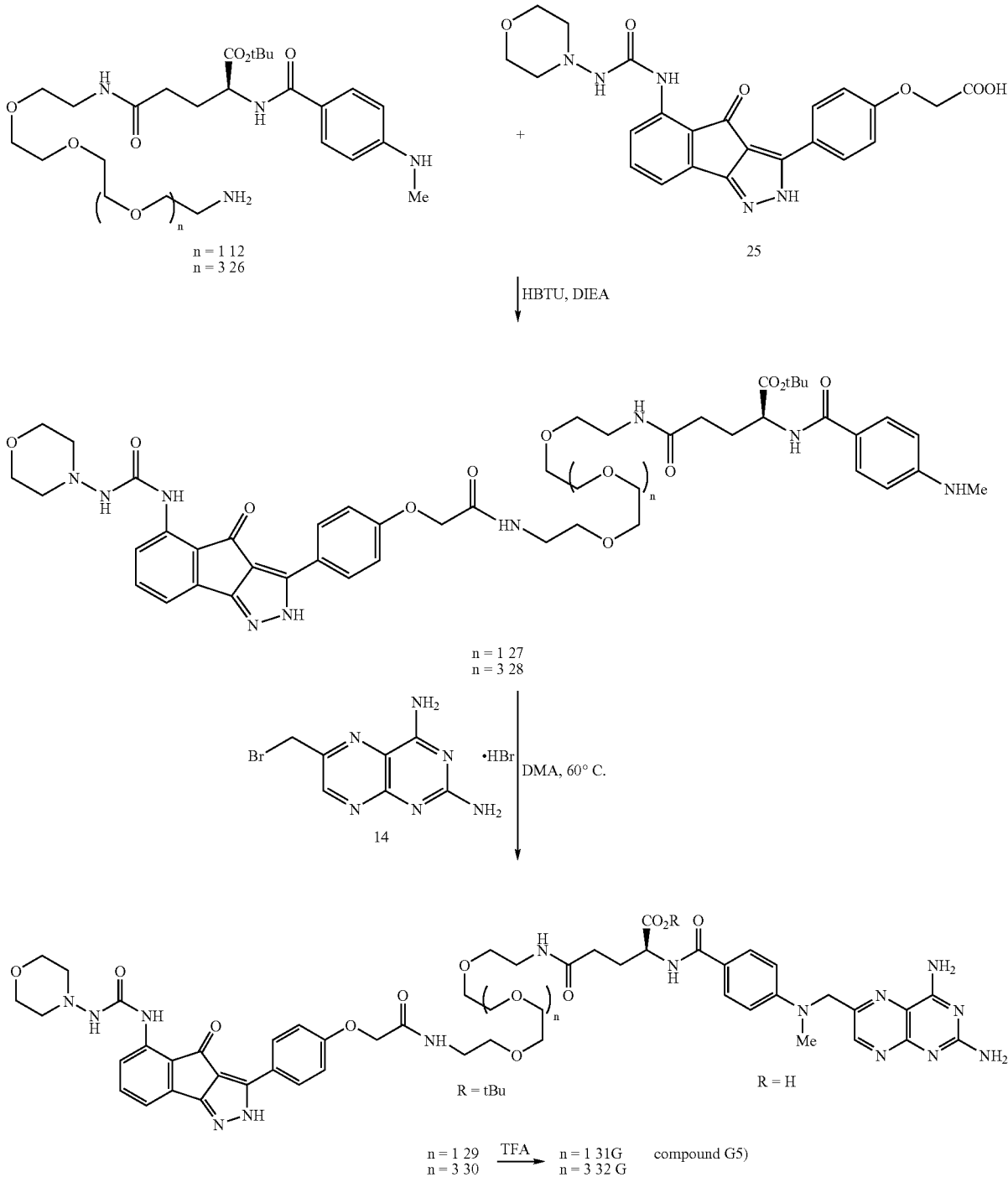

Synthesis of tert-butyl (2S)-2-{[4-(methylamino) phenyl]carbonylamino}-4-(N-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethyl}carbamoyl)butanoate (27)

Compound 12 (0.71 g, 1.4 mmol) and compound 25 (0.57 g, 1.2 mmol) were dissolved in 10 ml DMF and HBTU (0.8 g, 2.1 mmol) was added as a solid followed by DIEA (0.52 ml, 3 mmol). The reaction mixture was stirred at room temperature for 3 days, diluted with EtOAc and the organic phase washed with saturated $NaHCO_3$. The aqueous layer was back extracted with EtOAc twice and the combined organic layers dried over $MgSO_4$, filtered and concentrated to an oil. This oil was purified by flash silica chromatography (2 to 5% MeOH/EtOAc) to give an orange oil (0.50 g, 0.52 mmol, 44%, compound 27).

Synthesis of tert-butyl (2S)-2-{[4-(methylamino) phenyl]carbonylamino}-4-{N-[2-(2-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethoxy}ethoxy)ethyl]carbamoyl}butanoate (28)

Compound 25 (0.60 g, 1 mmol) and compound 26 (0.46 g, 1 mmol) were dissolved in 10 ml DMF and HBTU (0.7 g, 1.8 mmol) was added as a solid followed by DIEA (1.0 ml, 5.7 mmol). The reaction mixture was stirred at room temperature overnight, diluted with EtOAc and the organic phase washed with 0.5N NaOH, brine, dried over $MgSO_4$, filtered and concentrated to an oil. This oil was purified by flash silica chromatography (10 to 20% MeOH/EtOAc) to give a yellow foam (0.65 g, 0.62 mmol, 62%, compound 28).

Synthesis of tert-butyl (2S)-2-[(4-{[(2,4-diaminopteridin-6-yl)methyl]methylamino}phenyl) carbonylamino]-4-{N-[2-(2-{2-[2-(2-{4-[5-(methoxycarbonylamino)-4-oxoindeno[3,2-c]pyrazol-3-yl]phenoxy}acetylamino)ethoxy]ethoxy}ethoxy)ethyl]carbamoyl}butanoate (29)

Compound 27 (0.50 g, 0.52 mmol) was dissolved in dimethylacetamide and 0.33 g of compound 14 (1.0 mmol) was added to the reaction mixture as a solid. The reaction mixture was heated to 60° C. for 6 hours, then let cool to room temperature and 80 ml diethyl ether added. The supernatant was decanted off leaving a dark brown residue, which was purified by flash silica chromatography (5 to 10% MeOH/$CH_2Cl_2$ then 5 to 10% MeOH/$CH_2Cl_2$ w/1% $NH_4OH$) to give 0.33 g (0.29 mmol, 56%) of a yellow solid (compound 29).

Synthesis of tert-butyl (2S)-2-[(4-{[(2,4-diaminopteridin-6-yl)methyl]methylamino}phenyl) carbonylamino]-4-{N-[2-(2-{2-[2-(2-{2-[2-(4-{5-[(morpholin-4-ylamino)carbonylamino]-4-oxoindeno[3,2-c]pyrazol-3-yl}phenoxy)acetylamino]ethoxy}ethoxy)ethoxy]ethoxy}ethoxy)ethyl]carbamoyl}butanoate (30)

Compound 28 (0.65 g, 0.62 mmol) was dissolved in dimethylacetamide and 0.4 g of compound 14 (1.2 mmol) was added to the reaction mixture as a solid. The reaction mixture was heated to 60° C. for 6 hours, then let cool to room temperature and 80 ml diethyl ether added and let stand for 3 days. The supernatant was decanted off leaving a dark brown residue, which was purified by flash silica chromatography (5 to 10% MeOH/$CH_2Cl_2$ then 5 to 10% MeOH/$CH_2Cl_2$ W/1% $NH_4OH$) to give 0.45 g (0.37 mmol, 60%) of a yellow solid (compound 30).

Synthesis of (2S)-2-[(4-{[(2,4-diaminopteridin-6-yl)methyl]methylamino}phenyl)carbonyl-amino]-4-{N-[2-(2-{2-[2-(2-{4-[5-(methoxy-carbonyl-amino)$_4$-oxoindeno[3,2-c]pyrazol-3-yl]phenoxy}acetylamino)ethoxy]ethoxy}ethoxy)ethyl]carbamoyl}butanoic acid (31, compound G5

Compound 29 (0.33 g, 0.29 mmol) was treated with 20 ml of a cleavage cocktail (10:10:1:1 TFA:$CH_2Cl_2$: $Me_2S$: $H_2O$). After one hour, solvent removed and the residue purified by RPHPLC. Fractions containing the product were combined, concentrated to a small volume and lyophilized to yield a yellow solid (0.19 g, 0.18 mmol, 61%, compound 31) designated compound G5.

Synthesis of (2S)-2-[(4-{[(2,4-diaminopteridin-6-yl)methyl]methylamino}phenyl)carbonyl-amino]-4-{N-[2-(2-{2-[2-(2-{2-[2-(4-{5-[(morpholin-4-ylamino)carbonylamino]-4-oxoindeno[3,2-c]pyrazol-3-yl}phenoxy)acetylamino]ethoxy}ethoxy)ethoxy]ethoxy}ethoxy)ethyl]carbamoyl}butanoic acid (32)

Compound 30 (0.45 g, 0.37 mmol) was treated with 20 ml of a cleavage cocktail (10:10:1:1 TFA:$CH_2Cl_2$: $Me_2S$: $H_2O$). After one hour, the solvent was removed and the residue purified by RPHPLC. Fractions containing the product were combined, concentrated to a small volume and lyophilized to yield a yellow solid (0.23 g, 0.18 mmol, 49%, compound 32).

Scheme 9

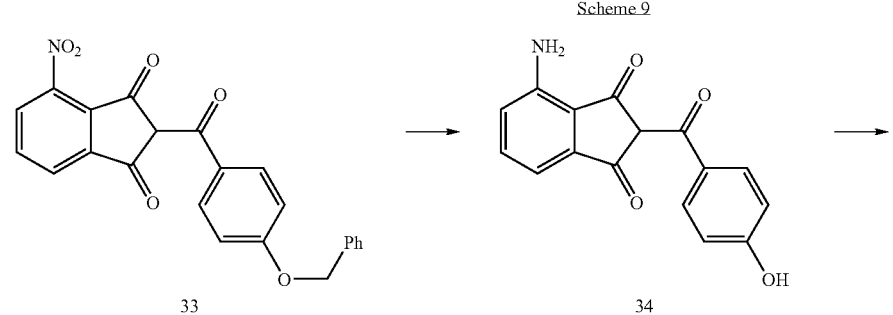

-continued
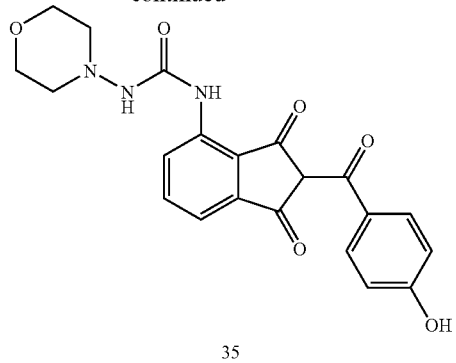
35
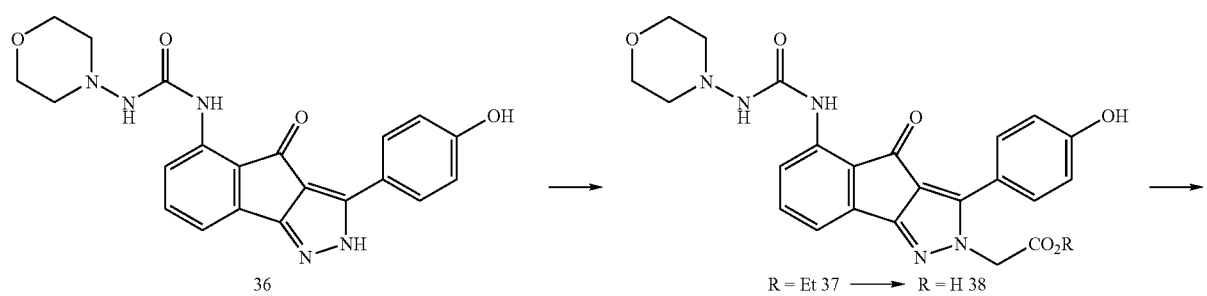
36 → R = Et 37 → R = H 38
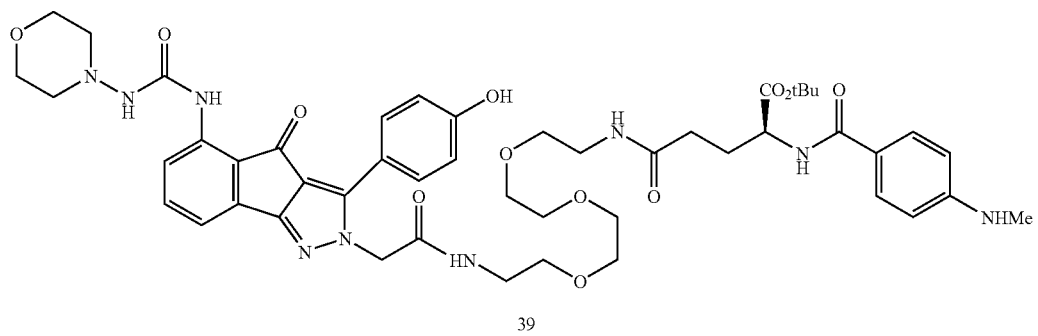
39
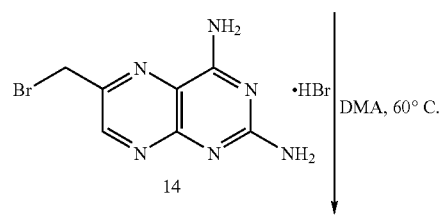
14
DMA, 60° C.
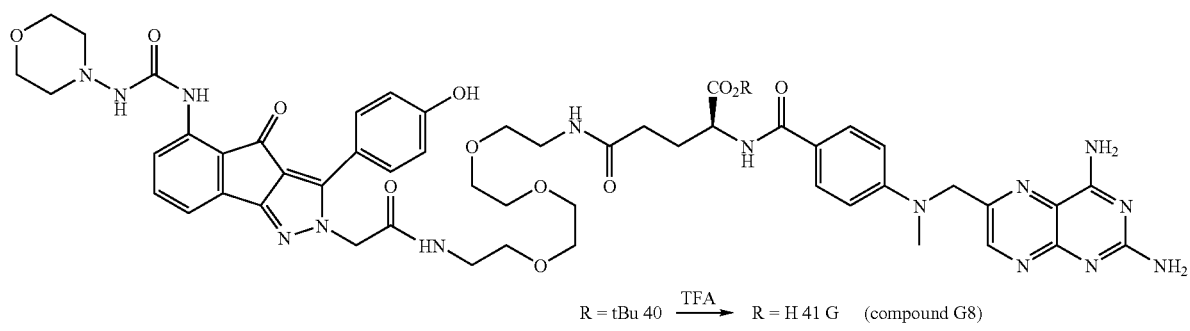
R = tBu 40 →TFA→ R = H 41 G (compound G8)

Synthesis of 1-(4-Benzyloxy-phenyl)-4,4,4-trifluoro-butane-1,3-dione

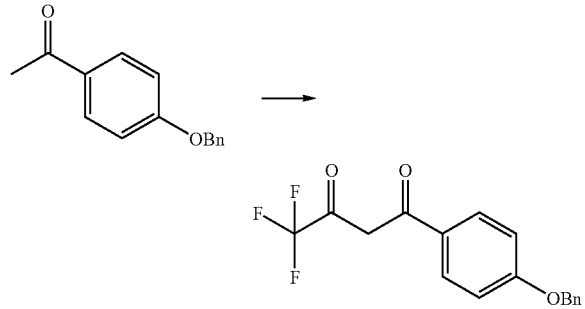

45.2 g 1-(4-Benzyloxy-phenyl) ethanone (200 mmol) was taken up in THF (250 mL) and treated with CF$_3$CO$_2$Et (30 ml, 250 mmol). The solution was cooled to 0° C. and treated with 2.66 M NaOEt (94 ml, 250 mmol) solution over 1 h. The ice bath was removed and the solution was stirred at room temperature for 4 h. The reaction was poured into 1N HCl (1000 ml) and extracted with EtOAc (1500 ml). The organic layer was washed with brine, dried and evaporated to yield 64.2 g 1-(4-Benzyloxy-phenyl)-4,4,4-trifluoro-butane-1,3-dione (200 mmol, 100% yield).

Synthesis of 4-nitro-2-[(4-hydroxyphenyl)carbonyl]-2-hydrocyclopenta[1,2-a]benzene-1,3-dione (33)

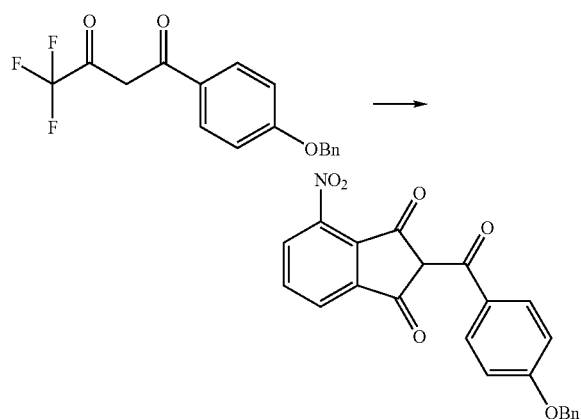

64 g 1-(4-Benzyloxy-phenyl)-4,4,4-trifluoro-butane-1,3-dione (200 mmol) was suspended in Ac$_2$O (114 mL, 1.2 mol) and treated with 3-nitrophthalic anhydride (28.6 g, 200 mmol). The suspension was cooled to 0° C. and treated slowly with Et$_3$N (56 ml, 400 mmol). The reaction was stirred at room temperature for 16 h, then poured into ice/3N HCl (500 ml) and stirred vigorously for 1 h. The precipitate was filtered and washed with water. The precipitate was suspended in boiling ethanol (450 ml) for 10 min, then cooled to 0° C. for 2 h and filtered. The solid was washed with cold ethanol and dried under vacuum to yield 34 g (72 mmol, 36% yield, compound 33).

Synthesis of 4-amino-2-[(4-hydroxyphenyl)carbonyl]-2-hydrocyclopenta[1,2-a]benzene-1,3-dione (34)

Compound 33 (32.1 g, 67.6 mmol) was dissolved in 1500 ml EtOAc and 3.2 g 10% Pd/C added. The reaction mixture was stirred under an atmosphere (balloon) of H$_2$ for 3 days. Methanol was added to aid dissolution and the reaction mixture was filtered through celite. The filtrate was concentrated to 19 g (67 mmol, 100%) of an orange solid (compound 34).

Synthesis of N-{2-[(4-hydroxyphenyl)carbonyl]-1,3-dioxo(2-hydrocyclopenta[2,1-b]benzen-4-yl)}(morpholin-4-ylamino)carboxamide (35)

Compound 34 (10.0 g, 35.3 mmol) was dissolved in acetonitrile with 4-nitrophenyl morpholine-4-carboxylate (containing 1 eq. triethyl ammonium chloride impurity) (13.0 g, 32.1 mmol) and dimethylaminopyridine (0.60 g, 5.4 mmol) was added. The reaction mixture was heated to reflux for 3 hours, cooled to room temperature and a pale green solid filtered off and dried to 7.5 g (18.3 mmol, 57%, compound 35).

Synthesis of N-[3-(4-hydroxyphenyl)-4-oxoindeno[3,2-c]pyrazol-5-yl](morpholin-4-ylamino)carboxamide (36; compound G6)

Compound 35 (7.5 g, 18.3 mmol) was suspended in 200 ml THF and hydrazine hydrate (4.5 g, 90 mmol) was added followed by p-toluenesulfonic acid hydrate (340 mg, 1.8 mmol). The reaction mixture was heated to reflux overnight (homogenous solution), let cool to room temperature and a precipitate formed, which was filtered off to give 1.2 g of product. The filtrate was concentrated to a solid, suspended in EtOAc and filtered. This solid was purified by flash silica chromatography (5 to 10% MeOH/EtOAc) to give 2.2 g more of product. The combined yield was 3.3 g, 8.4 mmol, 46% (36) designated G6.

Synthesis of ethyl 2-{3-(4-hydroxyphenyl)-5-[(morpholin-4-ylamino)carbonylamino]-4-oxoindeno[3,2-c]pyrazol-2-yl}acetate (37)

Compound 36 (2.2 g, 5.6 mmol) was dissolved in 50 ml acetone, 10 ml THF, and 10 ml DMF and Cs$_2$CO$_3$ (1.8 g, 5.6 mmol) was added followed by ethyl bromoacetate (0.93 g, 5.6 mmol). The reaction mixture was stirred for 2 hours, diluted with ethyl acetate, and the organic layer washed with 1N HCl, brine, dried over MgSO$_4$, filtered and concentrated to a yellow solid. The solid was purified by flash silica chromatography (2 to 3 to 4% MeOH/CH$_2$Cl$_2$) to give 1.2 g (2.4 mmol, 44%) of a yellow solid (compound 37).

Synthesis of 2-{3-(4-hydroxyphenyl)-5-[(morpholin-4-ylamino)carbonylamino]-4-oxoindeno[3,2-c]pyrazol-2-yl}acetic acid (38: compound G7)

Compound 37 (1.2 g, 2.4 mmol) was dissolved in 60 ml 3:2:1; dioxane:ethanol:DMSO and 12 ml 0.5 N NaOH added and the reaction became red. The reaction mixture was stirred at room temperature for one hour, diluted with EtOAc and washed with 1N HCl. The aqueous layer was back extracted once with ethyl acetate and the combined organic layers dried over MgSO4 and concentrated to an orange solid. The solid was triturated with 10 ml MeOH/100 ml Et$_2$O, filtered off and dried to a solid (1.1 g, 2.4 mmol, 100%, compound 38: designated G7).

Synthesis of tert-butyl (2S)₄-{N-[2-(2-{2-[2-(2-{3-(4-hydroxyphenyl)-5-[(N-morpholin-4-ylcarbamoyl)amino]-4-oxoindeno[3,2-c]pyrazol-2-yl}acetylamino)ethoxy]ethoxy}ethoxy)ethyl]carbamoyl}-2-{[4-(methylamino)phenyl]carbonylamino}butanoate (39)

Compound 38 (0.52 g, 1.1 mmol) and compound 12 (0.55 g, 1.1 mmol) were dissolved in DMF and HBTU (0.8 g, 2.1 mmol) was added as a solid followed by DIEA (0.52 ml, 3 mmol). The reaction mixture was stirred at room temperature overnight, diluted with EtOAc and the organic phase washed with saturated NaHCO₃, brine, dried over MgSO₄, filtered and concentrated to an oil. This oil was purified by flash silica chromatography (1 to 2 to 3 to 4 to 5% MeOH/CH₂Cl₂) to give a yellow foam (0.45 g, 0.47 mmol, 43%, compound 39).

Synthesis of tert-butyl (2S)-2-[(4-{[(2,4-diaminopteridin-6-yl)methyl]methylamino}phenyl)carbonylamino]-4-{N-[2-(2-{2-[2-(2-{3-(4-hydroxyphenyl)-5-[(N-morpholin-4-ylcarbamoyl) amino]-4-oxoindeno[3,2-c]pyrazol-2-yl}acetylamino)ethoxy]ethoxy}ethoxy)ethyl]carbamoyl}butanoate (40)

Compound 39 (0.45 g, 047 mmol) was dissolved in 8 ml dimethylacetamide and 0.2 g compound 14 (0.60 mmol) was added to the reaction mixture as a solid. The reaction mixture was heated to 60° C. for 6 hours, then let cool to room temperature and diethyl ether added. The supernatant was decanted off leaving a dark brown residue, which was purified by flash silica chromatography (5 to 10% MeOH/CH₂Cl₂ then 5 to 10% MeOH/CH₂Cl₂ w/1% NH₄OH) to give 0.32 g (0.27 mmol, 56%) of yellow solid (compound 40).

Synthesis of (2S)-2-[(4-{[(2,4-diaminopteridin-6-yl)methyl]methylamino}phenyl) carbonylamino]4-{N-[2-(2-{2-[2-(2-{3-(4-hydroxyphenyl)-5-[(N-morpholin-4-ylcarbamoyl)amino]-4-oxoindeno[3,2-c]pyrazol-2-yl}acetylamino)ethoxy]ethoxy}ethoxy)ethyl]carbamoyl}butanoic acid (41, compound G8)

Compound 40 (0.30 g, 0.27 mmol) was treated with 20 ml of a cleavage cocktail (10:10:1:1 TFA:CH₂Cl₂: Me₂S: H₂O). After one hour, solvent removed and the residue purified by RPHPLC. Fractions containing the product were combined, concentrated to a small volume and lyophilized to yield a yellow solid (78 mg, 0.073 mmol, 27%, compound 41: designated G8).

Assay Protocols and Results

The biological activity and utility of the compounds of the invention are demonstrated by one or more assays including those described in more detail below:

Assay 1. Inhibition of cell-cycle progression by the compounds of the invention using propidium iodide and BrdU assays (results shown in FIG. 1 and Table 2).

Assay 2. Reduced viability of a broad range of 60 cell-lines derived from various human tumors as represented by the NCI panel, on exposure to compounds of the invention (results shown in Table 3).

Assay 3. Irreversible effect of compounds of the invention on cells in a clonogenic survival assay (results shown in Table 3, FIG. 2 and FIG. 3).

Assay 4. Reduced viability of HCT-116 and IMR90 cells exposed to compounds of the invention as estimated using a Calcein AM assay (results shown in Tables 3 and 6).

Assay 5. Inhibition of viability in arrested tumor cells but not in arrested normal cells exposed to compounds of the invention (results shown in Table 4 and FIG. 4).

Assay 6. Inhibitory activity of compounds of the invention in certain kinase biochemical assays (results shown in Tables 5 and 6).

Assay 7. Activity of compounds in xenograft tumor models (results shown in FIGS. 6, 7 and 8).

Assay 8. Affinity of compounds to certain target proteins (results shown in FIG. 9).

Assay 9. Antiviral activity of compounds of the invention (results shown in Table 7).

Assay 1: Cell Cycle Analysis with Propidium Iodide and BrdU

The percentage of cells in the G1, S and G2/M phases of the cell cycle was determined by staining DNA with propidium iodide and quantifying the number of cells with a 2N or 4N DNA complement by flow cytometry. Alterations in the distribution of cells across the cell cycle in response to exposure to the Cdk inhibitors was evaluated in this manner.

Figures 1, 5A:
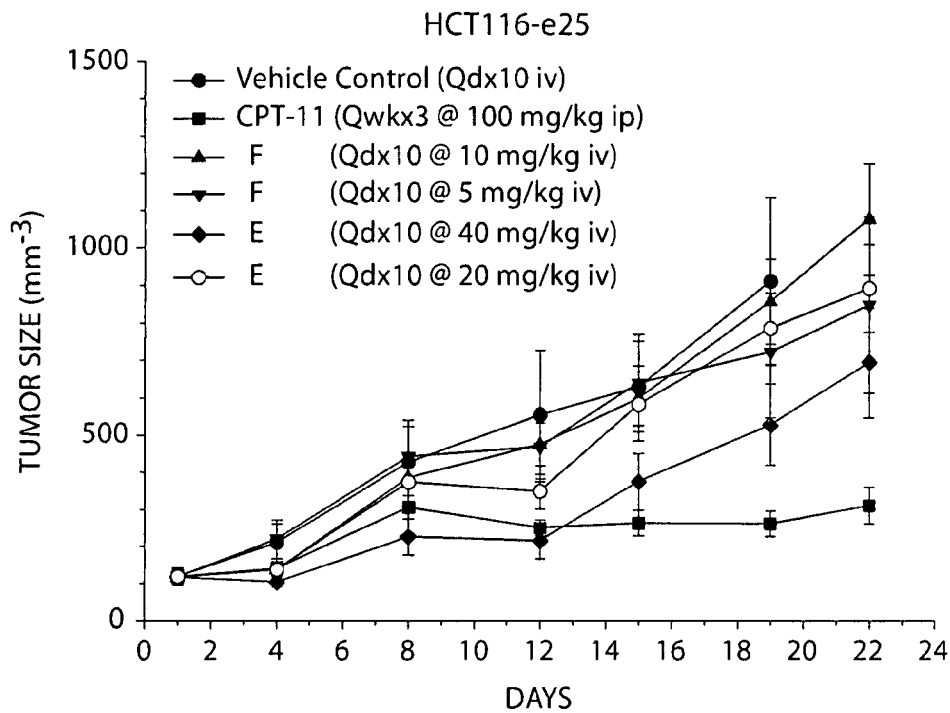

Method for Staining Cells with Propidium Iodide 3 sets of HCT-116 cells (100,000 cells/set) were cultured in the presence of a test compound in T-25 flasks according to Table 1 below. Analysis was performed at 24, 48 and 72 hours. Adherent cells were collected by trypsinization, combined with floating cells in Falcon 12×75 flow cytometric tubes, and harvested by centrifugation. The media was decanted from the cell pellet, 100 µl of PI stain was added and the cells were incubated at 37° C. for 20-25 minutes. The cell count was preferably no greater than $2\times10^6$-$4\times10^6$/ml. An equal volume (100 µl) of PI salt was then added to the cells, which were then incubated at 4° C. for 1-2 hours. The stained cells were analyzed on a Becton Dickinson FACScan flow cytometer. Samples were protected from light. FIG. 1 shows that on exposure to compound A37, cells are terminally arrested in G1 and G2, with evidence of apoptosis and endo-reduplication. Analogous results are seen for certain other compounds of the invention including compound B16.

Determination of BrdU Incorporation into DNA

This method measured the percentage of cells that incorporated the nucleotide analog, BrdU, into newly synthesized DNA as cells progressed through the S phase of the cell cycle. The inhibition of BrdU incorporation was used as a measure of a Cdk inhibitor's effect on S phase progression and DNA replication.

Method for BrdU Labeling 3 sets of HCT-116 cells (100,000 cells/set) were plated in T25 flasks and incubated with a test compound as above. Analysis was done at 24, 48, and 72 hours. BrdU was added to each T-25 flask from a stock of 10 mg/ml to a final concentration of 10 µM and the cells were incubated for an additional 16-18 hours at 37° C. The cells were then prepared for flow cytometric analysis according to manufacturer's protocol (BrdU Flow kit, BD-Pharmingen catalogue #2354KK) as follows:

Cells were harvested (adherent and floating) from the T25 flasks directly into Falcon 12×75 flow cytometric tubes as above followed by fixation and permeabilization with the addition of 100 µl of Cytofix/Cytoperm buffer (30 minutes, room temperature). The cells were then washed with 1 ml of Perm Wash buffer and the cell pellets were resuspended in 100 µl Cytoperm Plus buffer and incubated on ice for 10 minutes. The cells were then washed again with 1 ml of Perm Wash buffer and the fixation was repeated in 100 µl of Cytofix/Cyto Perm buffer for 10 minutes at room temperature. The cells were then washed with 1 ml of Perm Wash buffer. The cells were next treated for one hour at 37° C. with 100 µl DNase to expose incorporated BrdU followed by another wash step with 1 ml of Perm Wash buffer. The presence of incorporated BrdU was revealed with an α-BrdU-FITC antibody (50 µl of a 1:50 dilution of the antibody in Perm Wash buffer). Cells were protected from light and incubated at room temperature for 20-30 minutes. Following the incubation, the cells were washed with 1 ml of Perm Wash buffer, resuspended in 300 µl of 2% FBS in PBS, and analyzed on the flow cytometer. Results are presented in Table 2 as the concentration of compound (µM) that inhibits of BrdU incorporation by 50%.

Assay 2: Evaluation of Cdk Inhibitors in the NCI Panel of Human Tumor Cell Lines The evaluation of compounds at the National Cancer Institute in their panel of 60 cell lines provides a wealth of information regarding efficacy in a wide range of tumor types and genetic backgrounds. Included within this panel are cell lines derived from leukemia, melanoma and cancers of the lung, colon, brain, ovary, breast, prostate and kidney. Use of this panel provides a measure of the efficacy of compounds in cells with alterations in many genes that are associated with neoplastic transformation including p53 and Her2/Neu as well as those involved in metabolism and those which confer multi-drug resistance. The data generated in these cell lines with the protocol described below can be used to evaluate the activity of compounds.

Results of the NCI panel assays are presented in Table 3 (NCI panel) represented by two informative metrics: (a) the Mean-Graph Mid-point—the average IC50 over the whole cell panel except that an IC50 (µM) of less than 10 nM is calculated as being equal to 10 nM for this estimate; and (b) the IC50 (µM) of the inhibitory activity of the compound against an adriamycin resistant cell line (ADR-res).

Additional compounds of the invention showed the following activity in the NCI assay: (i) compound A37: Mean-Graph Mid-point <50 nM and IC50 of inhibition of growth of ADR-res cells <100 µM; (ii) compound B16: Mean-Graph Mid-point <50 nM and IC50 of inhibition of growth of ADR-res cells <10 µM.

Methodology of the In Vitro Cancer Screen

Cells were grown in RPMI-1640 10% FCS and plated in 96 well micro-titer plates at densities ranging from 5,000 to 40,000 cells/well. The plates were incubated for 24 hours at 37° C., 5% $CO_2$ for 24 hours. Media containing twice the desired final concentration of the compound (5 doses spanning 4 logs) was prepared and 100 µl was added to each well containing 100 µl media plus cells to yield the desired final concentration. The plates were then incubated for an additional 48 hours.

The effect of the compound on cellular viability was determined with the Sulforhodamine B (SRB) assay, which measures total protein. Cells were fixed with cold TCA to a final concentration of 10% and incubated at 4° C. for 60 minutes. The supernatant was discarded and the plates were washed five times with water and air-dried. SRB solution at 4% (w/v) in 1% acetic acid was added to each well and the plates were incubated for 10 minutes at room temperature. The plates were washed five times with 1% acetic acid and air-dried. The bound stain was solubilized with 10 mM trizma base and the absorbance was read on a plate reader at 515 nM.

Assay 3: Protocol for Clonogenic Survival Assay with HCT-116 Cells

This assay was used to determine the concentration of a compound that results irreversible loss of viability after a specified period of exposure. Essentially, cells are exposed to compound for a period of 1, 2 or 5 days, and are then transferred to compound-free growth medium. After continued incubation in the compound-free medium for a number of days, the number of colonies recovered is counted as an estimate of the number of surviving cells.

Figure 1A:
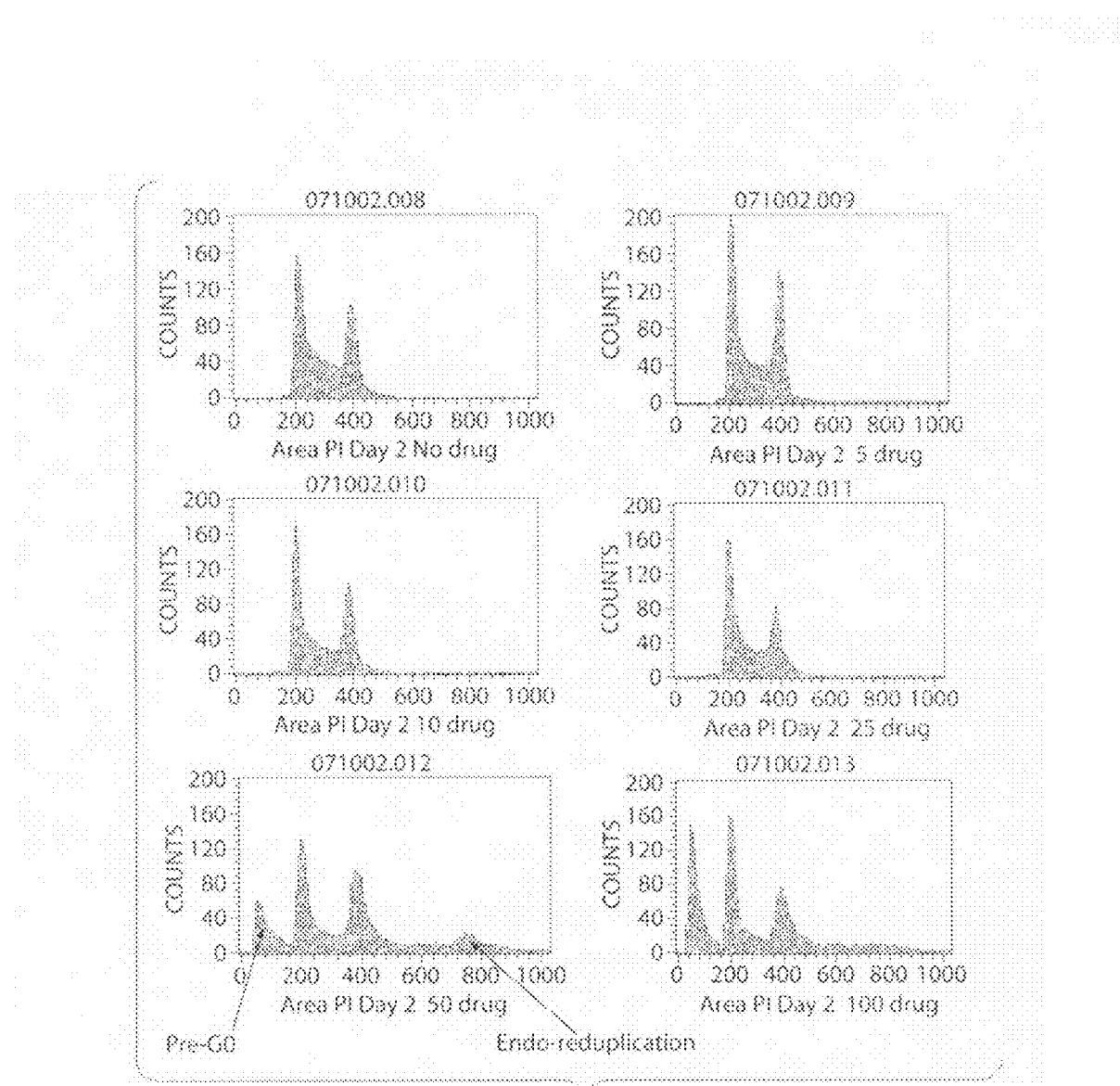
(FIG. 1A) cell-cycle analysis of HCT-116 cells by PI FACS analysis.
Figure 1B:
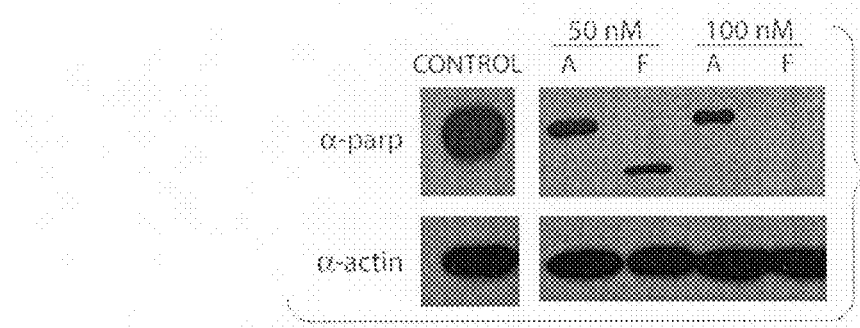
(FIG. 1B) induction of PARP cleavage.
Figure 2A:
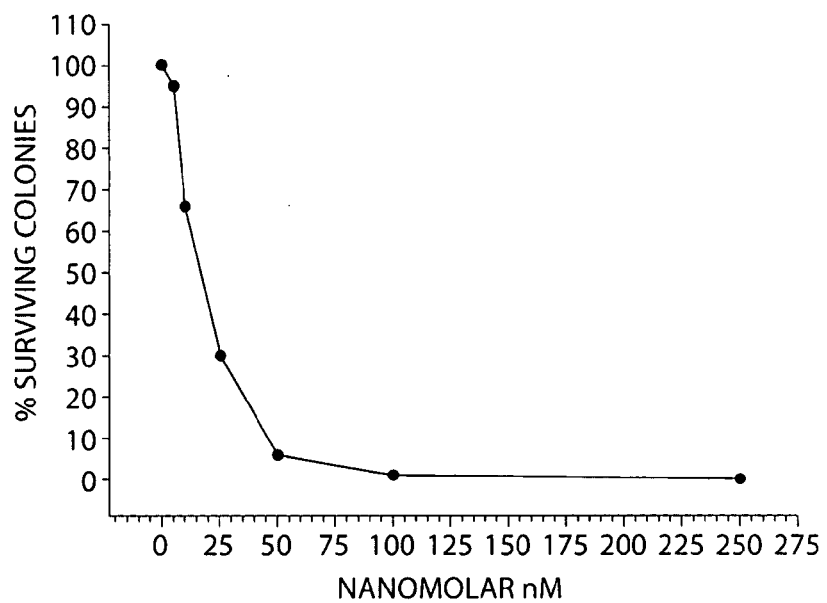
FIG. 2 illustrates the irreversible effect of compound A37 on clongeneic survival of HCT-116 tumor cells, as represented by (FIG. 2A) dose response.
(FIG. 2B) time-course.
Figure 2B:
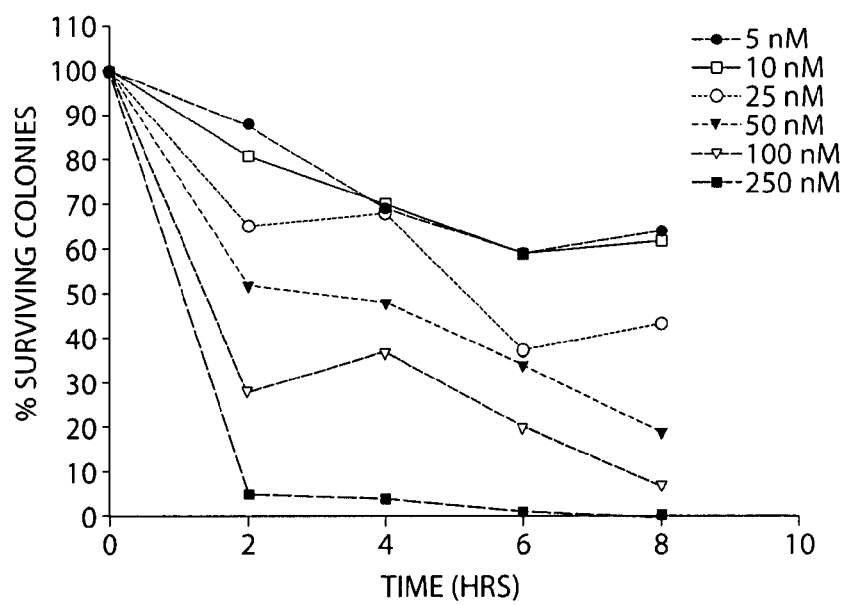
Figure 3:
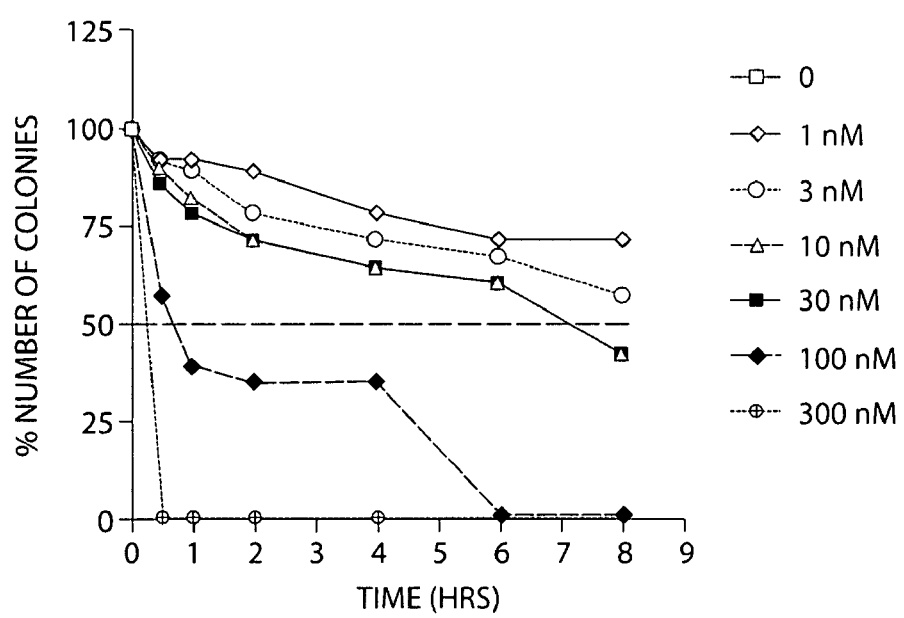
FIG. 3 depicts the irreversible effect of compound B16 on clongeneic survival of HCT-116 tumor cells, as represented by time-course.
Figures 2, 5A:
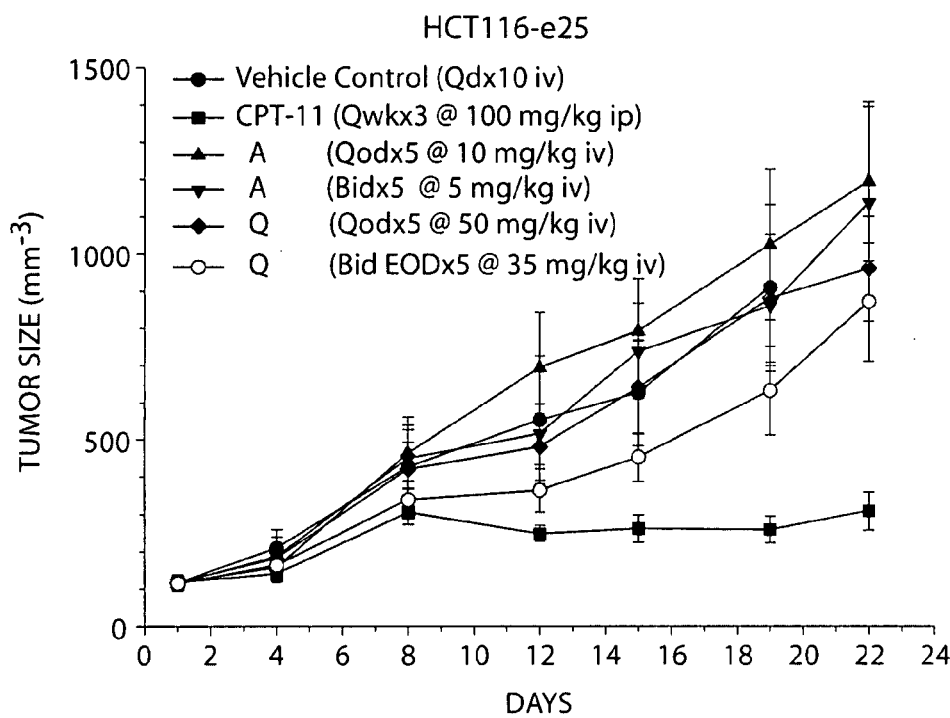
Figures 1, 5B:
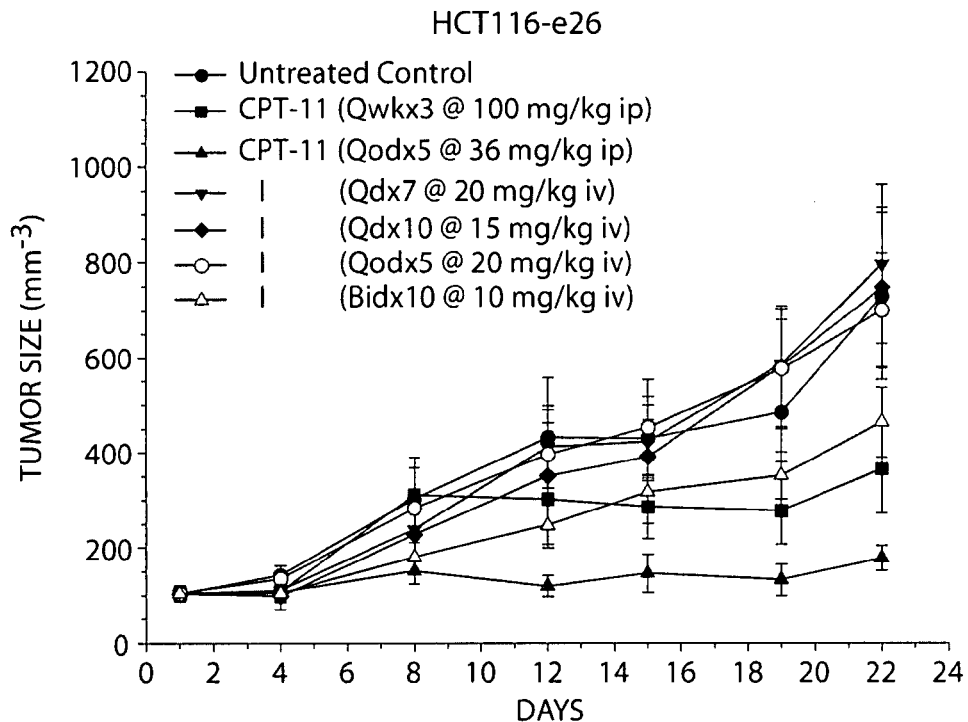
Figures 2, 5B:
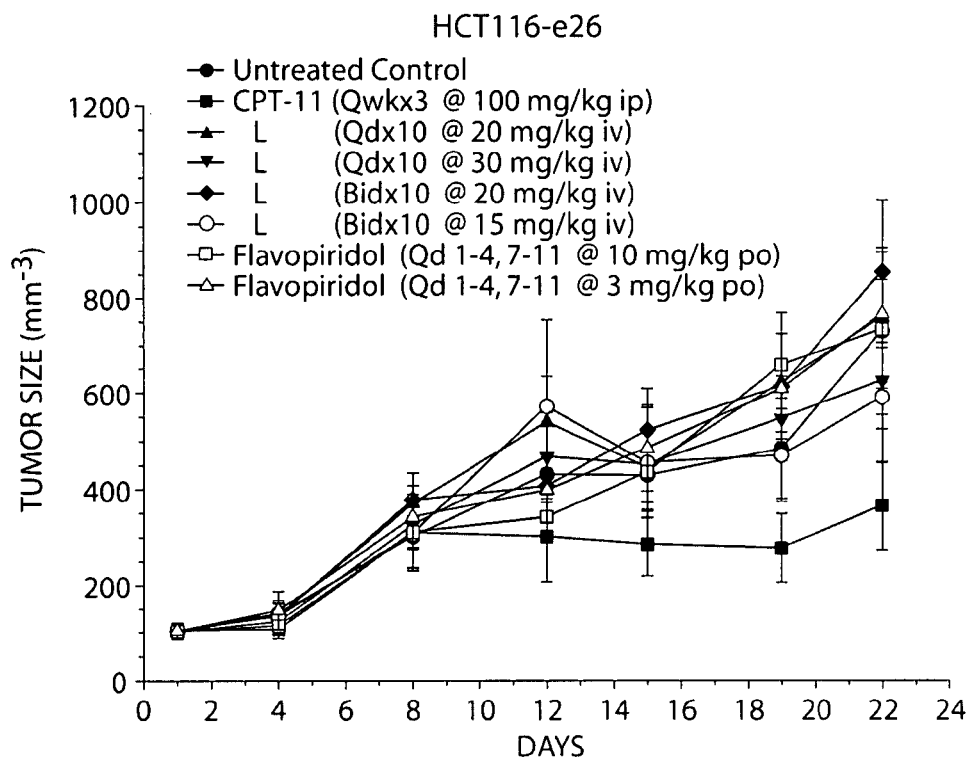
Figure 5C:
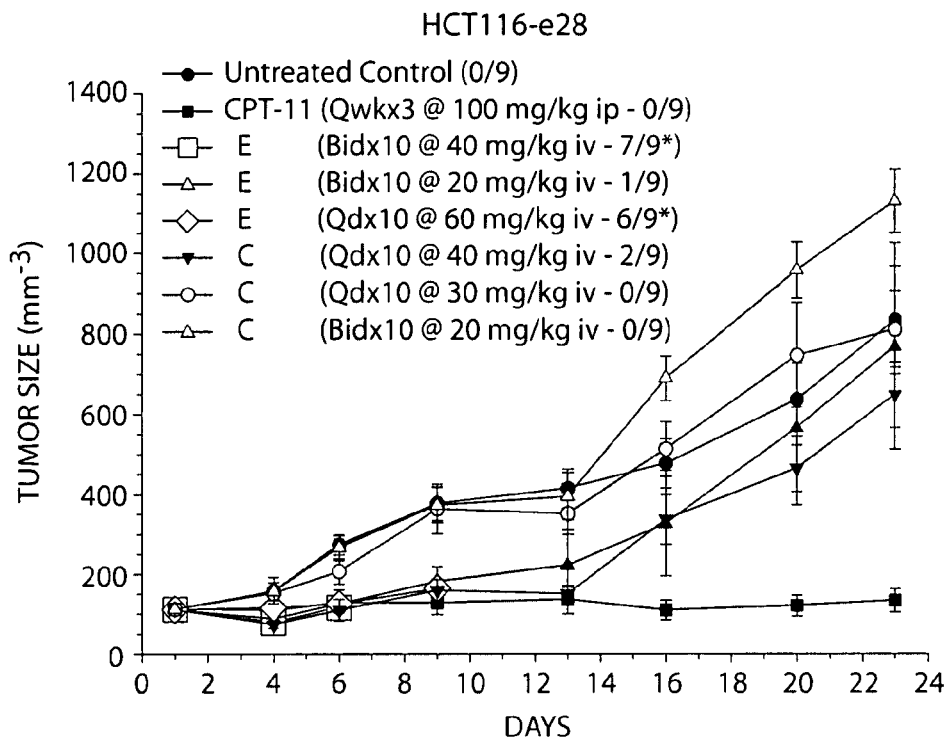
Figure 5D:
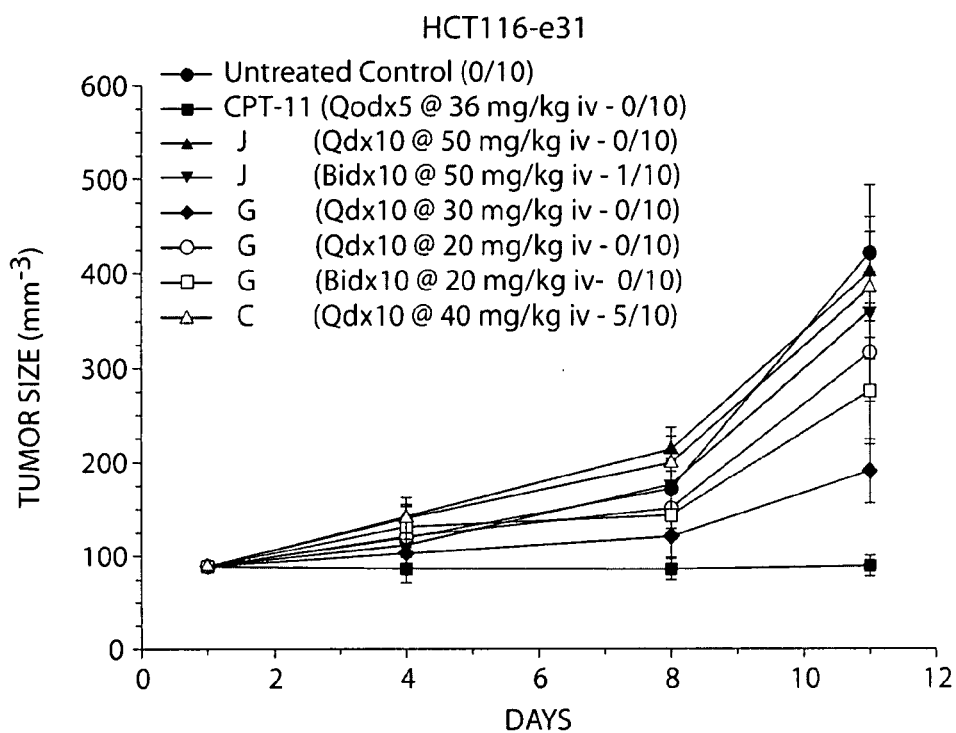
Figures 1, 5E:
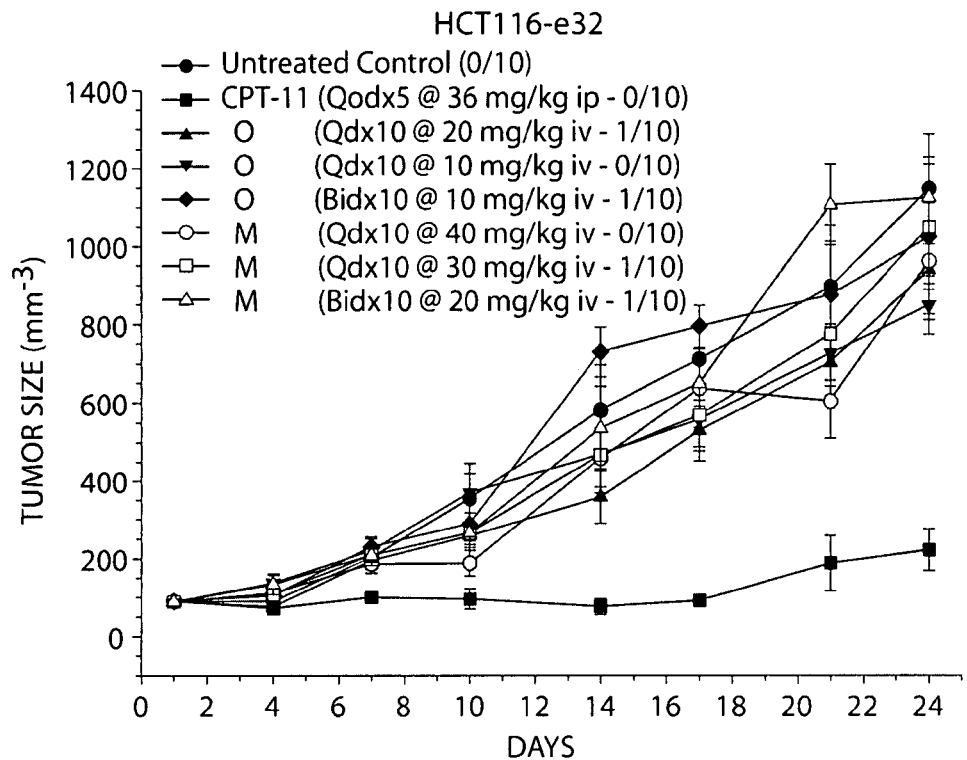
Figures 2, 5E:
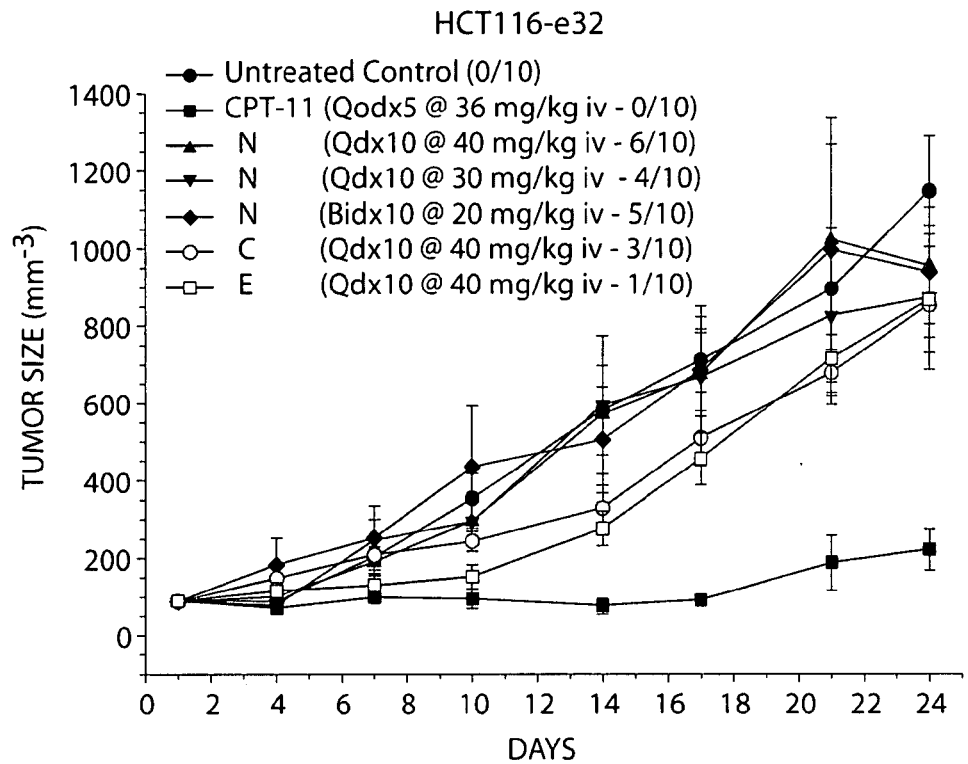
Figures 1, 5F:
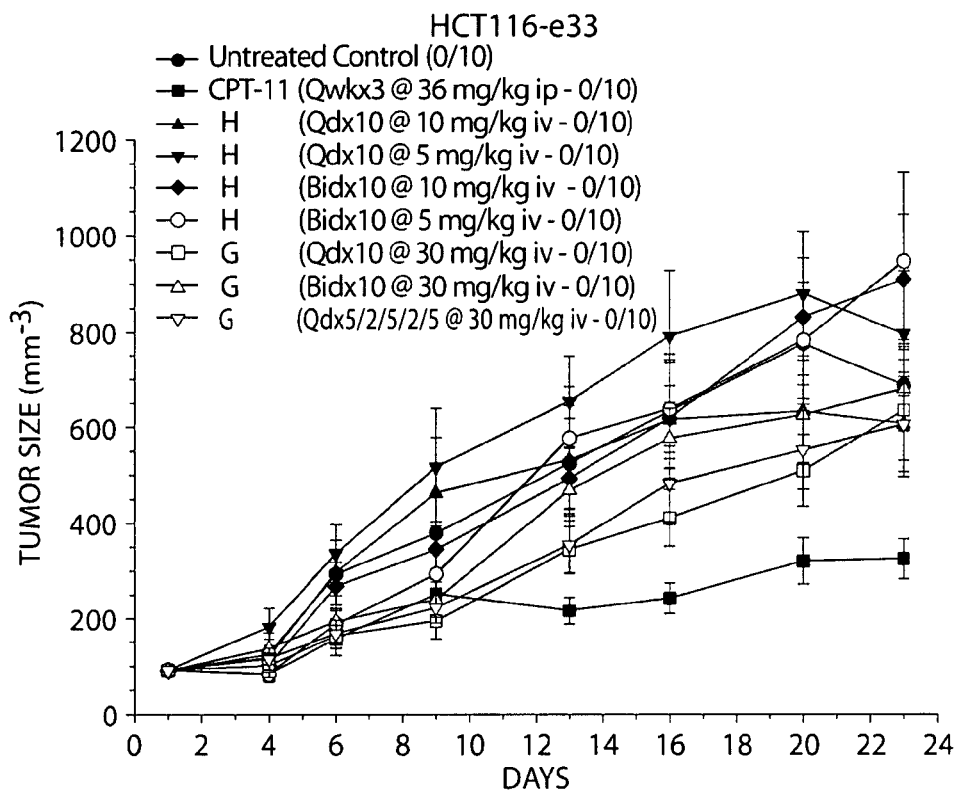
Figures 2, 5F:
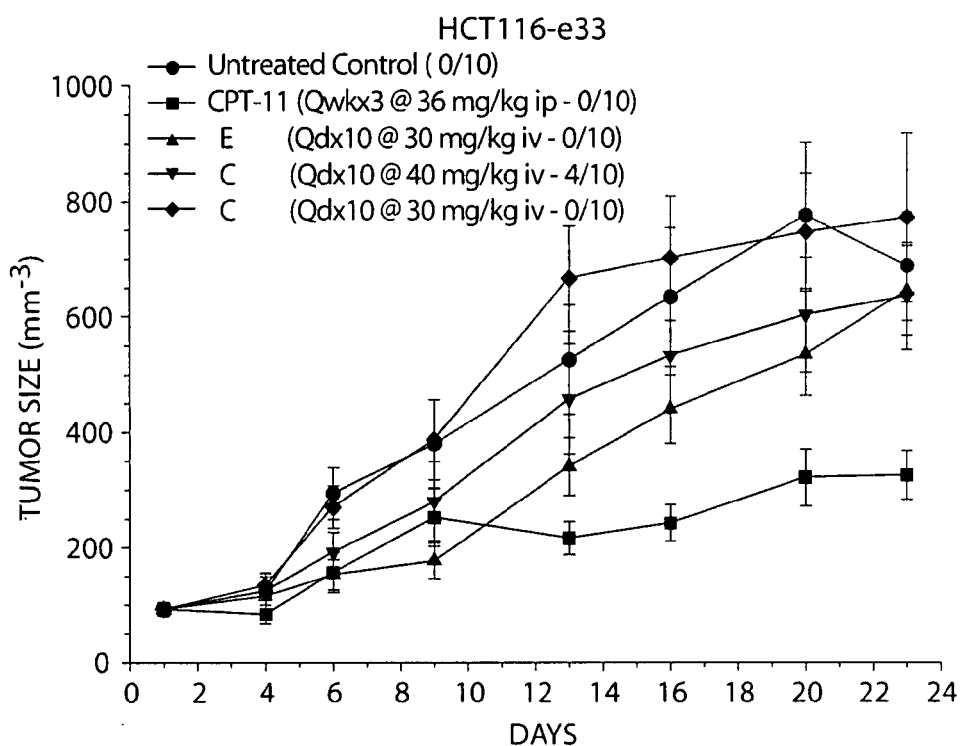
Figures 1, 5G:
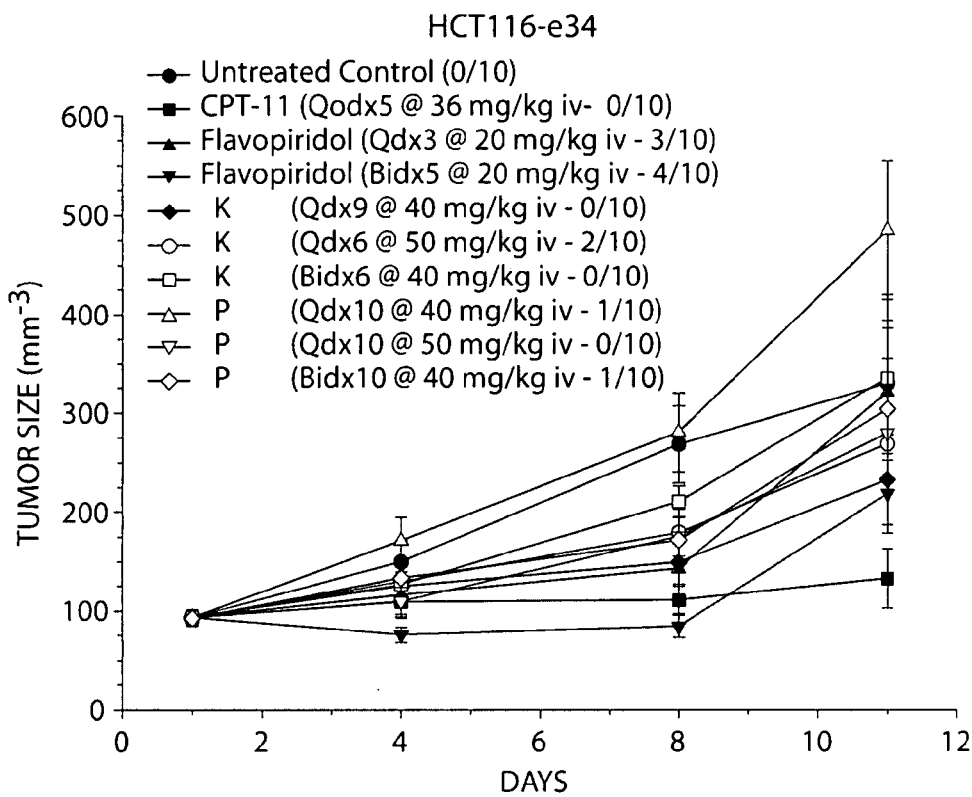
Figures 2, 5G:
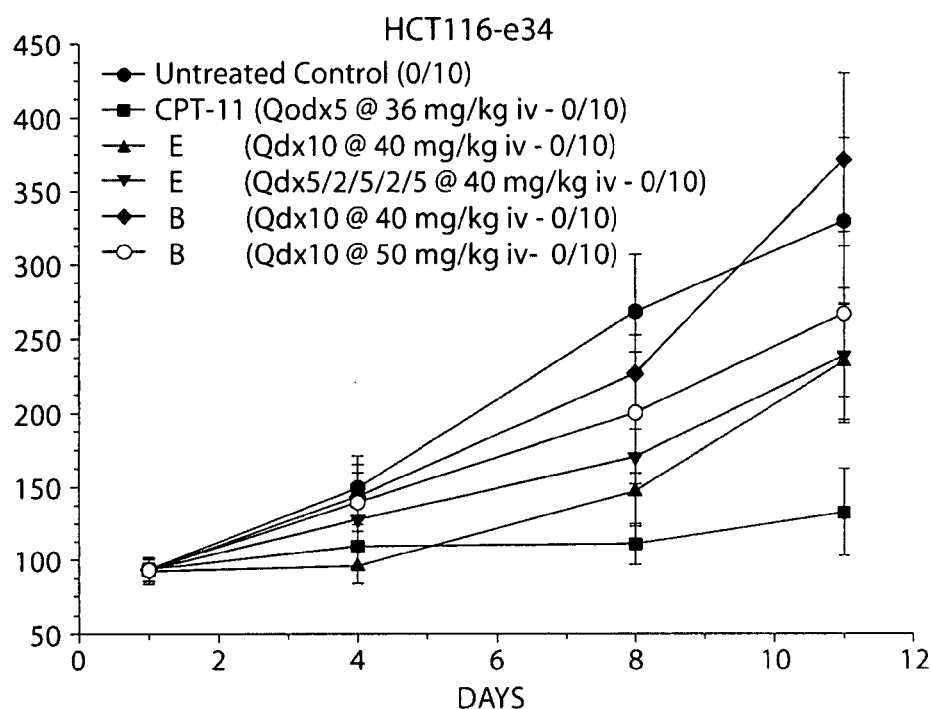

Results of such survival assays for various compounds of the invention are presented in Table 3 (clonogenic) as the concentration (µM) of compound that inhibits colony recovery by 50% (IC50). FIG. 2 displays irreversible inhibition of cellular activity in HCT-116 cells, and the time-course of such inhibition by compound A37, with an IC50 of <50 nM with 24 hour compound exposure. Compound B16 shows an IC50 of <100 nM in the same assay, and IC50 reached within 30 to 60 min at 100 nM (FIG. 3).

Method to Measure Cell Survival after Exposure to Compound

Media (RPMI-1640, 10% FCS, pen/strep) was prewarmed to 37° C. in a water bath. Cells were incubated and grown at 37° C., 5% $CO_2$. Cells were recovered by trypsinization from sub-confluent plates and counted using a hemocytometer. $1 \times 10^4$ cells were plated in 25 mls of media in a 15 cm tissue culture dish. 14 plates were set up for each test compound, and were incubated overnight at 37° C. The compound was diluted into media at 7 concentrations and the media on the cells was replaced with that containing the test compound. Two plates were set up for each concentration of the compound to be tested, as well as two control plates without compound. Plates were incubated as above for 24, 48 or 74 hours, media was removed and replaced with fresh media, and the plates were incubated an additional 7 days and washed with PBS. Colonies were stained with crystal violet solution (0.4% crystal violet, 20% ethanol) for 5 minutes, washed twice with distilled water, and counted.

Assay 4: Use of the Calcein AM Viability Assay for the Evaluation of Cdk Inhibitors in the Presence and Absence of Serum Proteins The potency of Cdk inhibitors, as measured by loss of cellular viability, was determined with the Calcein AM assay (Molecular Probes). Calcein AM is a substrate of intracellular esterases, which is cleaved only in viable cells to generate a fluorescent product that can be quantified with a fluorescent plate reader. The fluorescent signal is proportional to the number of viable cells, and thus loss of signal in response to the exposure of cells to Cdk inhibitors correlates with a loss of viability. This assay can distinguish cell cycle arrest, in which cells may still by viable, from loss of viability and is thus well suited for the evaluation of Cdk inhibitors. A compound that is a potent cytotoxic, may cause significant loss of cell viability in such assay.

Cellular $IC_{50}$'s were determined in the human colorectal carcinoma cell line, HCT-116, and the normal human fibroblast, IMR90. Protein adjusted $IC_{50}$'s were also determined in HCT-116.

Results of such viability assays are presented in Table 3 (HCT-116 (viability/protein adjusted) and IMR-90). IC50s (µM, non-protein adjusted) for the viability assay against HCT-116 cells are shown for further compounds of the invention in Table 6.

Analogous cell viability assays against other cell lines were conducted as above. The IC50 (µM) for other compounds of the invention were found to be: (i) compound A37: HCT-116 (<50 nM), HCT-116 protein-adjusted (<500 nM), A2780 (<10 nM), IMR90 (<50 nM); (ii) compound B16: HCT-116 (<10 nM), HCT-116 protein-adjusted (<500 nM), A2780 (<10 nM), IMR90 (<100 nM). Protocol for the Calcein AM viability assay.

HCT-116 or IMR90 cells were recovered from sub-confluent plates by trypsinization and 1,000 or 4,000 cells, respectively, were plated in 24-well dishes and incubated overnight at 37° C., 5% $CO_2$. HCT-116 cells were cultured in RPMI-1640, 10% FCS, and IMR90 cells were cultured in Minimum Essential Medium-alpha, 10% FCS. After overnight incubation to allow adherence, the media was aspirated from each well and replaced with media containing a test compound at a concentration from 0 to 250 nM, spanning a total of 7 doses. The plates were returned to the incubator and cultured for an additional 72 hours (3 days). The media used for the determination of protein-adjusted $IC_{50}$'s was RPMI-1640, 10% FCS, plus 1 mg/ml alpha acidic glycoprotein (Sigma G-9885), and 45 mg/ml human serum albumin (Sigma A3782). After 72-hours incubation with the test compound, the cells were washed twice with 1×PBS, taking special care to remove all residual buffer.

A 5 µM Calcein AM solution was prepared by dissolving a 50 µg aliquot of Calcein (Molecular Probes catalog # C3100) in 50 µl DMSO. After the Calcein had completely dissolved (10 minutes at room temperature), it was diluted into 10 ml PBS. Calcein/PBS (0.5 ml) was added to each well. The plates were incubated for 75 minutes at 37° C. (protected from light) and the fluorescent signal was read on a fluorescent plate reader (excitation 485/20 and emission 530/25).

Assay 5: Arrested Cell Assay

Cyclin-dependent kinase (Cdk) activity is required to promote the progression of cells through distinct phases of the cell division cycle. The proliferation of normal, non-transformed, cells in culture requires the presence of growth factors, the removal of which, through serum deprivation, leads to a loss of Cdk activity and consequent exit from the cell cycle as cells enter the quiescent phase, $G_0$. Therefore, from a mechanistic standpoint but without being bound by theory, Cdk inhibitors should have greatly reduced potency in arrested normal cells relative to their transformed counterparts.

Figure 4:
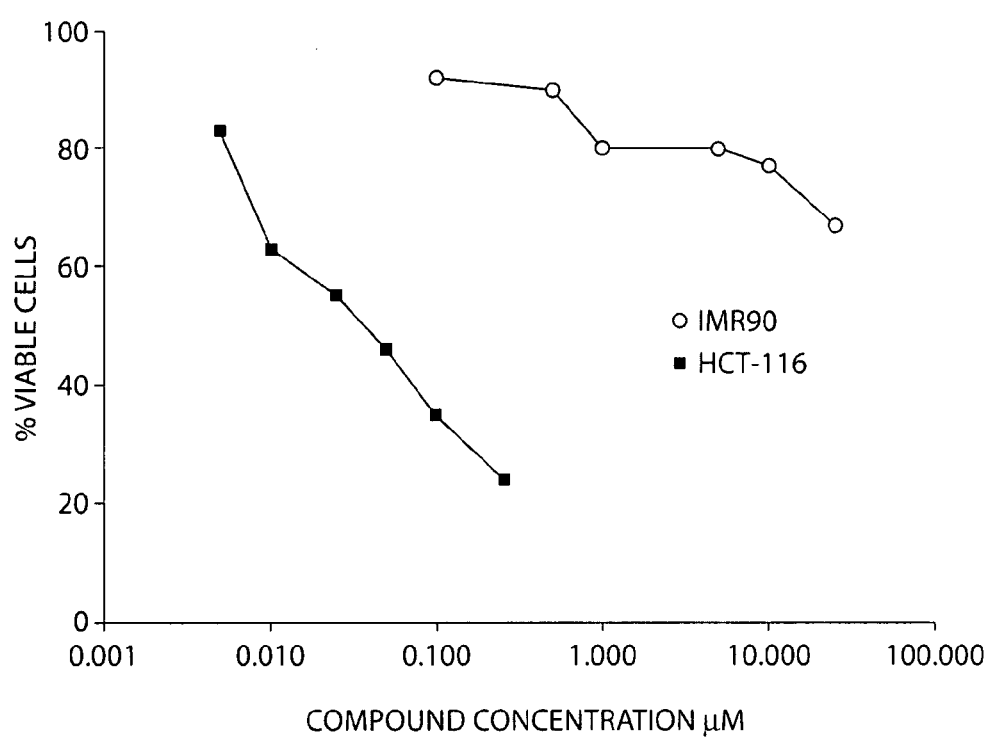
FIG. 4 shows reduced viability of arrested tumor (HCT-116) cells exposed to compound A37 compared to arrested normal (IMR90) cells exposed to the same compound.

Results of viability assays conducted on arrested normal (IMR90) and arrested tumor cells (HT-116) using certain compounds of the invention are presented in Table 4 below. FIG. 4 shows the enhanced activity of compound A37 on the inhibition of viability of arrested normal (IMR90) and tumor (HT-116) cells. The IC50 for compound A37 was found to be <50 nM for arrested HCT-116 cells, and >10 µM for arrested IMR90 cells. Compound B16 showed an IC50 of <50 nM for arrested HCT-116 cells and >10 µM for arrested IMR90 cells.

Arresting HCT-116 and IMR90 Cells by Serum Starvation for Evaluation of Compound Potency HCT-116 cells were plated in triplicate for each compound concentration to be tested in RPMI 1640 media containing 10% fetal calf serum at a density of either 200 or 2,000 cells per well in 24 well dishes, and incubated overnight at 37° C., 5% $CO_2$. The media from the plate containing 2,000 cells per well was removed, cells were washed once with serum free media and 1 ml of serum free media was placed on cells. The plates containing cells both in the presence and absence of serum were incubated for 6 additional days.

IMR90 cells were plated in triplicate for each compound concentration to be tested in MEM-A media containing 10% fetal calf serum at a density of either 2,000 or 20,000 cells per well in 24-well dishes and incubated overnight at 37° C., 5% $CO_2$. The media was removed from the 20,000 cell-per-well dish, cells were washed once with serum-free media, and serum-free media was placed on cells. The plates containing cells both in the presence and absence of serum were incubated for 3 additional days.

Assessing the Cell-Cycle Arrest of HCT-116 and IMR90 Cells by Serum Starvation

To ensure that the cells had indeed exited the cell cycle upon serum withdrawal, the percentage of BrdU positive cells, indicative of those progressing through S phase, was determined in each experiment. For the purpose of this experiment, cellular viability was evaluated simultaneously with the use of SNARF-1, a fluorescent substrate of intracellular esterases which are only active in viable cells. Together, the evaluation of BrdU incorporation and SNARF-1 cleavage by flow cytometry provided an assessment of the viability of arrested cells on a single cell basis. For this analysis, the cells were stained with SNARF-1 as follows and then prepared for determination of BrdU incorporation as described above.

HCT-116 and IMR90 cells were plated at the density described below in T25 flasks in serum-containing media (RPMI-1640 or MEM-α with 10% FCS, respectively). After 24 hours of growth, the media was removed and, after washing the cells, replaced with serum-free media.

HCT-116+FCS 5,000 cells
HCT-116−FCS 100,000 cells
IMR90+FCS 100,000 cells
IMR90−FCS 200,000 cells The IMR90 cells were grown for an additional 3 days and the HCT-116 cells were grown for an additional 6 days before pulsing with BrdU. A 50 µg aliquot of SNARF-1 (Molecular Probes catalog #C1272) was dissolved in 50 µl DMSO at room temperature for 10 minutes and then diluted into 10 ml PBS. The SNARF-1 was further diluted 1:64,000 before 200 µl was added to each tube of cells which had been cultured in the presence or absence of serum and pulsed with BrdU for 20 hours. The cells were incubated at 37° C. for 30 minutes and then washed with 3 ml of PBS.

These cells were then fixed and prepared for the measurement of BrdU incorporation as described above. The percentage of viable (FL-2) and BrdU positive (FL-1) cells was determined on a FACScan flow cytometer.

Assessing the Viability of Arrested HCT-116 and IMR90 Cells after Exposure to Compounds of the Invention The cells are incubated in the presence of the compounds for 72 hours (3 days) at 37° C. 5% $CO_2$ as follows to determine the potency of compounds on the cycling and arrested cells. Cycling and arrested HCT-116 cells as well as cycling IMR90 cells were exposed to a panel of 6 doses ranging from 5 to 250 nM. For arrested normal cells, the range of doses was increased to 50 nM to 25 µM, to compensate for the expected decrease in activity.

The effect of 72 hours of compound exposure on cellular viability was assessed in the Calcein AM assay. Calcein AM is a fluorescent substrate of intracellular esterases that are only active in viable cells. Cleavage of the substrate thus provides a measure of viability, which is proportional to cell number.

A Calcein AM stock solution was prepared by dissolving a 50 µg aliquot (Molecular Probes catalogue # C3100) in 50 µl DMSO. The tube was incubated at room temperature for approximately 10 minutes to ensure that the Calcein had dissolved completely. The calcein was diluted into 10 ml PBS to prepare the final solution, which was protected from light.

The media was aspirated off the cells, which were then washed twice with 1 ml PBS to remove the PBS completely from cells by aspiration. 0.5 ml of the Calcein/PBS solution was transferred by pipette into each well. The plates were incubated at 37° C. for 75 minutes (protected from light) and read on a fluorescent plate reader (excitation 485/20 and emission 530/25).

Assay 6: Inhibition of Biochemical Kinase Assay

Enzymes: Cdc2/cyclin B was obtained from commercial sources. Cdk2/his-cyclin $E_{short}$ was expressed in Sf9 cells. Cdk2/cyclin A, cdk4/cyclin D1, and cdk6/cyclin D2 were expressed in Sf9 cells. Protein kinase A (catalytic subunit, from bovine heart) and protein kinase C (mixed isozymes from rat brain) were obtained from commercial sources.

Substrates: Histone H1 was from commercial sources. GST-Rb is glutathione-S-transferase fused to the N-terminal of residues 379-928 of the Rb protein.

Assays: Cdc2/cyclinB activity was determined by measuring incorporation of radio-activity from adenosine [$\gamma$-$^{32}$P] triphosphate into Histone H1 using a TCA precipitation assay. Cdc2/cyclin B kinase and Histone H1 were obtained from commercial sources. The final assay solution contained 50 mM Tris.HCl, 10 mM $MgCl_2$, 1 mM dithiothreitol, 50 µM adenosine triphosphate, 2 µCi $^{32}$P, 10% dimethylsulfoxide (from compounds), pH 7.5, 20 µg Histone H1, 6 U enzyme in a 50 µL volume. Compounds were added at various concentrations between 1 nM and 10 µM. The reaction was started with the addition of enzyme, allowed to proceed for 20 min at 30° C., and stopped by the addition of 20 µL of stop solution (237 mM disodium ethylenediamine tetraacetate, 105 mM adenosine triphosphate, pH 8.0). The protein was precipitated by the addition of 35 µL 70% (w/v) trichloroacetic acid, and the precipitate was captured on a 96-well glass fiber filter plate (Millipore, Inc.), which had been wet with 25% (w/v) trichloroacetic acid. The filter was washed ten times with 25% (w/v) trichloroacetic acid, and the amount of incorporated $^{32}$P was determined by scintillation counting after adding 100 µL scintillant (Microscint 20, Packard Instruments). Relative activity was determined by dividing the amount of radioactivity incorporated in the presence of compound by the amount of radioactivity incorporated in a control experiment containing DMSO alone but no compound. The background radioactivity, determined in an experiment containing 50 mM EDTA in place of compound, was subtracted from all results before calculations. The concentration of compound for 50% inhibition ($IC_{50}$) was determined by fitting the data to the standard equation:

$$P = min + (max - min)(1/(1 + (IC50/[I])^s)) \qquad (1)$$

where P=1–relative activity is relative inhibition, [I] is concentration of compound, max and min are the maximum and minimum relative inhibition (1 and 0, respectively) and s is the so-called Hill slope.

Cdk2/cyclin E, Cdk2/cyclin A, Cdk4/cyclin D1, and Cdk6/cyclin D2 activity was determined using a glutathione-sepharose capture assay. The enzymes were expressed in Sf9 insect cells as heterodimers, and the substrate (GST-Rb) was glutathione-S-transferase fused to residues 379 to 928 of Rb retinoblastoma protein, expressed in E. coli. The assay solution contained 50 mM Tris.HCl, 10 mM $MgCl_2$, 1 mM dithiothreitol, 50 µM adenosine triphosphate, 2 µCi [$\gamma$-$^{33}$P]adenosine triphosphate, 10% dimethylsulfoxide (from compounds), pH 7.5, 40 µg GST-Rb, and enzyme in a 100 µL volume. Compounds were added at various concentrations between 1 nM and 10 µM. The reaction was allowed to proceed for 15 min at 30° C. and was stopped by the addition of 70 µL of stop solution (237 mM disodium ethylene-diamine tetraacetate, 105 mM adenosine triphosphate, pH 8.0). The GST-Rb was captured by binding to glutathione-sepharose bead (Amersham) for 110 min, and the suspension was filtered through a glass fiber filter. After washing the retained beads five time with phosphate-buffered saline containing 0.3% (w/v) Tween-20, the amount of $^{33}$P incorporated was determined by scintillation counting after adding 100 µL scintillant. Relative activity was determined by dividing the amount of radioactivity incorporated in the presence of compound by the amount of radioactivity incorporated in a control experiment containing DMSO alone but no compound. The background radioactivity, determined in an experiment containing 50 mM disodium ethylenediamine tetraacetate in place of compound, was subtracted from all results before calculations. The concentration of compound for 50% inhibition (IC o) was determined by fitting the data to equation (1).

Protein kinase C and protein kinase A were assayed using a TCA precipitation assay with Histone H1 as a substrate. For protein kinase A, the final assay contained 50 mM Tris, 10 mM $MgCl_2$, 1 mM dithiothreitol, pH 7.5, 12 µM adenosine triphosphate, 10% (v/v) dimethylsulfoxide (from compounds), 20 µg Histone H1, 2 µCi [$\gamma$-$^{32}$P] adenosine triphosphate, 0.2 U protein kinase A in a 100 µL assay. A protein kinase C assay contained 50 mM Tris, 10 mM $MgCl_2$, 1 mM dithiothreitol, 0.8 mM $CaCl_2$, pH 7.5, 5 µM adenosine triphosphate, 10% (v/v) dimethylsulfoxide (from compounds), 20 µg Histone H1, 2 µCi [$\gamma$-$^{32}$P] adenosine triphosphate, 0.01 U protein kinase C in a 50 µL assay. The assays were started by the addition of enzyme, allowed to react for 10 min at 30° C., and stopped by adding 0.4 volumes of 237 mM disodium ethylenediamine tetraacetate, 105 mM adenosine triphosphate, pH 8.0. The protein was precipitated from the stopped reaction by adding 0.5 volume 75% (w/v) trichloroacetic acid and captured by filtering through a 96-well glass fiber filtration apparatus (Millipore). The filters were washed ten times with 25% (w/v) trichloroacetic acid, and the amount of incorporated [$^{32}$P]phosphate was determined by adding 100 µl Microscint and scintillation counting. The concentration of compound for 50% inhibition ($IC_{50}$) was determined by fitting the data to equation (1).

Results from the above assays are presented in Table 5 and Table 6.

Assay 7: Xenograft Tumor Models

Drugs. Compounds of the invention were synthesized and prepared for i.v. administration in a biocompatible vehicle. CPT-11 (Camptosar®, Pharmacia) was obtained as the pharmaceutical drug and was prepared in 5% dextrose-water (D5W). All preparations were made fresh weekly and injection volumes were adjusted to body weight (0.2 ml/20 g mouse).

Mice/Husbandry. Female nu/nu mice were obtained from Charles River, housed in static microisolators, and provided ad libitum with water and an irradiated standard rodent diet (Purina Pico-Lab Rodent Diet 20).

Determination of maximum tolerated dose (MTD). Mice at 8 weeks of age were pair-matched into groups of 5-8 animals and preliminary toxicity studies were performed with unknown test compounds. Animals were treated i.v. daily for 10 consecutive days with test compound and were weighed twice weekly. Mice were examined frequently for clinical signs of any adverse drug-related effects. Acceptable toxicity for anti-cancer drugs in mice is defined by the NCI as no mean group weight loss of over 20% and not more than 10% toxic death in treated animals.

Standard Protocol. Athymic nude mice (male or female, 6-7 weeks) were implanted s.c. with single 1 mm3 tumor fragments (tumor brie) or alternatively, 5-10×106 tissue culture-derived cells into the flank. Animals were initially monitored twice weekly for tumor growth and then daily as the implants approached the desired size of approximately 100 mm3. When the tumors grew to between 62-221 mg in calculated tumor weight, the animals were pair-matched into appropriate experimental treatment groups (8-10 animals/ group) and treatment with test compounds was initiated. A positive control was dosed according to historical controls. Tumor weights were calculated and body weights were taken twice weekly and animals were observed frequently for adverse drug effects. The protocol called for any animal whose tumor mass reached 1000 mg to be immediately euthanized.

Tumors were measured by determining the length and width of the tumor with a digital caliper. Tumor weight was estimated using the following formula:

Tumor Weight(mg)=$(w^2 \times l)/2$ where w=width and l=length in mm of the tumor. These values can also be expressed in volumetric units (mm3).

Experimental treatment may cause partial regression (PR) or complete regression (CR) of tumors. PR is where the tumor size is 50% or less of the starting (day 1) size but greater than 0.0 mg for three consecutive days during the course of the study, whereas a CR occurs when there is no measurable tumor mass for three consecutive days. Cures are defined as animals whose tumor shrinks to 0 mg and remains that way until the completion of the experiment.

Log cell kill (LCK) is a calculation that determines the percentage of tumor cells that are killed after the initiation of treatment and can be used as a quantitative measure of efficacy:

Log Cell Kill(LCK)=$(T-C)/(3.32)(Td)$ where T=is the mean time required for the treatment group of mice to reach 1000 mg in size, C=the mean time for the control group tumors to reach 1000 mg in size, Td=is the tumor doubling time estimated from the linear regression analysis from a semi-log growth plot of the control group tumors during exponential growth and 3.32=the number of doublings required for a population to increase 1-log 10 unit. Each LCK unit represents 1-log 10 unit of cell killing (e.g. 1 LCK=90% kill, 2 LCK=99% kill, etc.). We consider compounds to be significantly active when they have LCK values >1, which corresponds to >90% tumor cell kill.

Tumor growth inhibition (TGI) is a calculation that describes the amount of tumor growth that is inhibited by treatment with a compound over a defined period of time. It is expressed as:

% TGI=100(1−$T/C$)

where T is the mean tumor size of a compound treated group on a given day, and C is the mean tumor size of the vehicle control group on the same day.

Toxic deaths are defined as deaths caused by compound treatment and not by advanced disease state. A death is considered toxic if the animal dies within 1 week after the final compound treatment and the tumor size has not reached 1000 mg. Non-tumor related deaths after this point are recorded, but not considered toxic deaths.

Tumor regression is defined according the following conventions: a regression is defined as partial (PR) if the tumor weight decreases to <50% of the starting weight (<50 mg). A regression is defined as complete (CR) if the tumor weight decreases below measurable weight during the experimental period. A cure is defined as a tumor-free animal at end of the observation period.

Results. FIG. 6 shows the results of an A2780 xenograft tumor model achieved from compound A37. FIG. 7 shows the results of a PC3 xenograft tumor model achieved from compound A37. FIG. 8 shows the results of a A2780 xenograft tumor model achieved from compound B16.

Assay 8: Measurement of Affinities Between Target Molecules and Compounds

In order to confirm the suitability of a given chemical compound for the uses proposed herein, it may be helpful to characterize the binding properties of such compound to its known binding partners, if any. This, however, should not be interpreted as limiting the scope of the invention.

The affinity of chemical compounds to their corresponding binding partners may be determined, for example, using a BIACORE™ assay system (Biacore AB, Uppsala, SE). Other systems yielding a qualitatively similar result, such as, for example, those developed by Affinity Sensors (Cambridge, UK), will be readily apparent to those skilled in the art.

In a representative procedure, the binding of Compound R to its known binding partners CDK2/cyclinE was analyzed. The analysis was performed on a BIACORE 2000 SPR-Biosensor at 22° C. in a running buffer containing 20 mM HEPES (pH 7.4), 150 mM NaCl, 1 mM DTT and 0.005% Tween 20 (protein grade, Calbiochem). A 10 µM solution of Compound R was coupled at pH 8.0 to the dextrane-surface of a CM5 sensor-chip (research grade) via amide coupling chemistry. In order to characterize the binding of Compound R to proteins, for example CDK2/cyclinE, a purified protein fraction was diluted in running buffer to obtain nine distinct protein concentrations, which were then allowed to pass over the sensor surface consecutively for 5 min each, followed by 5 min of running buffer at the same flow rate. The association and dissociation of the CDK2/cyclinE complex onto the CM5-Compound R-loaded chip surface was measured at a flow rate of 30 µl/min. After each experiment, the chip was regenerated by two consecutive injections of 3 M guanidinium-hydrochloride (20 sec, 30 µl/min) before the next sample was loaded.

The data were analyzed using the Bioevaluation software version 3.1 (Biacore AB, Uppsala, SE). The curves were normalized to the injection start, and the background obtained with a control surface. The association and dissociation rates were determined separately or globally using a Langmuir 1:1 binding model. The affinities ($K_D$) were calculated using the equation:

$K_D$=kdiss/kass

The above procedure can be performed analogously with other target proteins, for example Cdk9, Cdk4 etc. An inhibitor of Cdk9, for example, may be useful in the treatment or prophylaxis of HIV and/or AIDS.

FIG. 9 shows as an example the results obtained for the binding of CDK2/cyclinE to the CM5-Compound R-loaded chip. The $K_D$ calculated from these data amounts to 8.0+/−2.8 nM.

Assay 9: Antiviral Activity

The activity of the certain compounds of the invention was evaluated in peripheral blood mononuclear cells (PBMCs) infected with the low passage, clinical isolate HIV-1ROJO to generate a measure of the efficacy of these compounds in acutely infected cells. The use of these normal human cells allows an estimate of the therapeutic index of these compounds to be made. Fresh PBMCs from two donors were pooled and stimulated with PHA-P for 48-72 hours. The cells were then cultured in the presence of IL-2 to maintain the cell division initiated by the mitogenic signal. The virus was added at a multiplicity of infection of 0.1. The cells were cultured for 7 days post infection prior to the evaluation of efficacy. Viral replication was measured by the level of reverse transcriptase activity in the supernatant and cytotoxicity was measured with the MTS assay. The results of duplicate determinations of the anti-HIV efficacy and cytotoxicity of these compounds are presented in Table 7.

All references, patents, and publications cited herein are hereby incorporated by reference in their entirety.

TABLE 1

Range of compound concentrations used in Assay 1.

| Concentration of Compound | 0 | 5 nM | 10 nM | 25 nM | 50 nM | 100 nM | 250 nM |
|---|---|---|---|---|---|---|---|

TABLE 2

Results for certain compounds of the invention for the BrdU incorporation assay described above.

| Compound | Brd U [uM] | | |
|---|---|---|---|
| | 24 h | 48 h | 72 h |
| A | | | <0.1 |
| B | | | |
| C | <0.1 | <0.1 | <1 |
| D | <0.1 | <0.1 | <0.1 |
| E | <0.01 | <0.1 | <0.1 |
| F | | <0.1 | <1 |
| G | <0.01 | <0.1 | <0.1 |
| H | <1 | <1 | <1 |
| I | <0.01 | <0.1 | <0.1 |
| J | | | |
| K | <0.1 | <0.1 | <0.1 |
| L | <0.1 | <0.1 | <0.1 |
| M | <0.1 | <0.1 | <0.1 |
| N | | | |
| O | <0.1 | <1 | <1 |
| P | | | |
| Q | <0.1 | <0.1 | <0.1 |

TABLE 3

Results for certain compounds of the invention for the following in-vitro celluar activity assays described above: viability and clonogenic survival assays with HCT-116 cells viability assays with IMR90 cells, and two measures of activity against the NCI cell panel ("Mean-Graph MID-point and IC50 against an adriamycin resistant cell line)

| | HCT-116 IC50 (µM) | | | | | | NCI panel | |
|---|---|---|---|---|---|---|---|---|
| | | | Clonogenic | | | | | |
| Compound | Viability | Protein adjusted | 24 h | 48 h | 72 h | IMR90 (µM) | MG-MID (µM) | ADR-res (µM) |
| A | <0.1 | <1 | <1 | <0.1 | <0.1 | <0.1 | <0.1 | <1 |
| B | <1 | | | | | <1 | | |
| C | <0.1 | <1 | <1 | | | <0.1 | <0.1 | <0.1 |
| D | <0.01 | | <0.1 | | | <0.01 | | |
| E | <0.1 | <1 | <0.1 | | <0.1 | <0.1 | <0.1 | <1 |
| F | <0.1 | <0.1 | <1 | | <0.1 | <0.1 | <0.1 | <1 |
| G | <0.1 | <1 | <0.1 | <0.1 | | <0.1 | <0.1 | <1 |
| H | <0.1 | <1 | <1 | <0.1 | | <0.1 | <0.1 | >10 |
| I | <0.1 | <1 | <0.1 | <0.1 | | <0.1 | <0.1 | <1 |
| J | <1 | | | | | <0.1 | | |
| K | <0.1 | <1 | <1 | | | >0.1 | <0.1 | <10 |
| L | <0.1 | <1 | | <0.1 | | >0.1 | >10 | >10 |
| M | <0.1 | <1 | <0.1 | | | <0.1 | | |
| N | <1 | <1 | | | | >0.1 | | |
| O | <0.1 | <1 | <0.01 | | | <0.1 | | |
| P | <0.01 | | <0.1 | | | <0.1 | | |
| Q | <0.1 | <1 | <0.1 | | <0.1 | <0.1 | <0.1 | <10 |

TABLE 4

Results for certain compounds of the invention (IC50 as nM) for the arrested cell assay described above.

| | Arrested cell assay (nM) | |
|---|---|---|
| Compound | IMR90 | HCT |
| A | | |
| B | | |
| C | >1.0 | <0.01 |
| D | >1.0 | <0.01 |
| E | >0.1 | <0.1 |
| F | >1.0 | <0.1 |
| G | >0.1 | <0.1 |
| H | >1.0 | <0.1 |
| I | >1.0 | <0.1 |
| J | | |
| K | >1.0 | <0.01 |
| L | | |
| M | >1.0 | <0.1 |
| N | | |
| O | >0.1 | <0.1 |
| P | | |
| Q | >0.1 | <0.1 |

TABLE 5

Results for certain compounds of the invention (IC50 as μM) for biochemical inhibition assays described above.

| Compound | Cdk2/ Cyclin E | Cdk2/ Cyclin A | Cdk4/ Cyclin D | Cdc2/ Cyclin B | Cdk6/ Cyclin D2 | PKA | PKC | c-Abl |
|---|---|---|---|---|---|---|---|---|
| A | <0.1 | <0.1 | <1 | <1 | <1 | | | |
| B | <0.01 | <0.1 | <10 | <0.1 | | | | |
| C | <0.1 | <0.1 | <1 | <1 | | >10 | >10 | >10 |
| D | <0.1 | <0.1 | <1 | <1 | | | | |
| E | <0.01 | <0.01 | <0.01 | <0.1 | <0.01 | <10 | <10 | <10 |
| F | <0.1 | <0.1 | <0.01 | <0.1 | <0.01 | | | |
| G | <0.1 | <0.1 | <0.01 | <0.1 | | >10 | | >10 |
| H | <0.1 | <0.1 | <0.1 | <0.1 | | | | |
| I | <0.1 | <0.1 | <0.01 | <0.1 | | | | |
| J | <0.1 | | | | | | | |
| K | <0.1 | | | | | | | |
| L | <0.1 | | <0.1 | <0.1 | | | | |
| M | <0.1 | | | | | | | |
| N | <0.1 | | | <0.01 | | | | |
| O | <0.1 | | | | | | | |
| P | <0.1 | | | | | | | |
| Q | <0.01 | <0.1 | <0.01 | <0.1 | <0.1 | | | |

TABLE 6

Results for additional compounds in the biochemical inhibition and HCT-116 viability assays (non-protein adjusted) described above.

| Compound | Cdk2/ cyclin E | Cdk4/ cyclin D1 | Cdc2/ cyclin B | HCT-116 viability |
|---|---|---|---|---|
| A1 | <0.01 | <1 | <0.1 | <0.1 |
| A2 | <0.01 | <10 | <1 | <0.1 |
| A3 | <0.1 | <0.1 | <0.1 | <0.1 |
| A4 | <0.01 | <0.1 | <0.1 | <0.1 |
| A5 | <0.1 | <10 | <1 | <0.1 |
| A6 | <0.01 | <0.1 | <0.01 | <0.1 |
| A7 | <0.1 | <0.1 | <0.1 | <0.1 |
| A8 | <0.1 | <0.1 | <0.1 | <0.1 |
| A9 | <0.1 | <0.1 | <0.01 | <0.1 |
| A10 | <0.1 | <1 | <0.01 | <0.1 |
| A11 | <0.1 | <0.1 | <0.1 | <0.1 |
| A12 | <0.1 | <0.1 | <0.1 | <0.1 |
| A13 | <0.1 | <0.1 | <0.1 | <0.01 |
| A14 | <0.1 | <0.1 | <0.1 | <0.1 |
| A15 | <0.1 | <0.1 | <0.01 | <0.1 |
| A16 | <0.1 | <1 | <0.1 | <0.1 |
| A17 | <0.1 | <0.1 | <0.01 | <0.1 |
| A18 | <0.1 | <0.1 | <0.1 | <0.1 |
| A19 | <0.1 | <1 | <0.1 | <0.1 |
| A20 | <0.01 | <0.1 | <0.01 | <0.1 |
| A21 | <0.01 | <1 | <0.1 | <0.1 |
| A22 | <0.01 | <0.1 | <0.1 | <0.1 |
| A23 | <0.01 | <0.1 | <0.1 | <0.1 |
| A24 | <0.01 | <0.1 | <0.01 | <0.01 |
| A25 | <0.1 | <0.1 | <0.1 | <0.01 |
| A26 | <0.1 | <0.1 | <0.1 | <0.01 |
| A27 | <0.1 | <0.1 | <0.01 | <0.1 |
| A28 | <0.1 | <1 | <0.1 | <0.1 |
| A29 | <0.01 | <0.1 | <0.1 | <0.1 |
| A30 | <0.1 | <1 | <1 | <0.1 |
| A31 | <0.1 | <0.1 | <0.1 | <0.1 |
| A32 | <0.1 | <0.1 | <1 | <0.1 |
| A33 | <0.1 | <0.1 | <0.1 | <0.1 |
| A34 | <0.01 | <0.1 | <0.1 | <0.1 |
| A35 | <0.1 | <0.1 | <0.01 | <0.1 |
| A36 | <0.1 | <0.1 | <0.1 | <0.01 |
| A37 | <0.1 | <0.1 | <0.1 | <0.1 |
| A38 | <0.1 | <1 | <0.1 | <0.1 |
| A39 | <0.1 | <1 | <1 | <0.1 |
| A40 | <0.1 | <0.1 | <0.1 | <0.1 |
| A41 | <0.1 | <0.1 | <1 | <0.1 |
| A42 | <0.1 | <1 | <1 | <0.1 |
| A43 | <0.1 | <1 | <1 | <0.1 |
| A44 | <0.1 | <0.1 | <0.01 | <0.1 |
| A45 | <0.1 | <0.1 | <0.01 | <0.01 |
| A46 | <0.1 | <1 | <0.01 | <0.1 |
| A47 | <0.1 | | <0.1 | <0.01 |
| A48 | <0.1 | | <1 | <0.1 |
| A49 | <0.1 | | <0.1 | <0.1 |
| A50 | <0.1 | | <1 | <0.1 |
| A51 | <0.1 | | | <0.1 |
| A52 | <0.1 | <1 | <1 | <0.1 |
| A53 | <1 | <10 | <1 | <0.01 |
| A54 | <0.01 | <1 | <0.01 | <0.1 |
| A55 | <0.1 | <10 | <0.1 | <0.1 |
| A56 | <0.1 | <1 | <0.1 | <0.1 |
| A57 | <0.01 | <0.1 | <0.01 | <0.1 |
| A58 | <0.01 | <10 | <10 | <0.1 |
| A59 | <0.1 | <1 | <0.1 | <0.1 |
| A60 | <0.1 | <10 | <1 | <0.1 |
| A61 | <0.1 | <1 | <0.1 | <0.1 |
| A62 | <0.1 | <10 | <0.1 | <0.1 |
| A63 | <0.1 | <1 | <0.1 | <0.1 |
| A64 | <0.1 | <1 | <0.1 | <0.1 |
| A65 | <0.1 | <0.1 | <0.01 | <0.1 |
| A66 | <0.1 | <10 | <0.1 | <0.1 |
| A67 | <0.01 | | <0.1 | <0.1 |
| A68 | <0.01 | <0.1 | <0.1 | <1 |
| A74 | <0.1 | | <0.1 | >0.25 |
| A76 | <0.1 | <0.1 | <0.1 | <0.1 |
| A77 | | | | <0.1 |
| A78 | | | | <0.01 |
| A79 | | | | <0.1 |
| A80 | | | | <0.1 |
| A81 | | | | <0.1 |
| A82 | <0.1 | | | <0.1 |
| B1 | <0.01 | | | <1 |
| B2 | <0.1 | | <0.01 | <0.1 |
| B3 | <0.1 | | <0.01 | <0.1 |
| B4 | <0.1 | | | <0.1 |

TABLE 6-continued

Results for additional compounds in the biochemical inhibition and HCT-116 viability assays (non-protein adjusted) described above.

| | IC50 (μM) | | | |
|---|---|---|---|---|
| Compound | Cdk2/ cyclin E | Cdk4/ cyclin D1 | Cdc2/ cyclin B | HCT-116 viability |
| B5 | <0.1 | | | <0.1 |
| B6 | <0.1 | | | <0.1 |
| B7 | <0.1 | | | <1 |
| B8 | | | <0.1 | <0.1 |
| B9 | | | <0.1 | <0.1 |
| B10 | | | <0.1 | <0.1 |
| B11 | | | <0.1 | <1 |
| B12 | | | <0.1 | <0.1 |
| B13 | | | <0.1 | <0.01 |
| B14 | | | | <0.01 |
| B15 | | | | <0.01 |
| B16 | <0.01 | | <0.01 | <0.01 |
| B17 | | | | <0.01 |
| C1 | | | | <0.1 |
| C3 | <0.1 | | | <0.1 |
| C4 | <0.01 | | | <0.1 |
| C5 | | | | <0.25 |

TABLE 7

Results for antiviral activity for certain compounds of the invention. IC50: 50% inhibition of virus replication measured by reverse transcriptase levels in the supernatant; TC50: 50% cytoxicity (MTS); TI: TC50/IC50.

| Compound | IC50 (μM) | TC50 (μM) | TI |
|---|---|---|---|
| A32 | <0.01 | <0.1 | >10 |
| A61 | <0.01 | <0.1 | >10 |
| A64 | <0.01 | <0.1 | >10 |
| C3 | <0.01 | <0.1 | >10 |
| C4 | <0.1 | <0.1 | >1 |
| AZT | <0.01 | >1.0 | >100 |

TABLE A

| Compound | Structure |
|---|---|
| A | 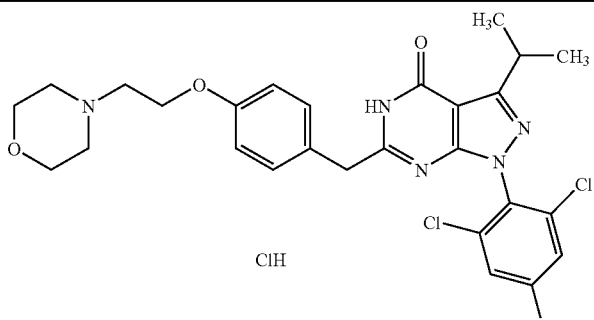 |
| B | 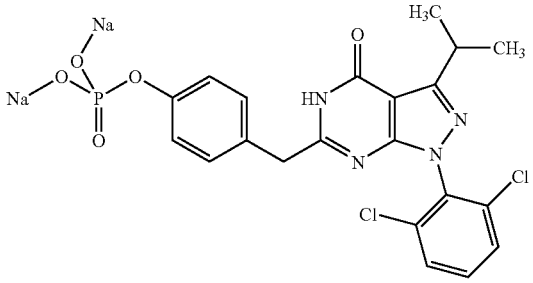 |
| C | 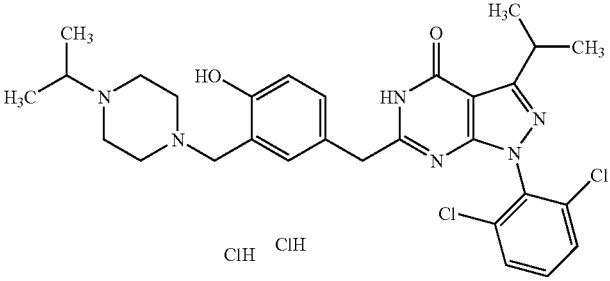 |

TABLE A-continued
| Compound | Structure |
|---|---|
| D | 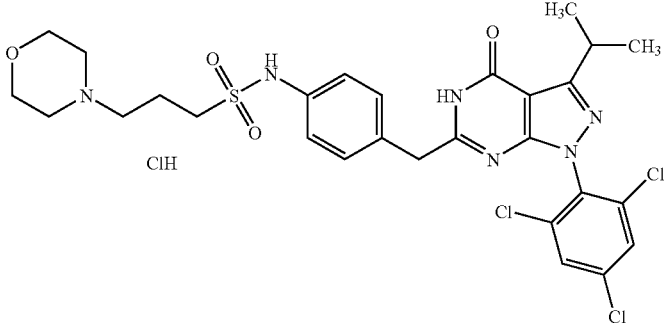 |
| A1 | 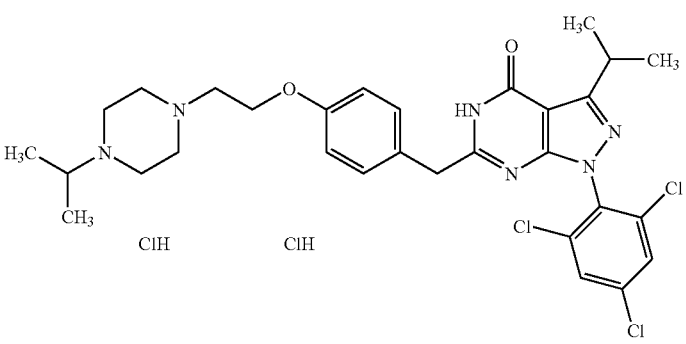 |
| A2 | 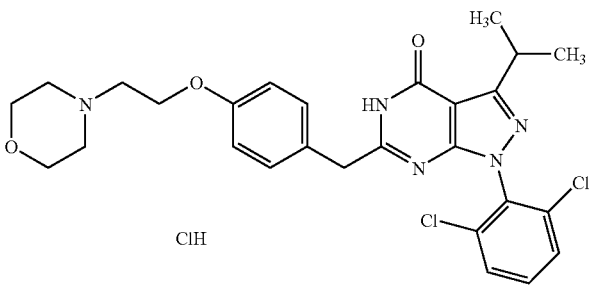 |
| A4 | 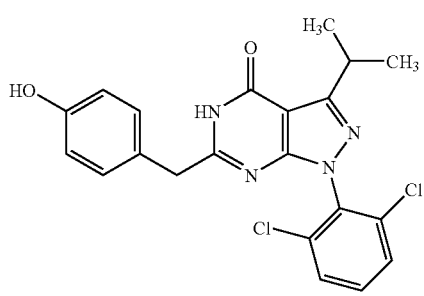 |
| A5 | 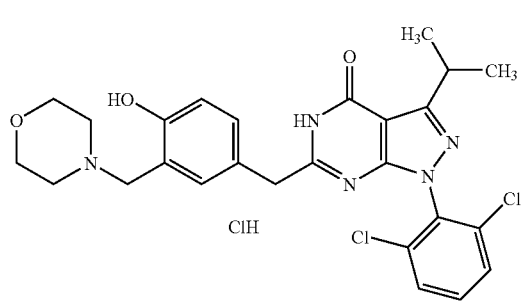 |

TABLE A-continued
| Compound | Structure |
|---|---|
| A30 | 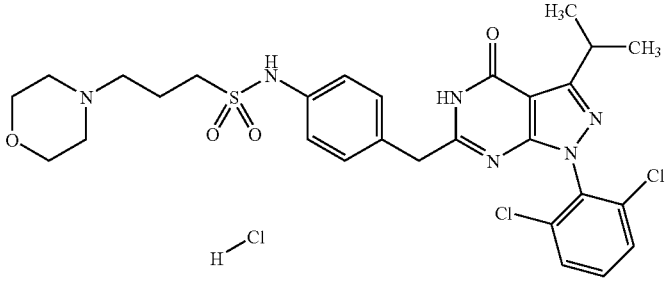 |
| A32 | 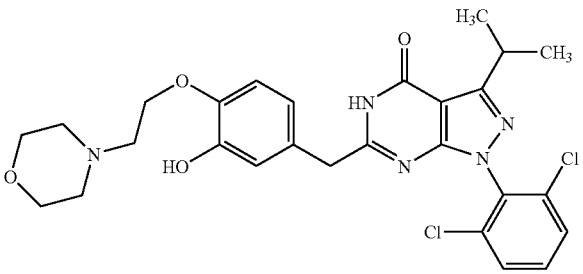 |
| A38 | 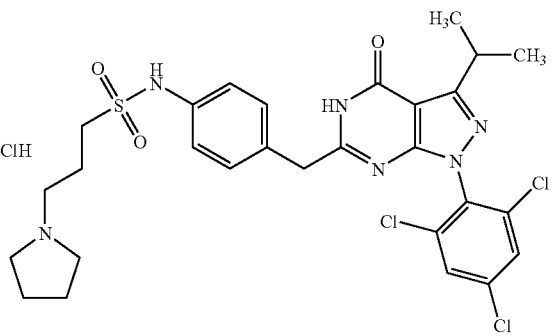 |
| A39 | 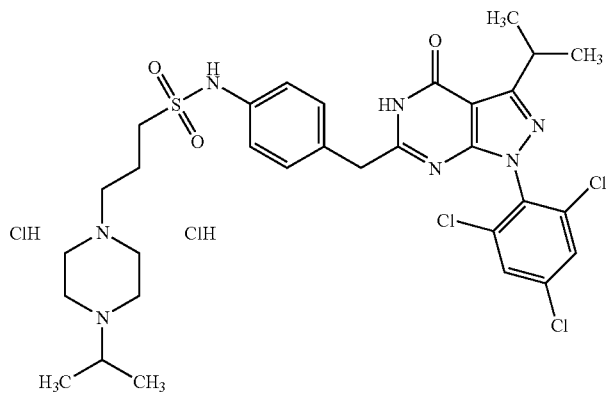 |

TABLE A-continued

| Compound | Structure |
|---|---|
| A42 | 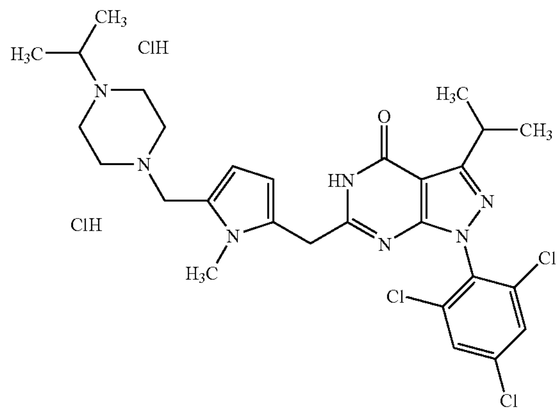 |
| A43 | 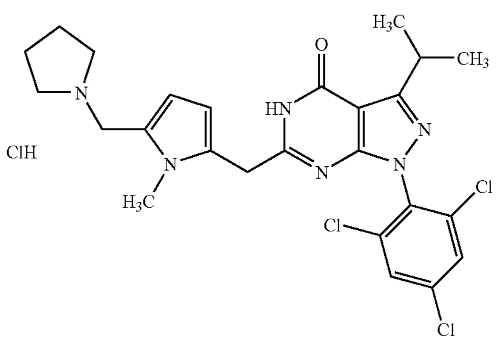 |
| A48 | 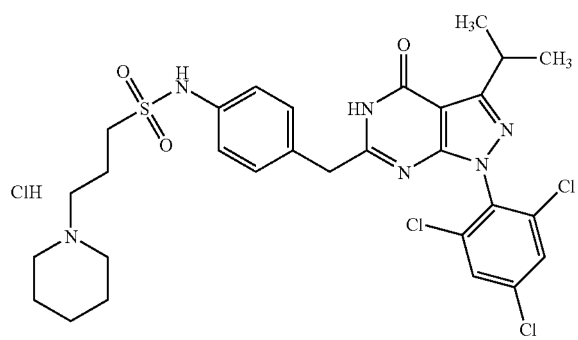 |
| A50 | 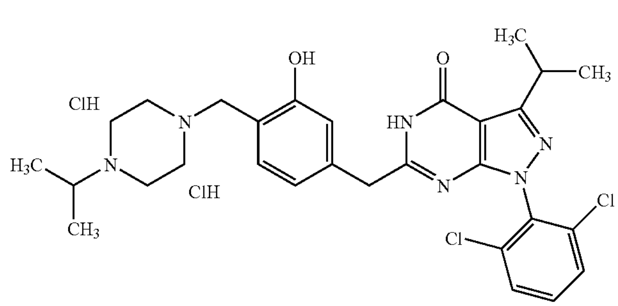 |

TABLE A-continued
| Compound | Structure |
|---|---|
| A52 | 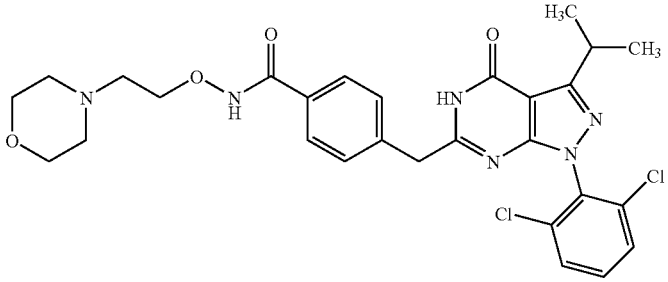 |
| A53 | 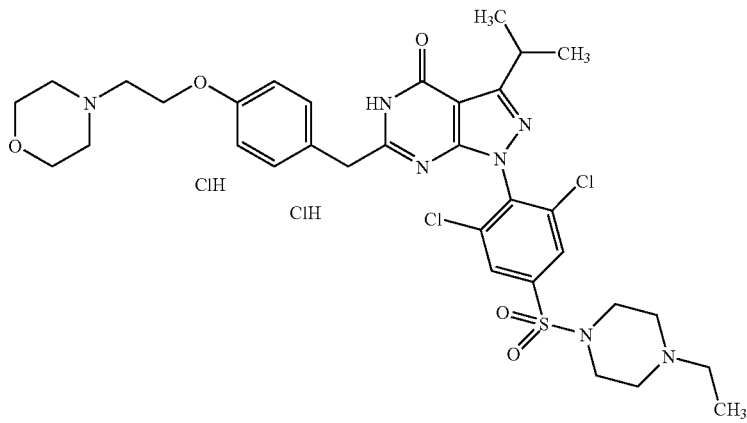 |
| A54 | 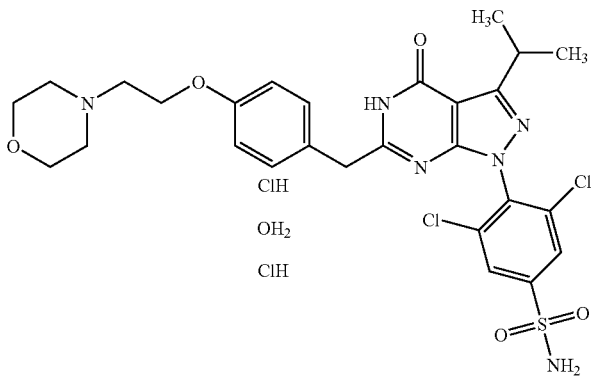 |
| A55 | 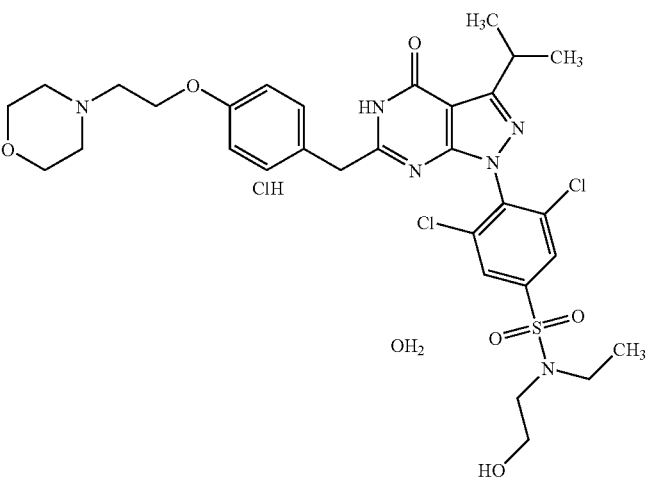 |

TABLE A-continued

| Compound | Structure |
|---|---|
| A58 | 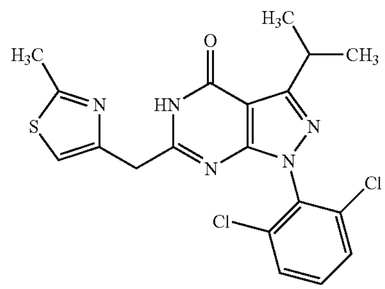 |
| A59 | 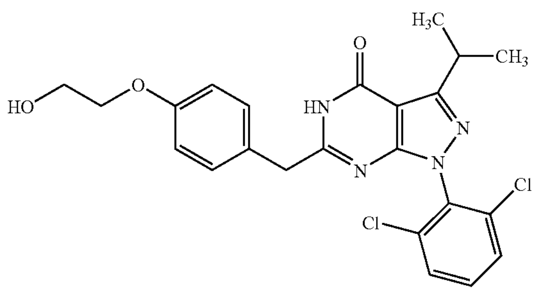 |
| A60 | 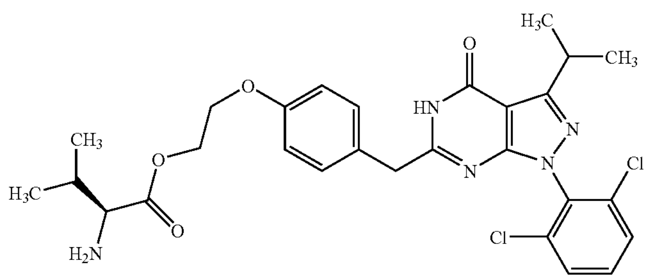 |
| A61 | 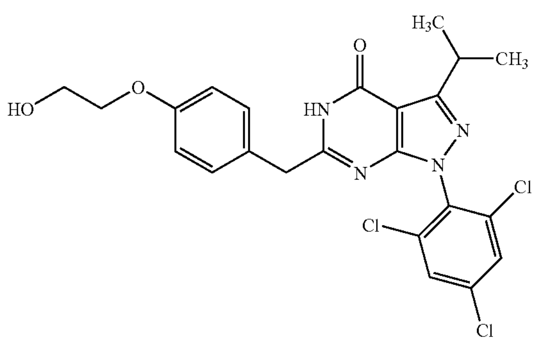 |
| A62 | 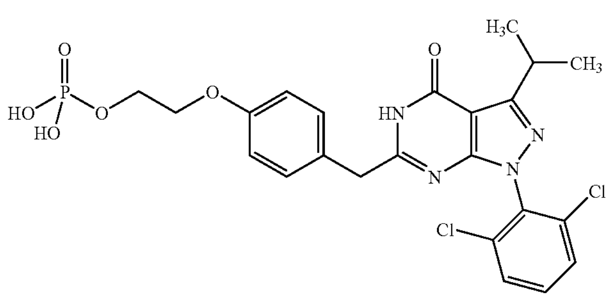 |

TABLE A-continued

| Compound | Structure |
|---|---|
| A63 | 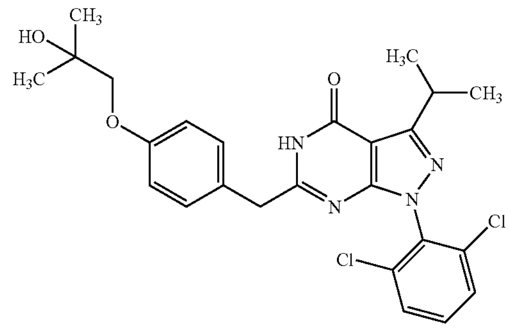 |
| A64 | 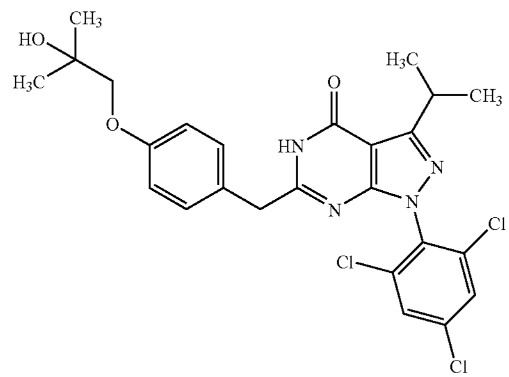 |
| A66 | 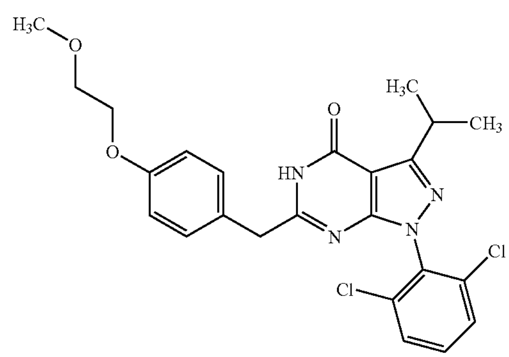 |
| A67 | 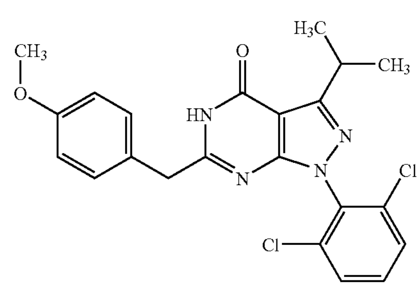 |

TABLE A-continued
| Compound | Structure |
|---|---|
| C3 | 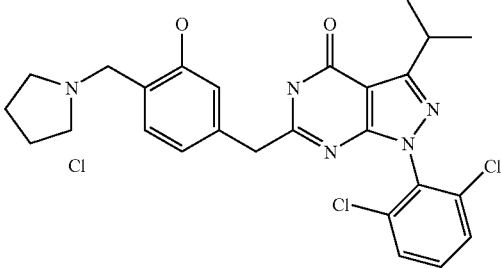 |
| C4 | 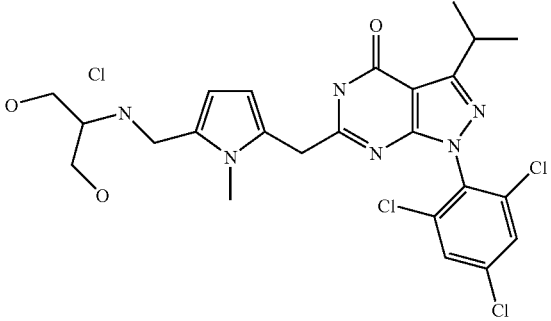 |
TABLE B
| Compound | Structure |
|---|---|
| E | 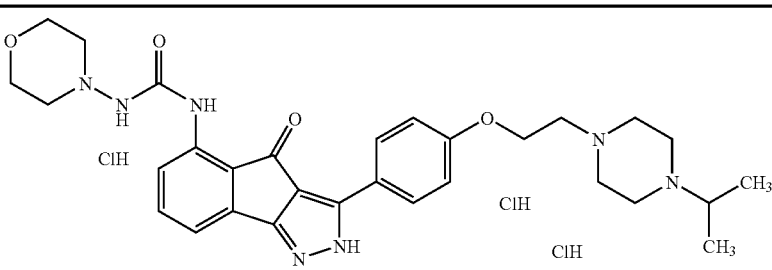 |
| F | 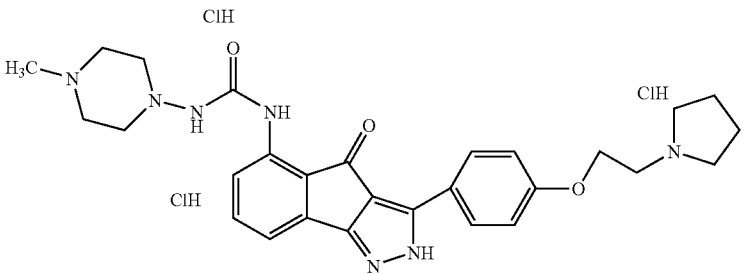 |
| G | 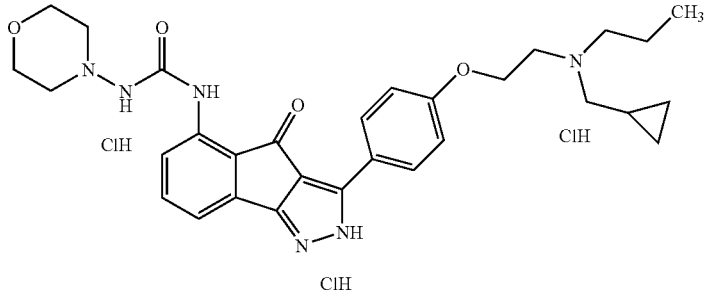 |

TABLE B-continued
| Compound | Structure |
|---|---|
| H | 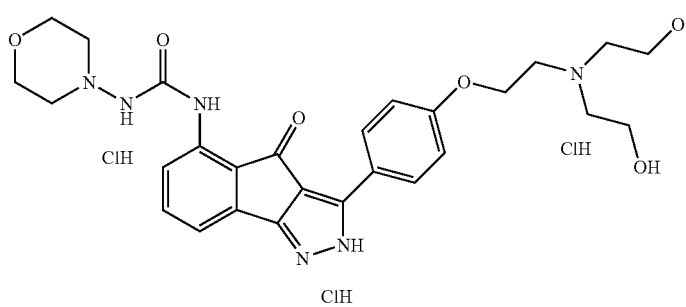 |
| I | 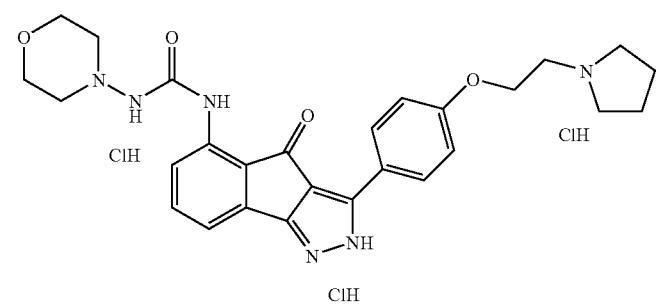 |
| J | 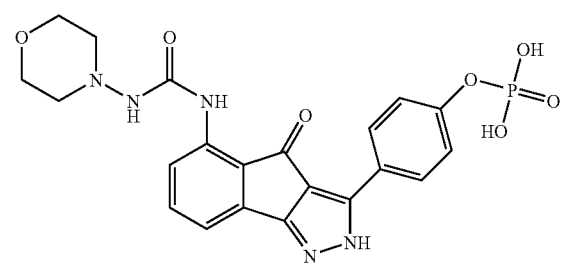 |
| K | 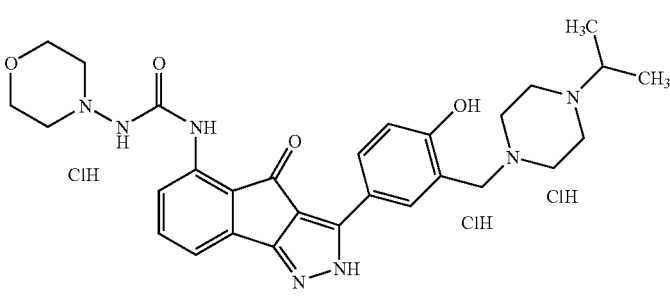 |
| L | 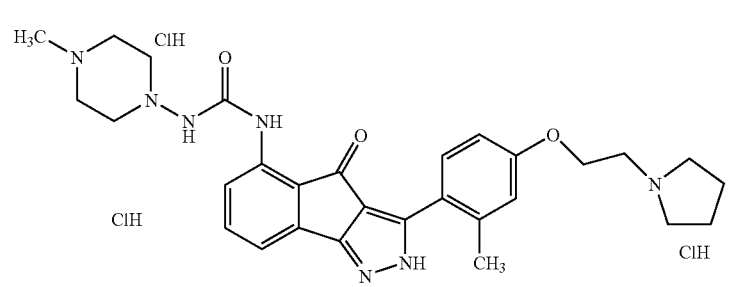 |

TABLE B-continued
| Compound | Structure |
|---|---|
| N | 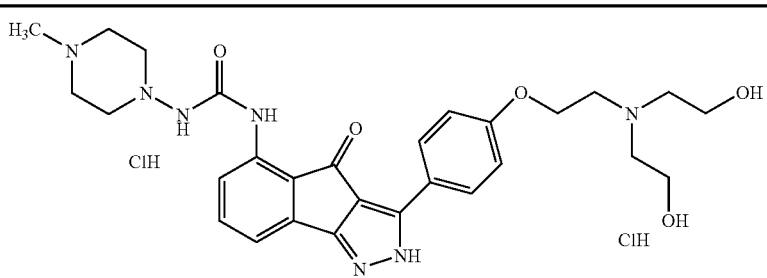 |
| M | 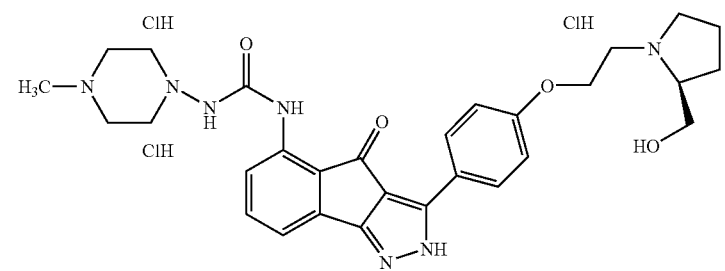 |
| O | 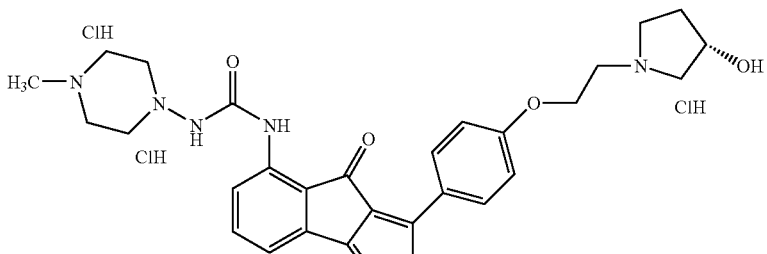 |
| P | 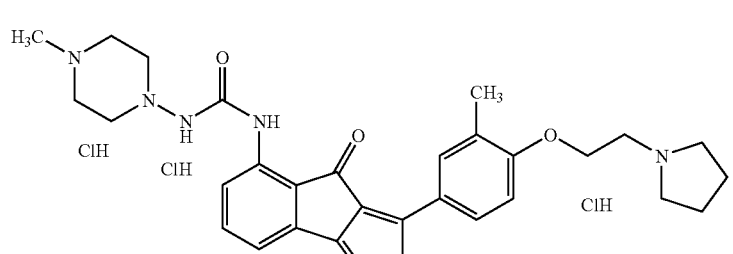 |
| Q | 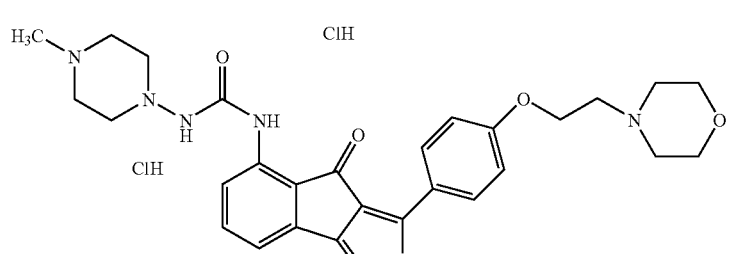 |

TABLE B-continued
| Compound | Structure |
|---|---|
| A3 | 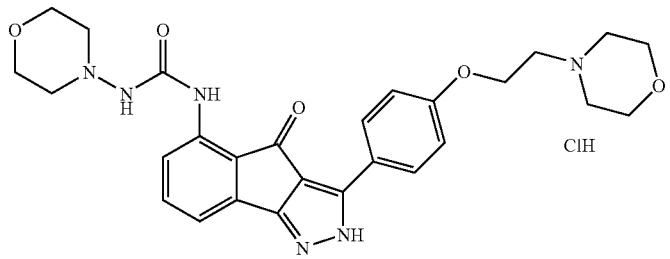 |
| A7 | 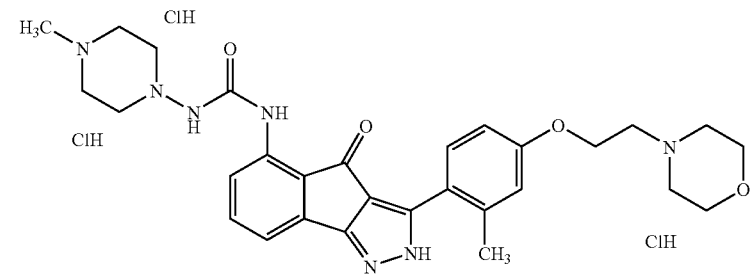 |
| A8 | 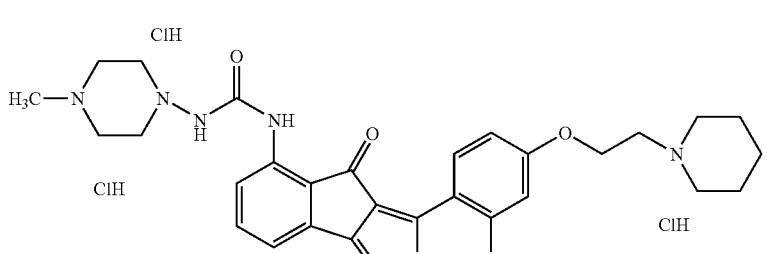 |
| A9 | 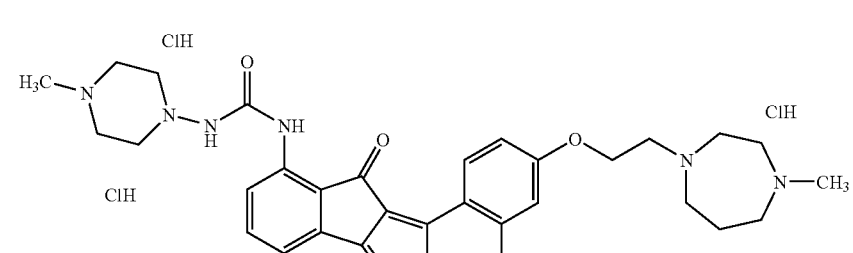 |
| A10 | 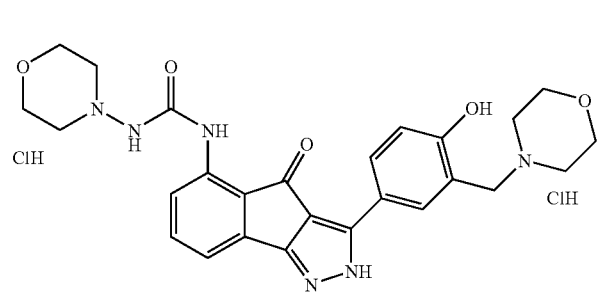 |

TABLE B-continued
| Compound | Structure |
|---|---|
| A11 | 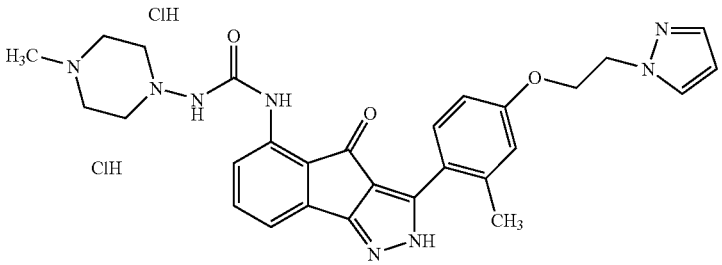 |
| A12 | 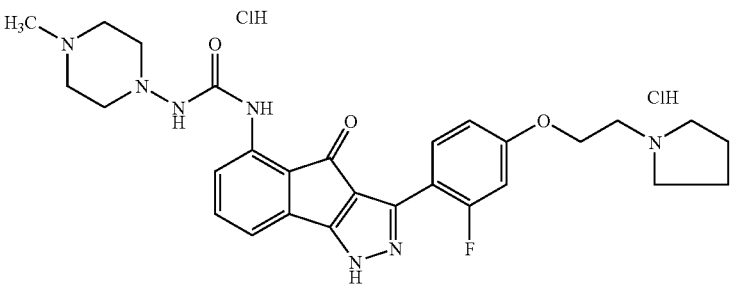 |
| A13 | 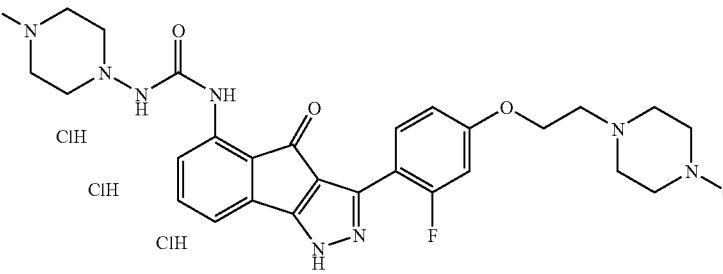 |
| A14 | 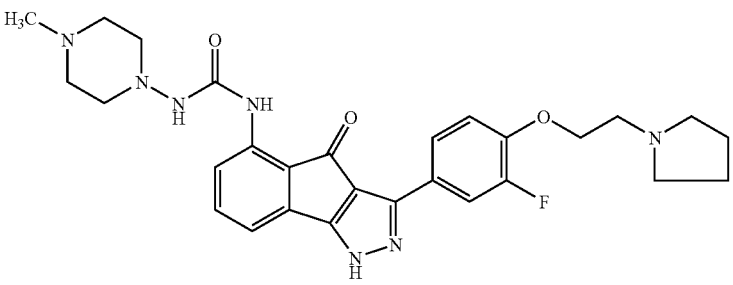 |
| A15 | 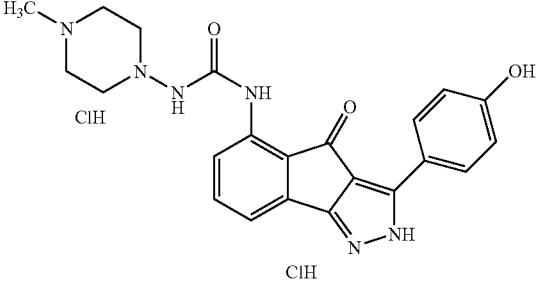 |

TABLE B-continued
| Compound | Structure |
|---|---|
| A16 | 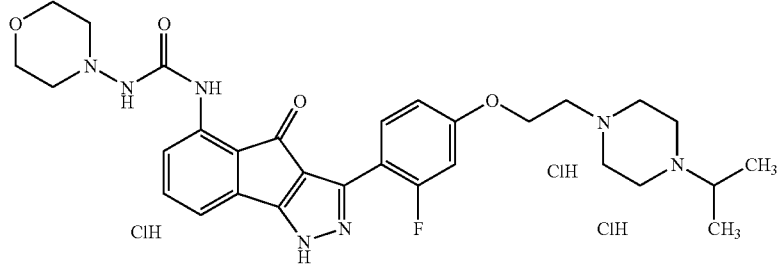 |
| A17 | 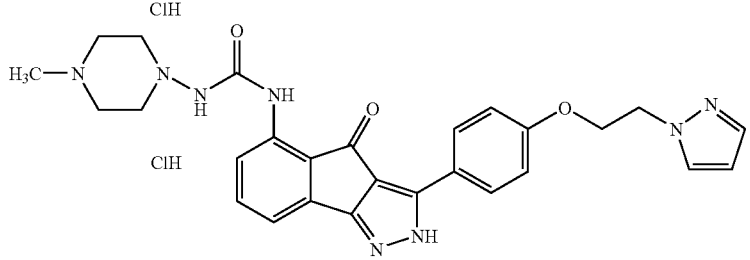 |
| A18 | 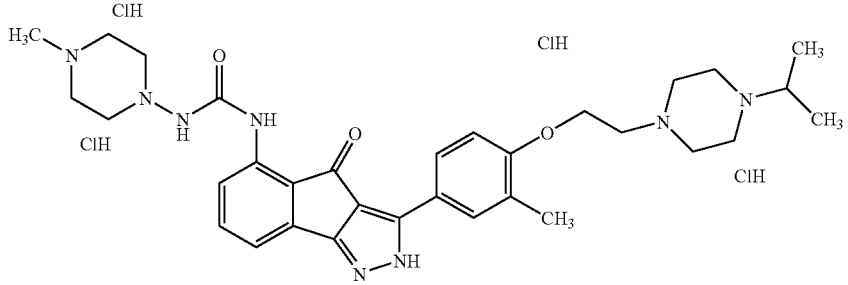 |
| A19 | 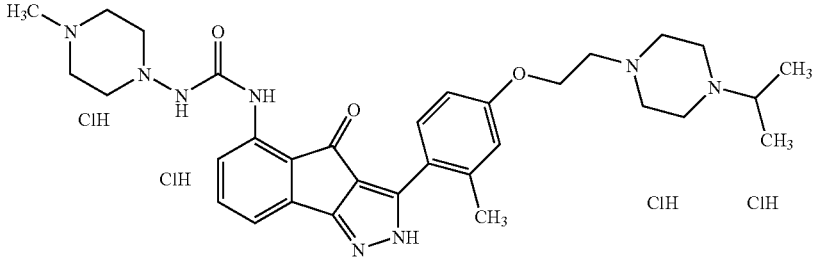 |
| A20 | 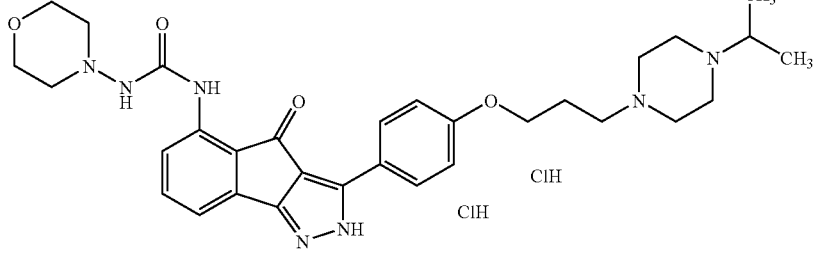 |

TABLE B-continued
| Compound | Structure |
|---|---|
| A21 | 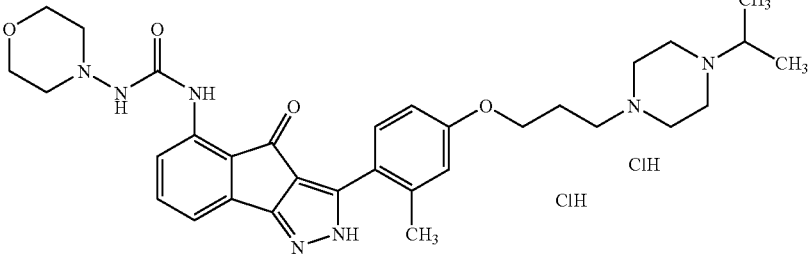 |
| A22 | 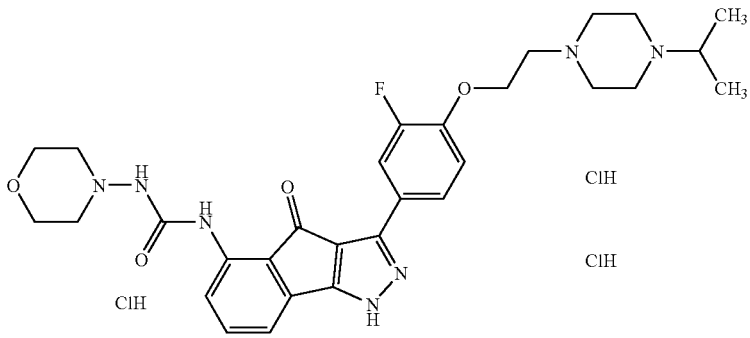 |
| A23 | 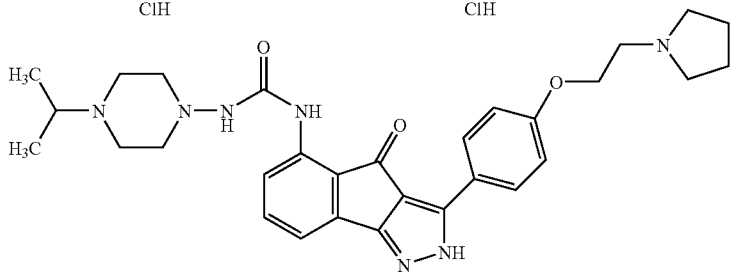 |
| A24 | 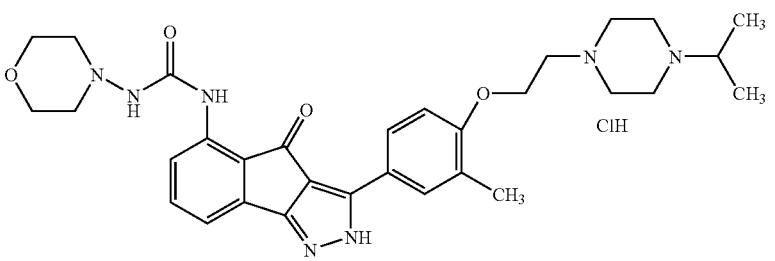 |
| A25 | 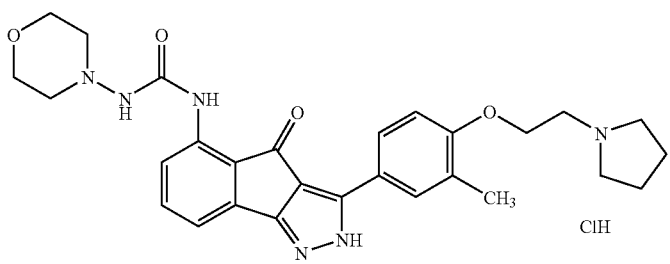 |

TABLE B-continued
| Compound | Structure |
|---|---|
| A26 | 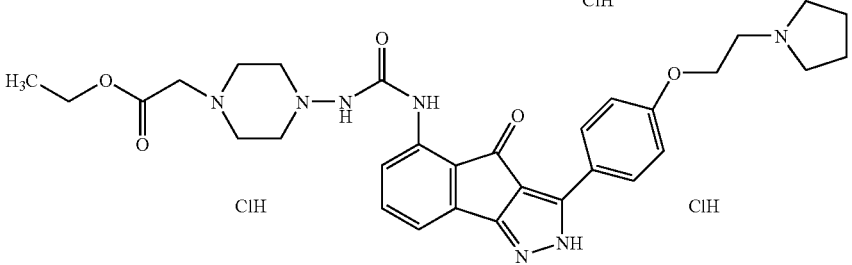 |
| A27 | 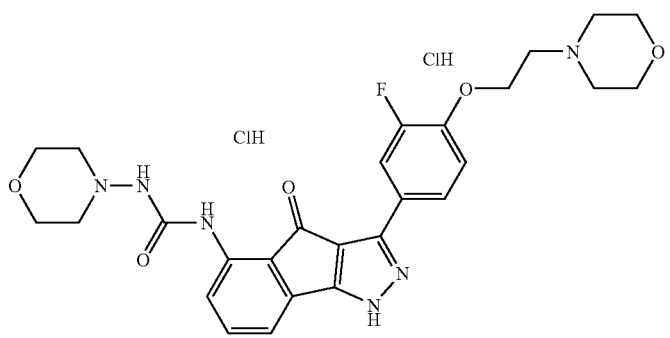 |
| A28 | 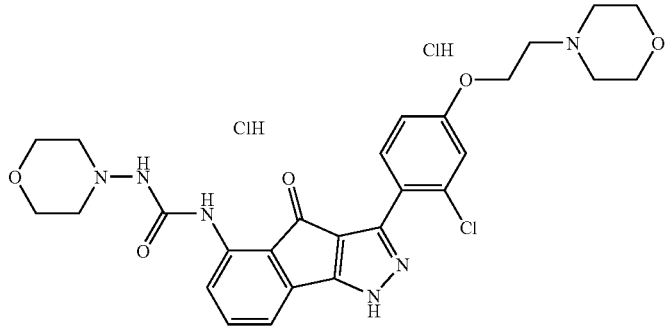 |
| A29 | 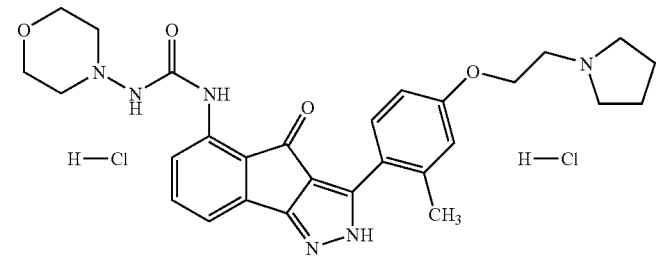 |
| A31 | 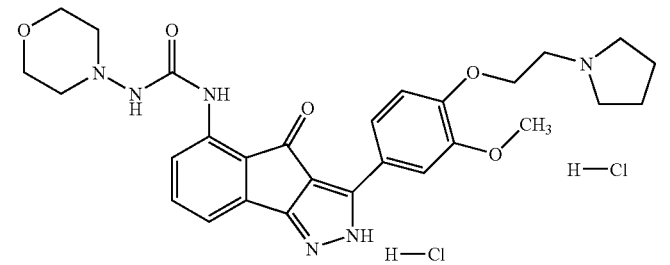 |

TABLE B-continued

| Compound | Structure |
|---|---|
| A33 | 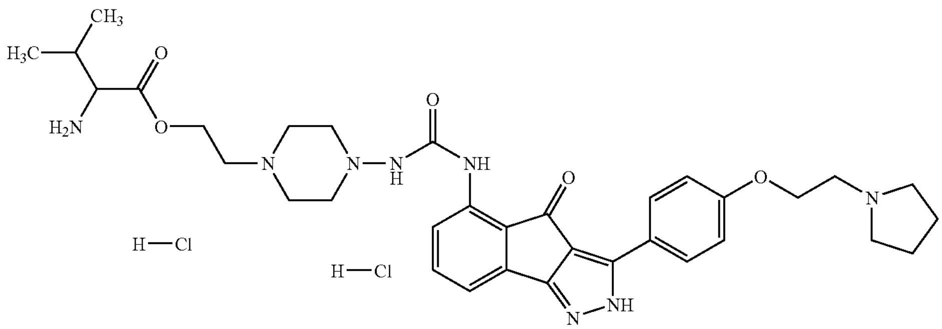 |
| A34 | 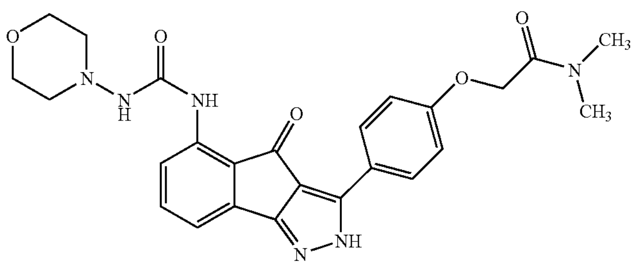 |
| A35 | 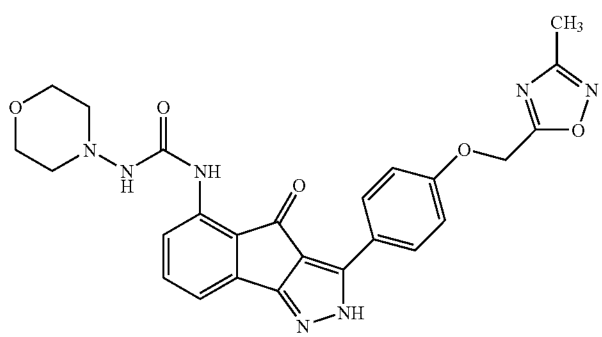 |
| A36 | 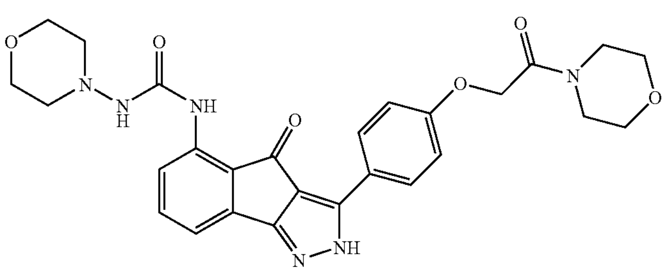 |
| A37 | 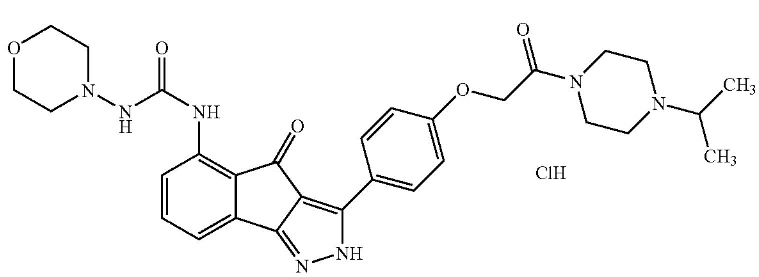 |

TABLE B-continued
| Compound | Structure |
|---|---|
| A40 | 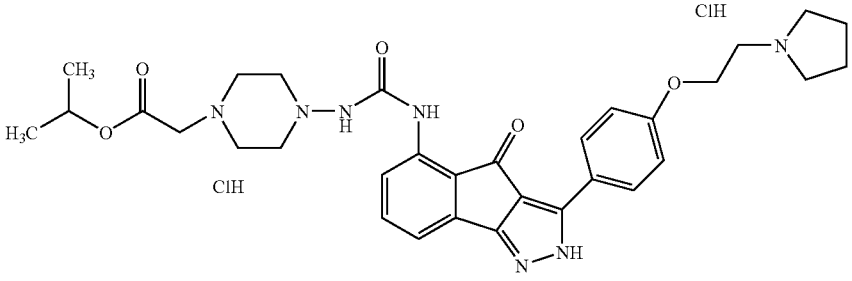 |
| A41 | 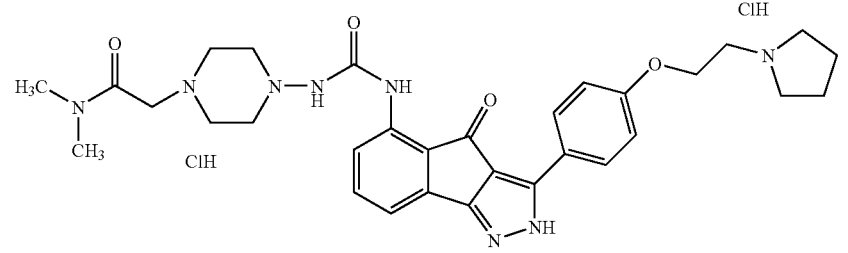 |
| A44 | 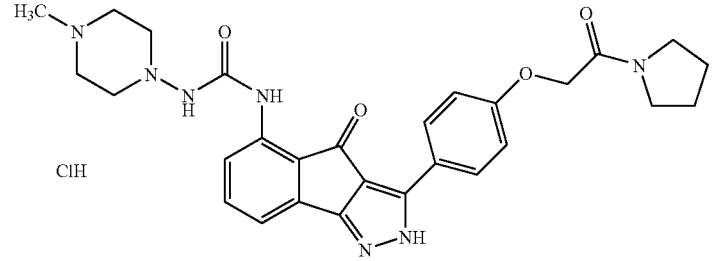 |
| A45 | 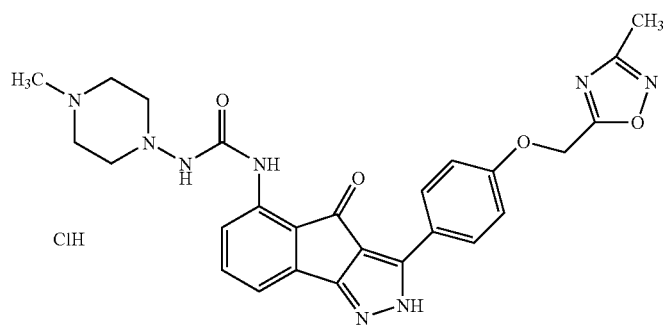 |
| A46 | 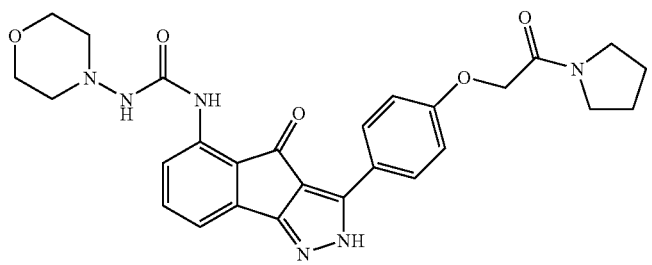 |

TABLE B-continued
| Compound | Structure |
|---|---|
| A47 | 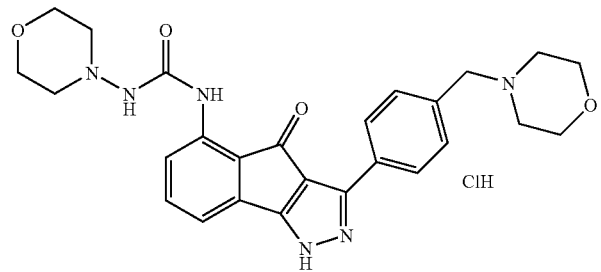 |
| A49 | 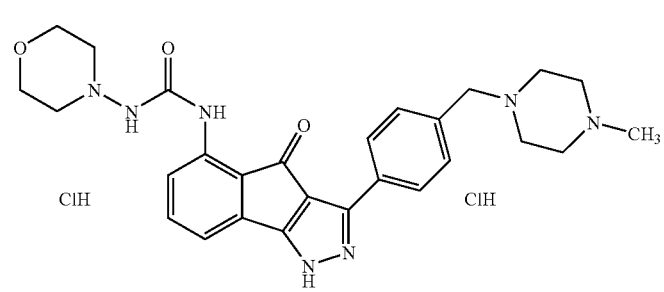 |
| A51 | 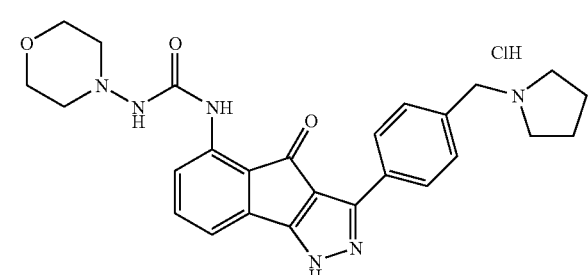 |
| A56 | 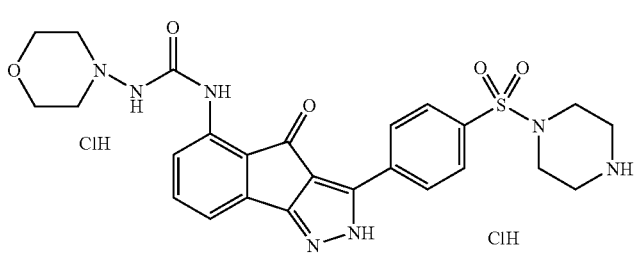 |
| A57 | 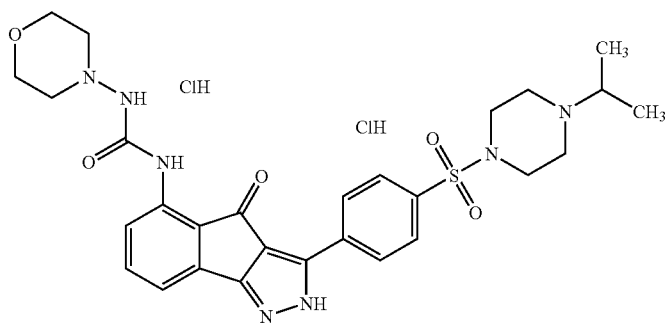 |

TABLE B-continued
| Compound | Structure |
|---|---|
| A65 | 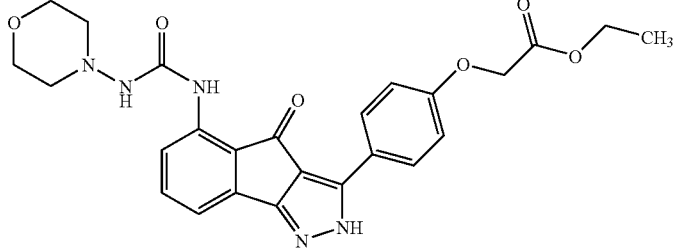 |
| A68 | 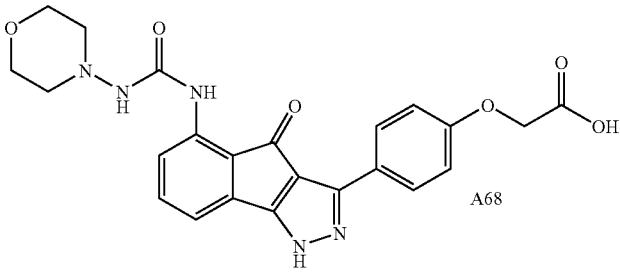 |
| A69 | 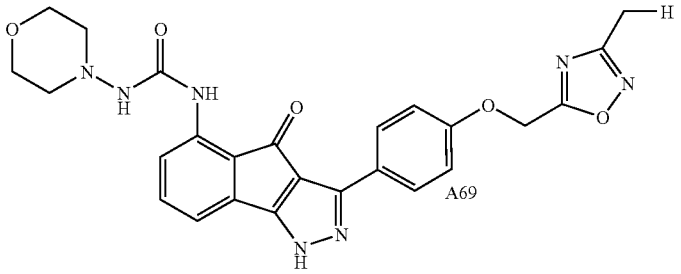 |
| A70 | 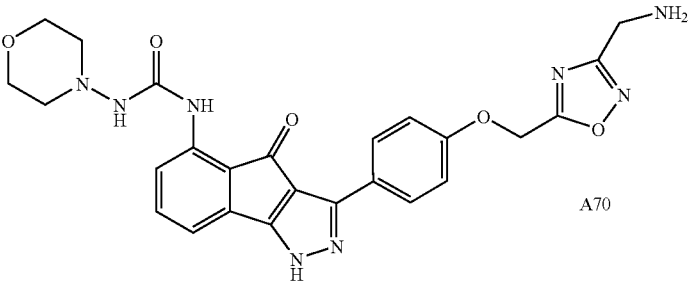 |
| A71 | 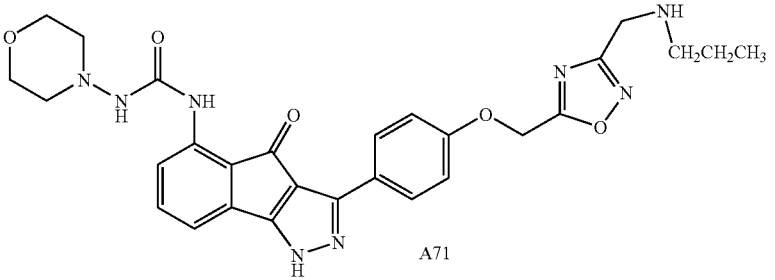 |

TABLE B-continued
| Compound | Structure |
|---|---|
| A72 | 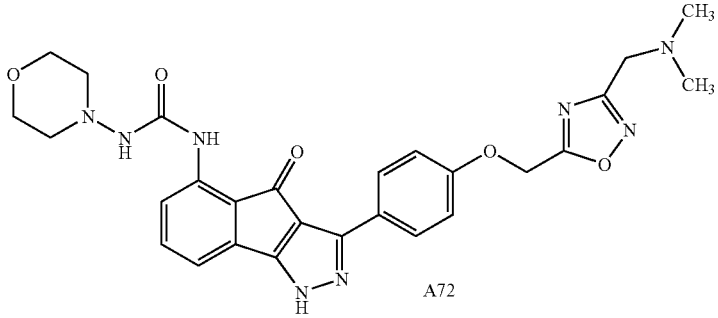 |
| A73 | 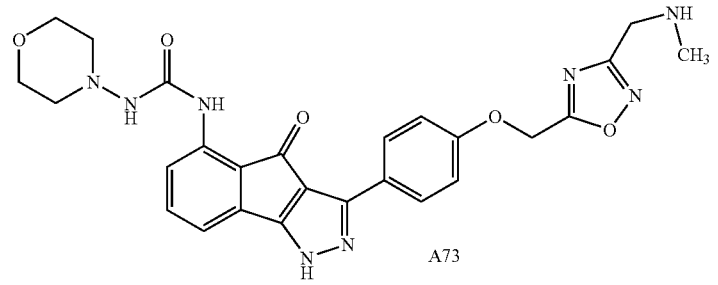 |
| A74 | 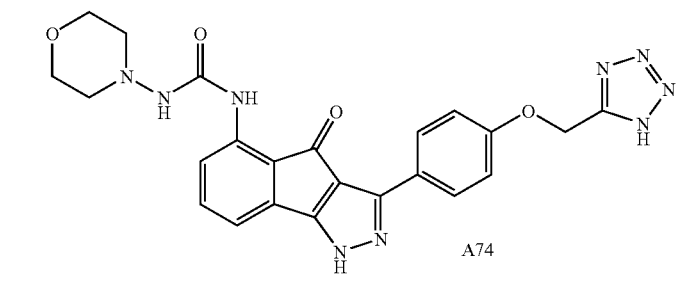 |
| A75 | 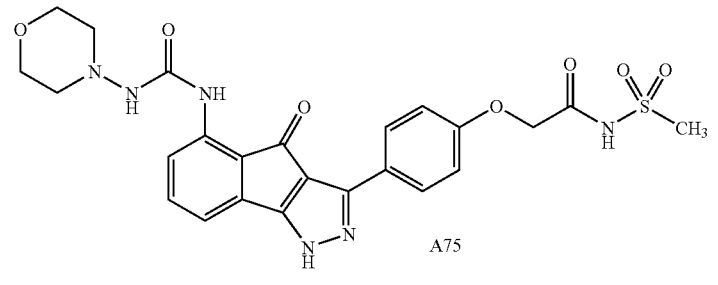 |
| A76 | 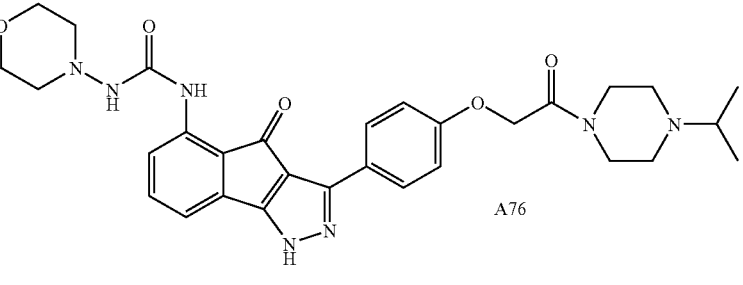 |

TABLE B-continued
| Compound | Structure |
|---|---|
| A77 | 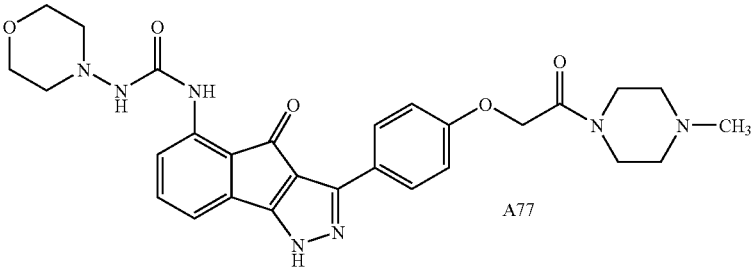 |
| A78 | 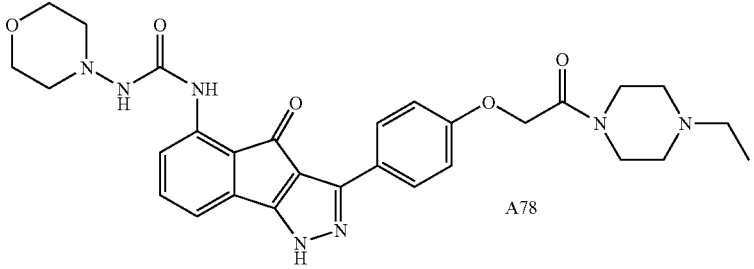 |
| A79 | 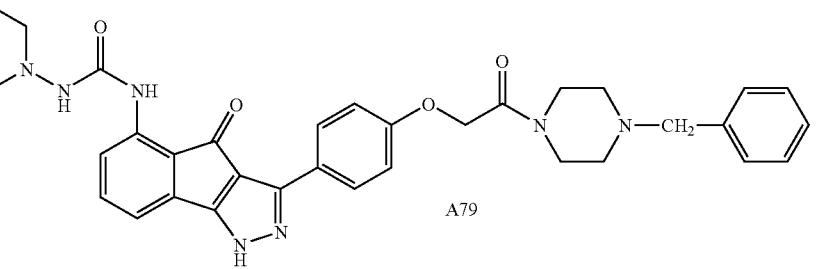 |
| A80 | 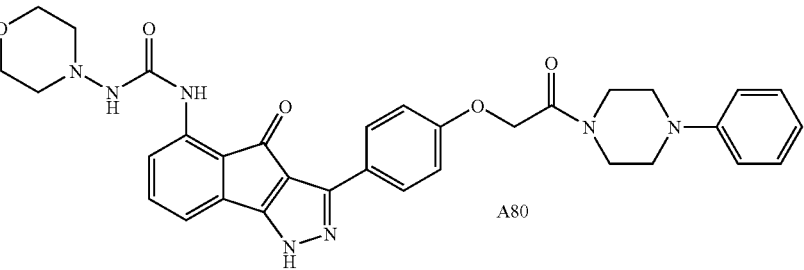 |
| A81 | 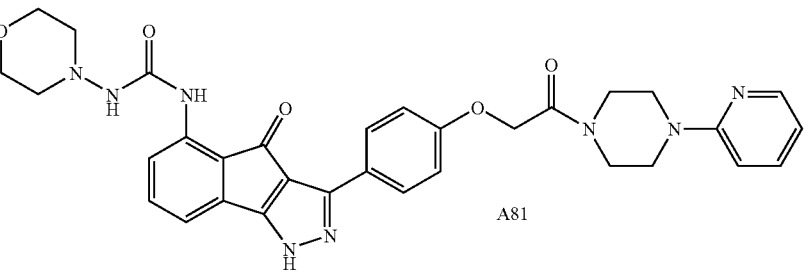 |

TABLE B-continued
| Compound | Structure |
|---|---|
| A82 | 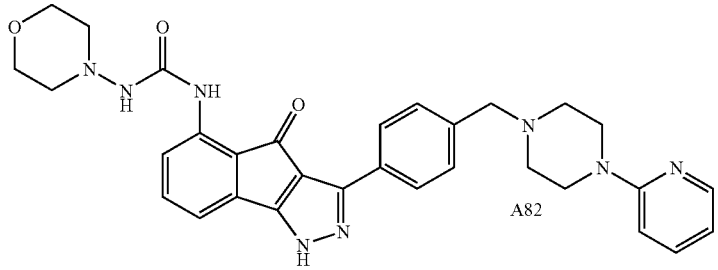 |
| B1 | 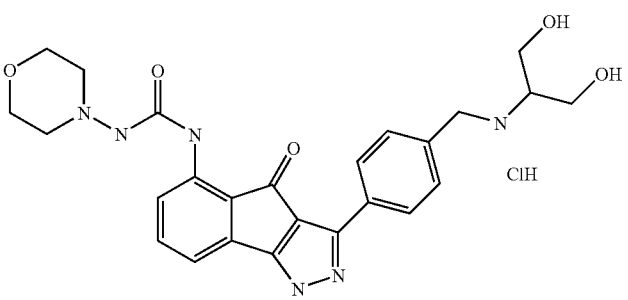 |
| B2 | 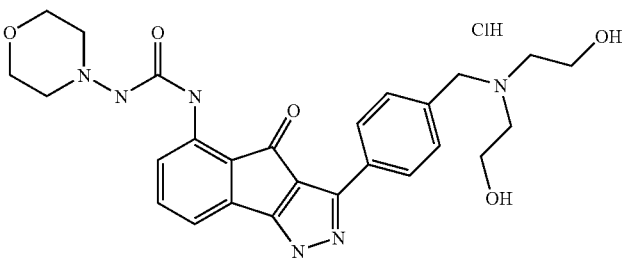 |
| B3 | 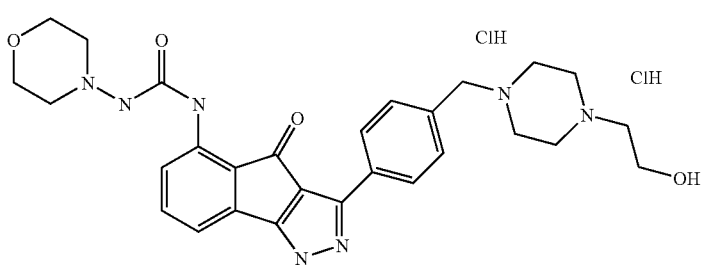 |
| B4 | 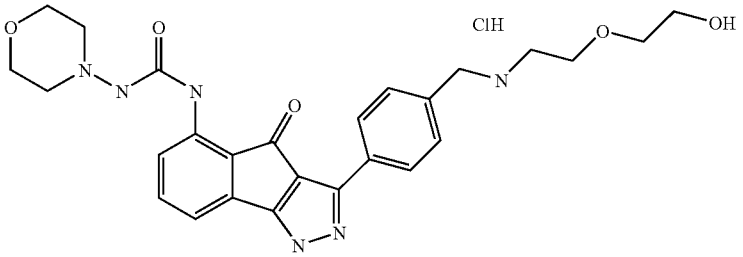 |

TABLE B-continued
| Compound | Structure |
|---|---|
| B5 | 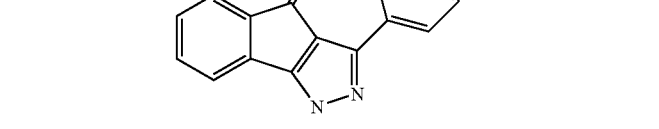 |
| B6 | 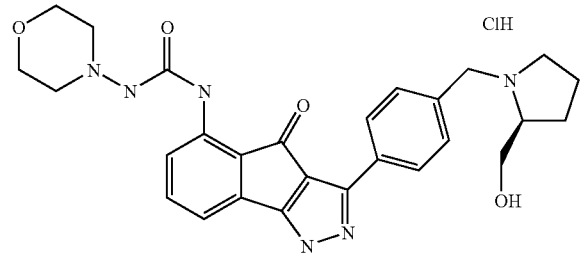 |
| B7 | 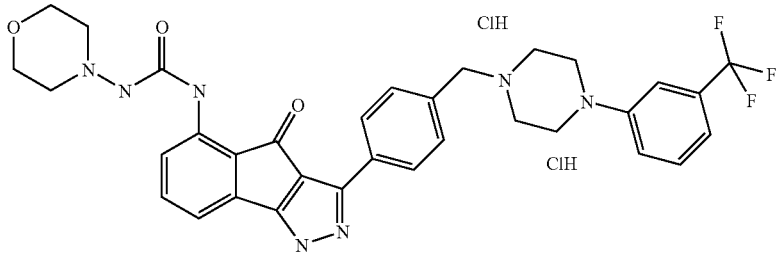 |
| B8 | 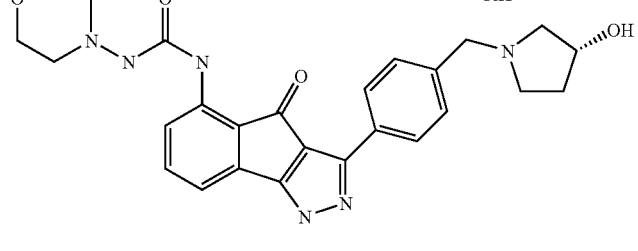 |
| B9 | 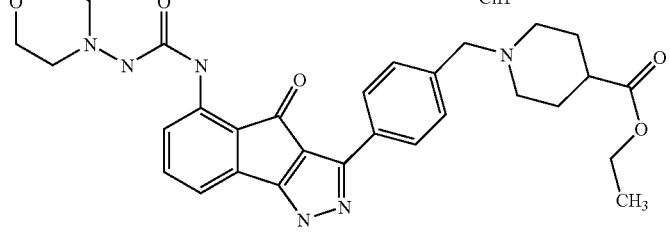 |
| B10 | 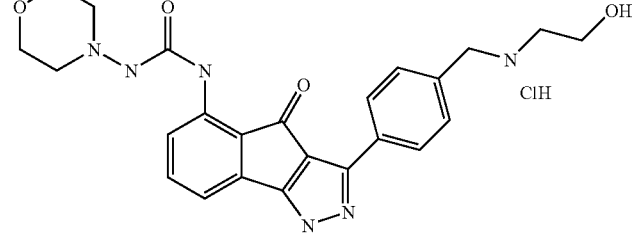 |

| Compound | Structure |
|---|---|
| B11 | 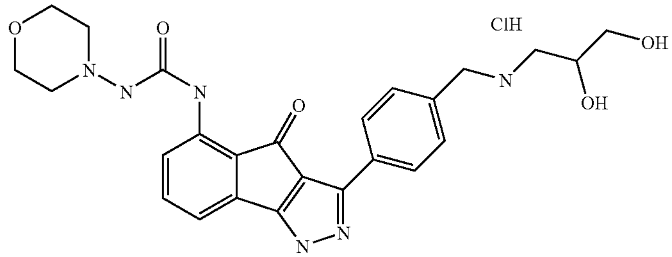 |
| B12 | 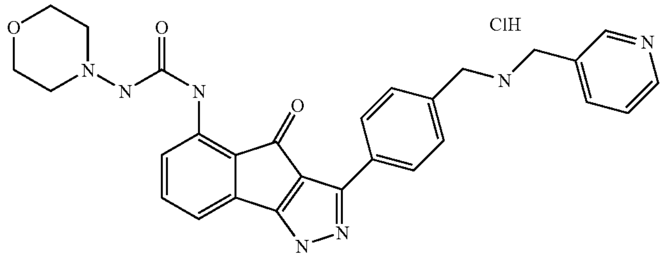 |
| B13 | 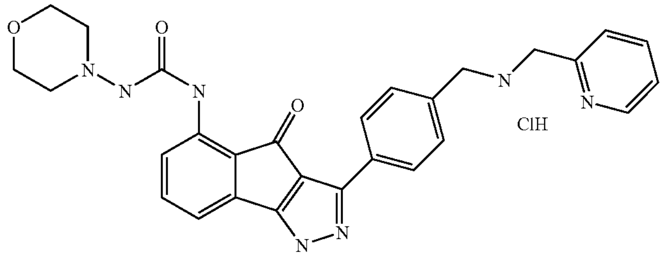 |
| B14 | 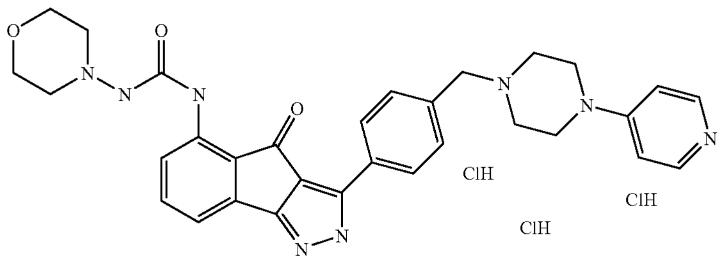 |
| B15 | 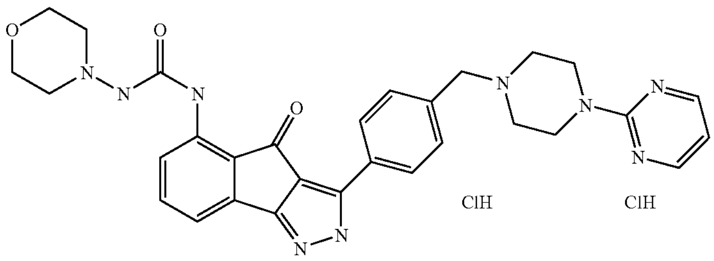 |

TABLE B-continued

TABLE B-continued
| Compound | Structure |
|---|---|
| B16 | 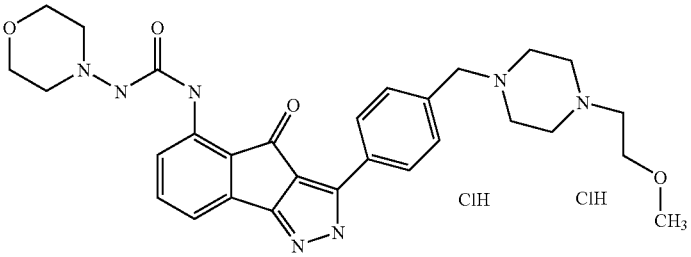 |
| B17 | 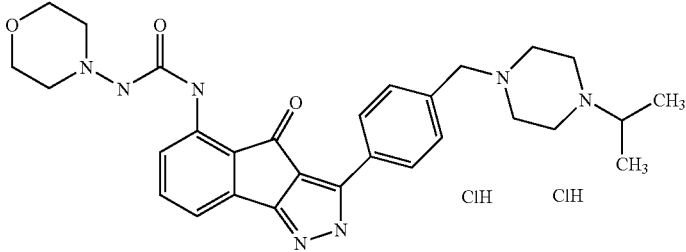 |
| B18 | 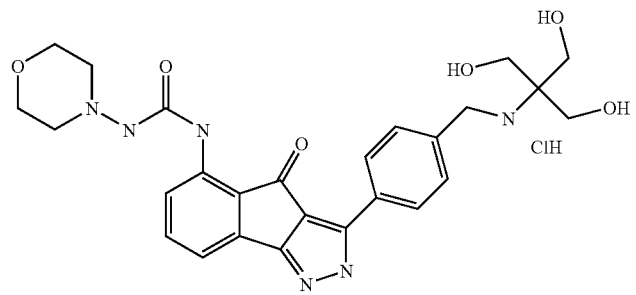 |
| B19 | 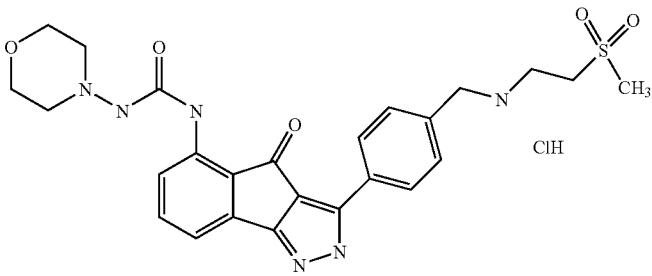 |
| B20 | 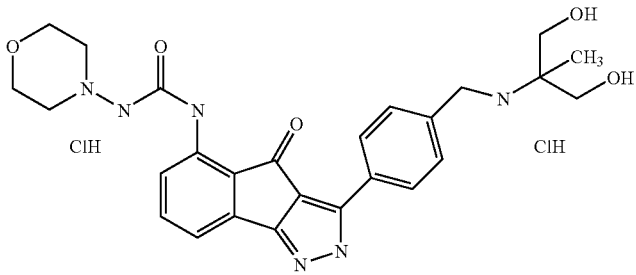 |

TABLE B-continued

| Compound | Structure |
| --- | --- |
| C1 | 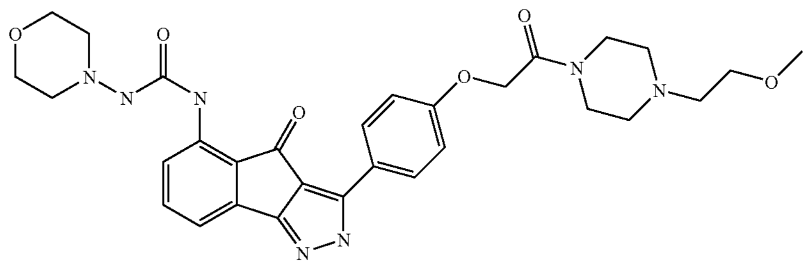 |
| C2 | 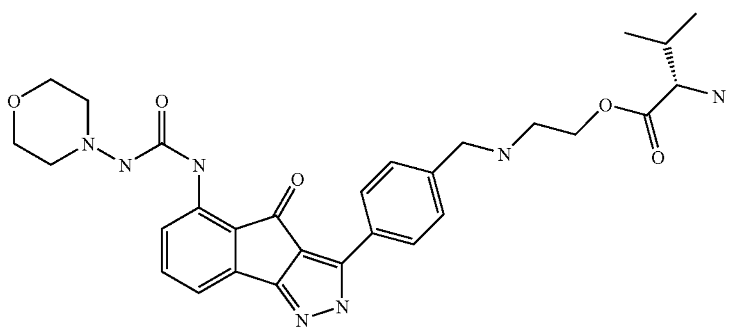 |
| C5 | 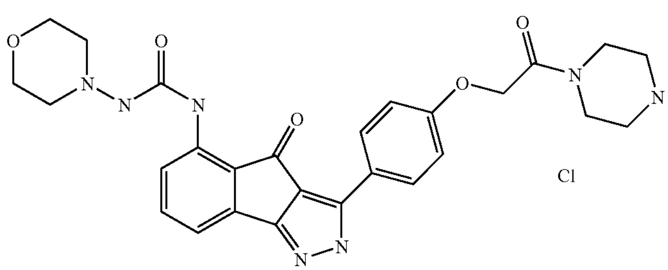 |

TABLE C

| Compound | Structure |
| --- | --- |
| G1 | 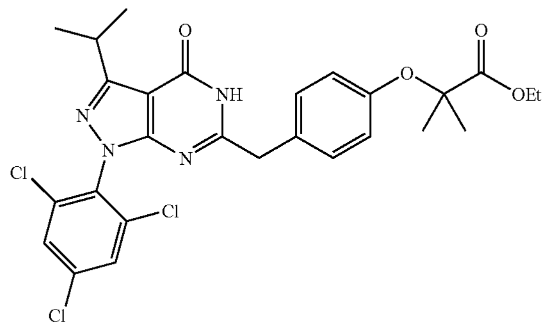 |

TABLE C-continued
| Compound | Structure |
| --- | --- |
| G2 | 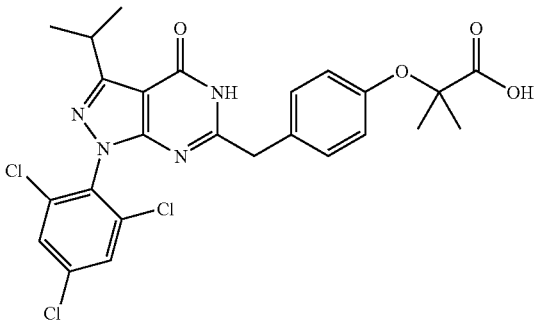 |
| G3 | 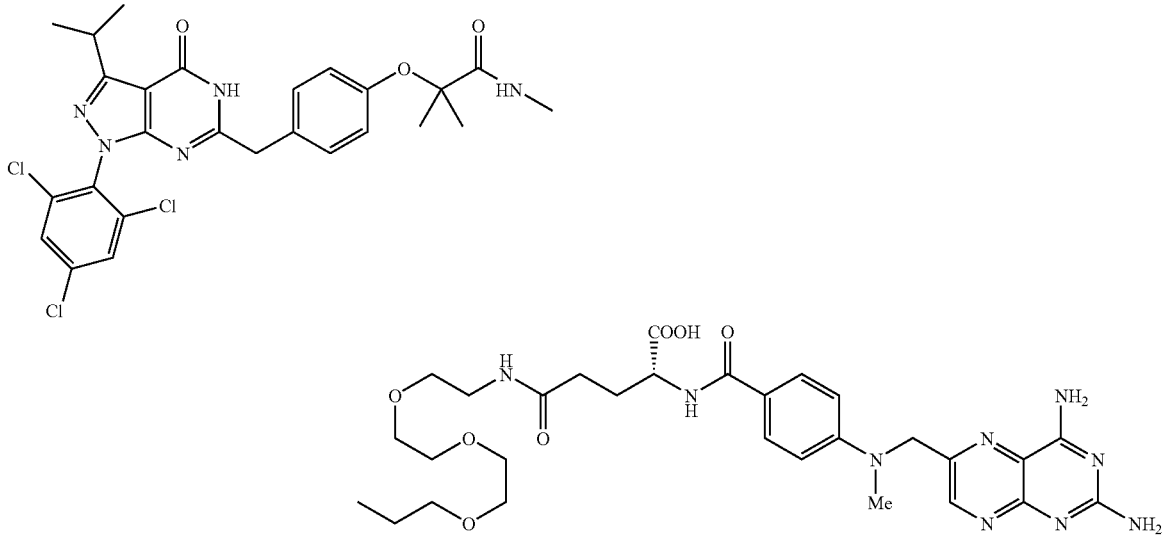 |
| G4 | 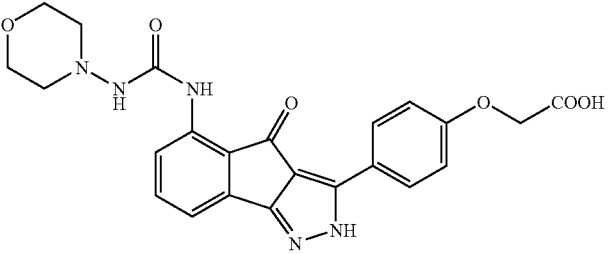 |

TABLE C-continued

| Compound | Structure |
|---|---|
| G5 | 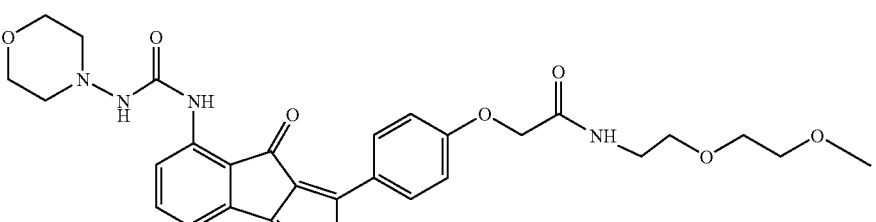 |
| G6 | 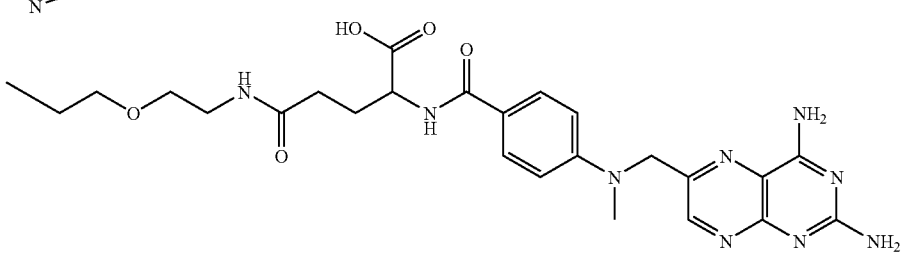 |

TABLE D

Other compounds of the invention result from selecting appropriate features from the table of possible features below. For example, compound A77 results from the following selections: none-morpholino-aryl-OCH$_2$(CO)-piperazine-CH$_3$.

| Left-hand substituent | Left-hand ring | Aryl or heteroaryl | Ring substituent | Nitrogen feature | Right-hand substituent |
|---|---|---|---|---|---|
| CH3 | morpholino | aryl | OCH2 | NHM | alkyl |
| isopropyl | piperazine | thiopene | OCH2(CO) | NMM | alkoxy |
| CH3CH2O(CO)CH2 | | | SO2 | morpholino | alcohol |
| none | | | OCH2(CO)OCH2 | piperazine | substitued amine |
| | | | | piperidine | acid |
| | | | | pyrazole | ester |
| | | | | pyrrolodine | CH$_2$CH$_2$OCH$_3$ |
| | | | | | CH$_2$CH$_2$OH |
| | | | | | CH$_2$NH$_2$ |
| | | | | | CH$_2$NHCH$_2$CH$_2$CH$_3$ |
| | | | | | CH$_2$NHCH$_3$ |
| | | | | | CH$_2$NHCHCH$_3$CH$_3$ |
| | | | | | CH$_3$ |
| | | | | | CHCH$_3$CH$_3$ |
| | | | | | COOCH$_2$CH$_3$ |
| | | | | | none |

The invention claimed is:
1. A compound of the structure
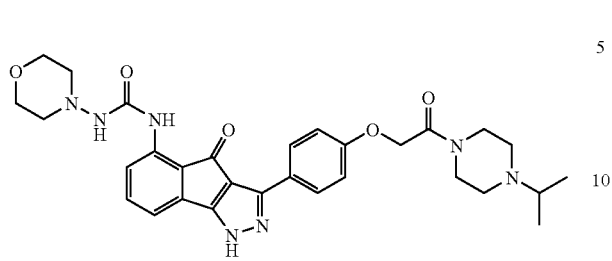
or a prodrug, tautomer, pharmaceutically acceptable salt, N-oxide, or stereoisomer thereof.
2. The compound of claim 1 having the structure
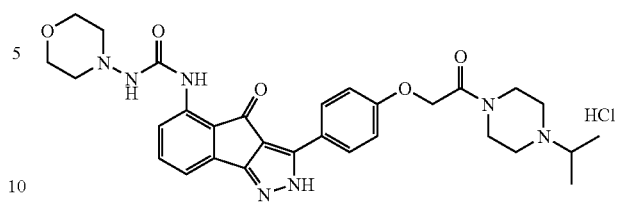
3. A pharmaceutical composition comprising a pharmaceutically acceptable excipient and a compound of claim 1 or 2.
* * * * *